(12) United States Patent
Tesson et al.

(10) Patent No.: US 11,993,563 B2
(45) Date of Patent: May 28, 2024

(54) SOLID COMPOSITIONS OF COCRYSTALS OF CANNABINOIDS

(71) Applicant: ENANTIA S.L., Barcelona (ES)

(72) Inventors: Nicolas Tesson, Barcelona (ES); Montserrat Trilla Castaño, Barcelona (ES); Alexander Christian Comely, Barcelona (ES)

(73) Assignee: ENANTIA S.L., Barcelona (ES)

( * ) Notice: Subject to any disclaimer, the term of this patent is extended or adjusted under 35 U.S.C. 154(b) by 454 days.

(21) Appl. No.: 17/286,949

(22) PCT Filed: Oct. 31, 2019

(86) PCT No.: PCT/EP2019/079899
§ 371 (c)(1),
(2) Date: Apr. 20, 2021

(87) PCT Pub. No.: WO2020/089424
PCT Pub. Date: May 7, 2020

(65) Prior Publication Data
US 2021/0380514 A1 Dec. 9, 2021

(30) Foreign Application Priority Data

Oct. 31, 2018 (EP) .................................... 18382776
Feb. 1, 2019 (EP) .................................... 19382074

(51) Int. Cl.
| | | |
|---|---|---|
| *C07C 37/84* | (2006.01) |
| *A61K 31/05* | (2006.01) |
| *A61K 31/352* | (2006.01) |
| *C07C 37/88* | (2006.01) |
| *C07C 39/19* | (2006.01) |
| *C07C 39/23* | (2006.01) |
| *C07C 229/12* | (2006.01) |
| *C07C 229/22* | (2006.01) |
| *C07D 311/80* | (2006.01) |
| *A61K 9/20* | (2006.01) |
| *A61K 9/48* | (2006.01) |

(52) U.S. Cl.
CPC ............. *C07C 37/84* (2013.01); *A61K 31/05* (2013.01); *A61K 31/352* (2013.01); *C07C 37/88* (2013.01); *C07C 39/19* (2013.01); *C07C 39/23* (2013.01); *C07C 229/12* (2013.01); *C07C 229/22* (2013.01); *C07D 311/80* (2013.01); *A61K 9/2013* (2013.01); *A61K 9/2095* (2013.01); *A61K 9/4808* (2013.01); *A61K 9/4858* (2013.01); *C07B 2200/13* (2013.01); *C07C 2601/16* (2017.05)

(58) Field of Classification Search
CPC ........ C07C 37/84; C07C 37/88; C07C 39/19; C07C 39/23; C07C 2601/16; C07C 229/12; C07C 229/22; C07D 311/80; A61K 31/05; A61K 31/352; A61K 31/658; C07B 2200/13

See application file for complete search history.

(56) References Cited

U.S. PATENT DOCUMENTS

| | | |
|---|---|---|
| 4,381,399 A | 4/1983 | Olsen et al. |
| 2017/0008870 A1 | 1/2017 | Dibble et al. |
| 2017/0283837 A1 | 10/2017 | Kavarana et al. |
| 2017/0298399 A1 | 10/2017 | Peet et al. |
| 2017/0362195 A1 | 12/2017 | Peet et al. |
| 2018/0000879 A1* | 1/2018 | Nadal Roura ....... A61K 36/185 |
| 2018/0325861 A1 | 11/2018 | Domb et al. |
| 2019/0177258 A1* | 6/2019 | Emanuele ............... C07C 39/23 |

FOREIGN PATENT DOCUMENTS

| | | |
|---|---|---|
| WO | WO 2004/026802 A1 | 4/2004 |
| WO | WO 2004/026857 A2 | 4/2004 |
| WO | WO 2006/053766 A1 | 5/2006 |
| WO | WO 2006/133941 A2 | 12/2006 |
| WO | WO 2007/041167 A2 | 4/2007 |
| WO | WO 2009/018389 A1 | 2/2009 |
| WO | WO 2014/134281 A1 | 9/2014 |
| WO | WO 2015/032519 A1 | 3/2015 |
| WO | WO 2016/030828 A1 | 3/2016 |

OTHER PUBLICATIONS

Sun et al. ("Particle Size Specification for Solid Oral Dosage Forms: A Regulatory Perspective", American Pharmaceutical Review, vol. 13, Issue 4, May/Jun. 2010, 9 pages). (Year: 2010).*
International Search Report and Written Opinion mailed Jan. 20, 2020 for Application No. PCT/EP2019/079899, 13 pages.
Baek, et al: "Boron trifluoride etherate on alimina—a modified lewis acid reagent. An improved synthesis of cannabidiol", Tetrahedron Letters 1985; vol. 26(8), pp. 1083-1086.
Bickler, et al: "Biotage Effective cannabinoid purification by flash chromatography", Poster ACS; Aug. 2016, 2 pages.
Diaz-Alonso, et al: "VCE-003.2, a novel cannabigerol derivative, enhances neuronal progenitor cell survivial and alleviates symptomatology in murine models of Huntington's disease", Scientific Reports; Jul. 19, 2016; vol. 6:29789, pp. 1-15.
Gaoni, et al: "Isolation, structure, and partial synthesis of an active constituent of hashish", Communications to the Editor; Apr. 20, 1964; vol. 86, pp. 1646-1647.
Gaoni, et al: "The isolation and structure Delta-1-tetrahydrocannabinol and other neutral cannabinoids from hashish", Journal of the American Chemical Society; Jan. 13, 1971; vol. 93(1), pp. 217-224.
Gunning: "Proceedings of the Chemical Society" Mar. 1964; pp. 73-100.

(Continued)

*Primary Examiner* — Rosalynd A Keys

(74) *Attorney, Agent, or Firm* — Squire Patton Boggs (US) LLP

(57) ABSTRACT

The present invention relates to solid compositions comprising cocrystals of cannabinoids, processes for their preparation, and their use as in therapy or in cosmetics or for the purification of cannabinoids. It also relates to cocrystals of cannabinoids.

2 Claims, 37 Drawing Sheets

(56) References Cited

OTHER PUBLICATIONS

Hazekamp, et al: "Structure elucidation of the tetrahydrocannabinol complex with randomly methylated-cyclodextrin", European Journal of Pharmaceutical Sciences; Jul. 6, 2006; vol. 29, pp. 340-347.
Kumar, et al: "Pharmaceutical cocrystals: an overview", Indian Journal of Pharmaceutical Sciences; Nov.-Dec. 2017; vol. 79(6), pp. 858-871.
Mechoulam, et al: "Carboxylation of resorcinols with methylmagnesium carbonate. Syntheseis of cannabinoid acids", Chemical Communications 1969; vol. 7, pp. 343-344.
Mechoulam, et al: "Stereoselective cyclizations of cannabinoid 1, 5 dienes", Tetrahedron Letters 1969; vol. 60, pp. 5349-5352.
Pertwee, et al: "Cannabidiolic acid methyl ester, a stable synthetic analogue of cannabidiolic acid, can produce 5-HT1A receptor-mediated suppression of nausea and anxiety in rats", British Journal of Pharmacology 2018; vol. 175, pp. 100-112.
Petrzilka, et al : "Synthese und chiralität des (−)-cannabidiols", Helvetica Chimica Acta. 1967 ; vol. 50(2), pp. 719-723 (with English Summary).
Petrzilka, et al : "Synthese von haschisch-inhaltsstoffen", Helvetica Chimica Acta. 1969 ; vol. 52(4), pp. 1102-1134.
Pollastro, et al: "Iodine-promoted aromatization of p-methane-type phytocannabinoids", Journal of Natural Products 2018; published Dec. 14, 2017; vol. 81(,3) pp. 630-633.
Ribi, et al: "Purification of Delta-9-tetrahydrocannabinol, an active constituent of marihuana, by accelerated microparticle gel chromatography", Preparative Biochemistry 1973; vol. 3(3), pp. 209-220.
Shoyama, et al: "Cannabis X.V. Preparation and stability of Delta-9-tetrahydrocannabinol-B-cyclodextrin inclusion complex", Journal of Natural Products; Sep.-Oct. 1983; vol. 46(5) pp. 633-637.
Sisa, et al: "Concise access to primin, miconidin and related natural resorcinols", Tetrahedron Letters; Jul. 15, 2017; vol. 73, pp. 5297-5301.
Straight, et al: "Marihuana extraction and purification for oral administration of known amounts of Delta-9-tetrahydrocannabinol (THC)", Biochemical Medicine 1973; vol. 8, pp. 341-344.
Taura, et al: "Purification and characterization of cannabidiolic-acid synthase from *Cannabis sativa* L.", The Journal of Biological Chemistry; Jul. 19, 1996; vol. 271(29), pp. 17411-17416.
Tilborg, et al "Pharmaceutical salts and cocrystals involving amino acids: A brief structural overview of the state-of-the-art", European Journal of Medicinal Chemistry; Jan. 18, 2014; vol. 74(18), pp. 411-426.

\* cited by examiner

SOLID COMPOSITIONS OF COCRYSTALS OF CANNABINOIDS

CROSS-REFERENCE

This application is a 35 USC 371 national phase filing of PCT/EP2019/079899 filed on Oct. 31, 2019, which claims the benefit of and priority to the European Patent Application no. 18382776.5 filed on Oct. 31, 2018 and the European Patent Application no. 19382074.3 filed on Feb. 1, 2019, all of these applications are incorporated herein by reference in their entirety.

The present invention relates to solid compositions comprising cocrystals of cannabinoids, processes for their preparation, and their uses in therapy, in cosmetic and for the purification of cannabinoids. It also relates to cocrystals of cannabinoids.

BACKGROUND ART

*Cannabis sativa* plant has been used for several hundreds of years both recreationally and medicinally. It contains three major classes of bioactive molecules: flavonoids, terpenoids and more than 60 types of cannabinoids including Cannabidiol (abbreviated as (−)-CBD or CBD)), Trans-(−)-$\Delta^9$-tetrahydrocannabinol (abbreviated as $\Delta^9$-THC, (−)-$\Delta^9$-THC, trans-(−)-(−)-$\Delta^9$-THC, tetrahydrocannabinol or THC), Trans-,(−)-$\Delta$8-tetrahydrocannabinol (abbreviated $\Delta$8-THC or delta8-THC), Cannabidivarin (abbreviated as CBDV), Cannabigerol (abbreviated as CBG), Cannabicromene (abbreviated as CBC) and Cannabinol (abbreviated as CBN). Some of them are present only in small proportions in *Cannabis* plant (minor cannabinoids) and have not been fully studied due the difficulty to obtain pure sample.

Furthermore, additional semi-synthetic cannabinoids are being developed to optimize its properties. Some examples include HU-580 (a derivative of CBDA—*British Journal of Pharmacology*, 2018, 175 100-112) and VCE-003.2 (a derivative of CBG—*Sci Rep,* 2016, 6:29789, 1-15). This definitely expands the possibilities of number of cannabinoids.

Cannabinoids is a family of complex terpenophenolic compounds that exert most of their actions by binding to and activating specific G$\alpha$i protein-coupled receptors named as cannabinoid receptor, such as CB1 and CB2. Several strains of *Cannabis* plants are found to have a significant variation in the ratios of each cannabinoid and also to contain some cannabinoids with psychotropic effect (such as THC) mediated by the CB1 receptors located in the central nervous.

Due to the psychotropic and addictive issues, the use cannabinoids in therapy is in question. Even though this psychotropic effect of some cannabinoids, cannabinoid receptors and their endogenous ligands have been used as putative molecular targets for the treatment of various diseases, including among others neurodegenerative diseases (Alzheimer's disease, Parkinson's disease, Huntington's disease, etc.), neuropathic and inflammatory pain, glaucoma, multiple sclerosis, cardiovascular disorders and obesity. Besides, cannabinoid's role has been also explored in the area of cancer research by its ability in targeted killing of tumors. In fact, several preclinical studies suggest that THC have anti-cancer effects in vitro against lung carcinoma, gliomas, thyroid epithelioma, lymphoma, skin carcinoma, uterine carcinoma, breast cancer, prostate carcinoma, pancreatic cancer and neuroblastoma. Finally, cannabinoids also have palliative effects due to the inhibition of nausea and emesis associated with chemo- or radiotherapy; appetite stimulation; pain relief; mood elevation and relief from insomnia in cancer patients. Minor cannabinoids have shown promise for potential use as non-opioid analgesics but there has been little research on these substances to understand their effects (especially when used on a long-term basis) and underlying mechanisms because of the difficulties to isolate them with enough amounts in order to perform these studies.

The use of cannabinoids in therapy implies the preparation of appropriate compositions that comply with the strict criteria of the regulatory agencies. However, the chemical and physical properties of cannabinoids hinder the preparation of oral compositions containing them without compromising the required chemical stability of cannabinoids and having the appropriate oral bioavailability.

Cannabinoids are generally sensitive to the conditions commonly used for their preparation and storage. It is known that under basic or acid media and/or in the presence of air and/or expose to light, some cannabinoids can be oxidized or decomposed into undesirable by-product. Particularly, it is disclosed in the state of the art that under basic media and in the presence of air, CBD is oxidized; and that under acidic conditions CBD is cyclized to obtain the undesirable by-product THC which is the responsible of the psychotropic effects. THC can also undergo oxidation to CBN which is used as a chemical indicator of poor or lengthy storage condition of *Cannabis* hemp plant.

Further, it is also known that some cannabinoids, such as CBD, are photoreactives, which mean that they should be guarded from light when stored.

In order to overcome the low chemical stability of cannabinoids during their preparation, a multitude of routes of synthesis for the preparation of cannabinoids, particularly CBD, THC, CBN, CBG and CBDV have been developed.

In the case of CBD, it can be obtained by several processes either by synthetic routes or by extraction processes from plants such as those of the genus *Cannabis*. In one hand, CBD's extraction processes typically involve one or more extraction steps from the *Cannabis* plant; followed by decarboxylation steps to transform the acid form of cannabinoids (such as tetrahydrocannabinolic acid (THCA) and cannabidiolic acid (CBDA)) into neutral cannabinoids in mixture form (including THC and CBD); and supplying the mixture thus obtained to one or more purification steps. On the other hand, several synthetic processes have been also disclosed in the state of the art for the preparation of CBD. In particular, these synthetic processes are based on acid-catalysed terpenylation of phenols (for example the acid-catalyzed condensation of (+)-p-mentha-2,8-dien-1-ol with olivetol). The reaction conditions of these reaction involve the use of N,N-dimethylformamide dineopentyl acetal (cf. T. Petrzilka et al. "synthese and chiralitat des (−)-cannabidiols vorläufige mitteilung". Helvetica Chimica Acta. 1967, vol. 50(2), pp. 719-23); picric acid, oxalic acid or maleic acid (cf. T. Petrzilka et al. "synthese von haschisch-inhaltsstoffen. 4. Mitteilung". Helvetica Chimica Acta. 1969, vol. 52(4), pp. 1102-34); p-toluensulfonic acid (PTSA) (cf. PCT patent application WO2009018389); or $BF_3$-$Et_2O$/alumina (cf. Tetrahedron Letters 1985, 26(8), 1083); or $ZnCl_2$ (cf. PCT patent application WO2006133941).

In the case of THC, it can also be obtained by synthetic routes or by extraction processes from natural products (such as hashish or marijuana). Some of these processes involve the extraction of the derivative $\Delta^9$-tetrahydrocannabinoic acid (also named $\Delta^9$-THC acid or THCA) from flowers of plants of the genus *Cannabis* followed by its conversion into THCA salt before being extracted by a third organic solvent and converted back to $\Delta^9$-THC carboxylic acid. Finally, using a solvent swap, $\Delta^9$-THC carboxylic acid is decarboxylated and extracted again with an organic solvent prior to purification to give $\Delta^9$-THC. Another known synthetic processes are based on the reaction of cis/trans mixture of (+)-p-mentha-2,8-dien-1-ol with olivetol in the presence of an acid catalyst such as p-toluenesulfonic acid and a dehydrating agent; or the reaction of cannabidiol in EtOH in the presence of hydrochloric acid (*J. Am. Chem. Soc.* 1964, vol. 86, page 1646) or with a Lewis acid such as $BF_3$-$Et_2O$ in an inert solvent under anhydrous conditions (*J. Am. Chem. Soc.*, 1971, vol. 93, pages 217-224). Its synthesis from CBD was also subsequently reported by (Mechoulam R. and Ben-Zvi Z., *Chem Commun,* 1969, 7, 343-344).

In the case of minor cannabinoids, they can also be obtained by synthetic routes in order to overcome isolation issues due to their very low proportion in natural *Cannabis* extracts. Furthermore, synthetic preparation allows to prepare enough quantities to perform in-vivo investigations and clinical trials studies, but it is difficult to reach high required purities without performing column chromatography. In the case of CBDV, it can be obtained by a similar synthetic way to CBD but the starting material derived from olivetol, not commercially available, has to be prepared in two steps from 1-bromo-3,5-dimethoxybenzene according to the method described in *Tetrahedron* 2017, 73, 5297-5301). In the case of CBN, it can be prepared directly from CBD by reaction with iodine in toluene at 110° C. (J. Nat. Prod. 2018, 81 (3), 630-633). In the case of CBG, it can be obtained following a one-step synthetic route starting from commercially available geraniol and olivetol using as catalizador p-toluenesulfonic acid (PTSA) or a Lewis acid (Tet. Lett. 1985, 26 (8), 1083-1086)

However, these processes give the desired cannabinoid with a considerable number of undesirable by-products (including related compounds in some cases difficult to separate by crystallisation or column chromatography).

The purification steps of the preparation or extraction processes disclosed above can comprise evaporation steps (to remove volatile impurity); winterization procedures (to remove wax impurity); filtration through silica plug (to remove highly polar impurities); column chromatography, crystallization and high vacuum (to remove residual solvent); or the use of a combination of fractional distillation and crystallization of cannabinoids from organic solvent media. All these purification steps are laborious, time consuming, not economical and even using them, cannabinoids can be obtained in low yield.

Thus, it has been disclosed in the state of the art processes for increasing the purity of cannabinoids. In particular, in the case of CBD, it is known that the use of an ester of olivetolic acid as starting material instead of olivetol allows increasing the purity of CBD (cf. PCT patent applications WO2007041167 and WO2015032519). In these processes, an additional decarboxylation step is at least necessary to obtain pure CBD. However, the ester of olivetolic acid is very expensive and its use hinders the cost-effectiveness of this route. As it is disclosed above for CBD, several purification methods have been also disclosed in the art with the aim to increase the purity of $\Delta^9$-THC. Some of these methods involve the fractional distillation under vacuum to separate volatile cannabinoids from low-boiling components and non-volatile; chromatography separation using Sephadex LH20™ column (cf. *Biochemical Medicine,* 1973, 8(3), 341-344; and WO2004026857A2-GW Pharma); accelerated microparticulate gel chromatography (cf. *Preparative Biochemistry,* 1973, 3(3), 209-220); or orthogonal chromatography using normal and reverse phase flash chromatography (cf. poster ACS, Philadelphia, 2016, Biotage). In order to improve the separation of $\Delta^9$-THC from the different impurities by chromatography, $\Delta^9$-THC derivatives ($\Delta^9$-THC esters) have been prepared. As (−)-$\Delta^9$-THC is not crystalline, the crystallization of racemic (±)-$\Delta^9$-THC or (±)-$\Delta^9$-THC m-nitrobenzenesulfonate followed by a separation by chiral chromatography in order to separate both enantiomers has been disclosed in WO2006053766A1 to purify the crude. However, (+)-$\Delta^9$-THC has to be synthetized to prepare (±)-$\Delta^9$-THC because the racemic form is not a natural compound. Another purification process comprising the crystallization of $\Delta^9$-tetrahydrocannabinlic acid ((−)-THCA) as a pale yellow crystalline solid at room temperature, having a melting point in the range of 45-48° C. has also been disclosed (cf. US2017008870A1). Finally, chromatography of the $\Delta^9$-THC ester derivative obtained by submitting to esterification conditions the crude mixture has also been disclosed in the state of the art. This process comprises isolating the resultant esters from the crude mixture by chromatography, followed by firstly the hydrolysis of the esters and the subsequent distillation of $\Delta^9$-THC obtained at reduced pressure (cf. U.S. Pat. No. 4,381,399A).

Unfortunately, fractional distillation of cannabinoids is generally not efficient to separate isomers or other related cannabinoids from each other. Furthermore, as some cannabinoids, such as THC, are heat sensitive this purification technique could also lead to degradation products. Furthermore, purification by chromatography methods is expensive and difficult to perform at industrial scale. In order to meet the purity requirement, several purifications by chromatography can be necessary using in some cases different columns and non-friendly solvents.

On the other hand, some of these cannabinoids described as oily or gum products (such as CBC, THC or delta8-THC) are difficult to manipulate and its chemical stabilities are generally lower than crystalline forms.

In the case of THC, it has been disclosed as a resinous light yellow oil and semisolid product even when it is obtained with very high purity. Unfortunately, this physical state hinders its manufacturing and purification, and it is not readily adapted for incorporation into standard dosage forms that are typically available for other solid pharmaceutical compounds.

Despite the complexity of obtaining and purifying cannabinoids, the formulation of these products in solid compositions (such as tablets, hard capsules and granules) is even more complex and, without a doubt, has not yet been solved efficiently.

An important disadvantage of some cannabinoids (such as CBD, CBG, and CBN) for their formulation is their low melting points (about 52-77° C.) leading to potential localized melting processes during high energy formulation steps such as milling, compression and coating processes; or oily/pasty amorphous products (such as THC and delta8-THC). In both cases a significant risk for the chemical stability of cannabinoids during formulation and also during the storage of those formulations could be present. This property also jeopardize the own stability and uniformity of the solid formulation, independently of the stability of the active ingredient itself. Therefore, the preparation of solid formulations of cannabinoids is not recommended.

All the above mentioned disadvantages for the preparation of appropriate oral compositions disclosed above results in the development of oral liquid compositions such as those which have been approved in the different regulatory agencies. In fact, the approved oral compositions containing cannabinoids are in form of solutions or emulsions despite the great advantages of solid compositions.

Particularly, Sativex is a mouth oromucosal spray containing an extract obtained from the *Cannabis* plant which includes tetrahydrocannabinol (THC) and cannabidiol (CBD). Sativex has been approved in several countries to treat ailments including cancer pain and multiple sclerosis spasticity. On the other hand, THC has also been approved as Marinol which is supplied as round, soft gelatin capsules (for oral use) that include the THC dissolved in sesame oil. Marinol is indicated for the treatment of anorexia associated with weight loss in patients with Acquired immune Deficiency Syndrome (AIDS) and also for nausea and vomiting associated with cancer chemotherapy in adults.

Recently, the U.S. Food and Drug Administration (FDA) has approved Epidiolex that is the first prescript drug made from *Cannabis* plant which includes highly purified cannabidiol (CBD). It is advantageous because it does not cause the addictive effect (also call 'high') associated with the presence of THC. Epidiolex is marketed as an oral solution containing CBD for the treatment of seizures associated with two rare and severe forms of epilepsy, Lennox-Gastaut syndrome and Dravet syndrome in children.

However, these orally administrable liquid formulations still maintain some disadvantages. Firstly, they contain excipients that lead to lesions, ulcerations, pain and soreness of the oral mucosa, which results in an interruption of the treatment. Secondly, they also contain ethanol as a vehicle that is not recommended for those people who suffer or have suffered from alcohol addiction. Thirdly, the stability of dissolved cannabinoids in the liquid compositions is compromised, resulting in increasing the speed of the degradation of cannabinoid, shortening the expiration date of such formulations. Fourthly, these liquid compositions are oral mucosal absorption compositions having notable inter-subject variability in their pharmacokinetic profile, leading to an increasing number of daily dose administrations for ensuring the pharmacological activity.

Furthermore, another major drawback of cannabinoids is its low oral bioavailability (ranging from 6-33% in humans). This low bioavailability is due to its low aqueous solubility in combination with an extensive first-pass metabolism.

In order to overcome their very low aqueous solubility and obtaining solid compositions, complexes with cyclodextrins or maltodextrins suitable for sublingual administration have been disclosed in the state of the art. These complexes have been obtained by evaporation to dryness or by co-precipitation followed by freeze-drying, which means that these complexes are not in a crystalline form hindering the preparation of pharmaceutical composition containing them. In addition, these complexes could reduce the bioavailability of the active ingredients.

Other alternative formulations for overcoming their low oral bioavailability are the preparation of oral formulations that in contact with aqueous media, nanoparticles of cannabinoids having a size less than 500 nm are generated. This is achieved by the use of liquid formulations that include a surfactant, a lipid component and a water-soluble amphiphilic solvent. These liquid compositions can be transformed into solid-supported compositions by their adsorption to a solid substrate using poly(meth)acrylates as layering or coating agents. Unfortunately, the preparation of these solid supported compositions implies a complex process which implies first the preparation of the pre-concentrated emulsion of cannabinoids and its subsequent deposition in a solid support (cf. US2018325861). As it is mentioned above, the excessive manipulation of cannabinoids even in liquid form and during the preparation of solid-support solid formulations hinder the chemical stability of cannabinoids and its oral bioavailability. Furthermore, the appropriate and effective release of the cannabinoids from the solid support can be also compromised.

Therefore, from what it is known in the state of the art, there is a long-felt need to find a solid composition for oral administration comprising one or more cannabinoids which meet the strict regulatory requirements and appropriate oral bioavailability.

SUMMARY OF INVENTION

The inventors provide a solid composition suitable for oral administration that overcomes the problems disclosed in the state of the art associated with the chemical instability of cannabinoids during their preparation and also during the manufacturing and storage of the composition containing them; as well as the side effects associated with their oral administration and low bioavailability. The solid composition also overcomes the problems associated with the cannabinoids' solid compositions itself.

In particular, the inventors have found that the use of cocrystals of non-crystalline cannabinoids or cocrystals of cannabinoids having a higher melting point than the cannabinoid allows preparing solid compositions by a simple, cost-effective and industrial scalable process without compromising neither the stability of the cannabinoids in the composition nor the own solid composition stability and uniformity of the solid composition. In fact, the increase in the melting point allows for reducing the potential amorphization due to localized melting of cannabinoids during the preparation of the oral composition or even during its storage. Therefore, the higher stability of the cocrystal of the cannabinoid makes it suitable for being used as a medicament because the solid compositions of the present invention containing the cocrystal comply with the strict criteria of impurities limit specifications of the medicine regulatory agencies.

In addition, the inventors have also unexpectedly found that the physical and mechanical properties of cocrystals of cannabinoids are suitable for the preparation of solid compositions. As it is shown in the Examples of the present invention, the use of the cocrystals of cannabinoids allows preparing simple solid compositions with few ingredients and easily available commercially having a high content of the active ingredient (from 1 to 80% by weight); which can be prepared by simple processes. In particular, both direct compression and dry granulation by pre-compression processes can be used for the preparation of tablets containing them.

Furthermore, the inventors have also found that the solid compositions of the invention which comprise one or more cocrystals of cannabinoids (having a high melting point) allows having the appropriate bioavailability even for being used as a medicament. Without being bound to any theory, it seems that the cocrystals enhance the solubility of the poorly-water soluble cannabinoid without altering its molecular structure. In particular, crystalline phase containing the cannabinoid and the coformer is dissociated in a short period of time in the biological medium. The coformer (which is the more water soluble component in the cocrystal) is drawn out of the crystal lattice into the aqueous medium. After dissociation, the hydrophobic cannabinoid become supersaturated in the aqueous biological medium, and this higher energy form is maintained for thus sufficient period of time to be absorbed before its precipitation.

It is also part of the invention that the use of cocrystals of cannabinoids allows preparing cannabinoids with a high purity and maintaining it during the manufacturing process of the solid composition. In fact, the use of cocrystals of cannabinoids allows purifying cannabinoids such as CBD, THC, CVDV and CBN with a simple, cost-effective and industrial scalable process even when the cannabinoid is obtained by plant extraction processes or by synthetic routes. Therefore, the solid compositions of the present invention containing cocrystals of cannabinoids comply with the impurity profile required by the regulatory agency.

Therefore, the inventors have found that the use of the cocrystals of cannabinoids offer a completely unexpected dual function allowing the purification of the cannabinoid and at the same time the preparation of solid compositions that contain them.

Accordingly, the use of cocrystals of cannabinoids for the preparation of stable solid compositions containing them is considered a contribution to the art.

Thus, a first aspect of the invention relates to a solid composition comprising an effective amount of one or more cocrystals of a cannabinoid and a zwitterion coformer; and one or more acceptable excipients or carriers; wherein the effective amount of the cocrystal is from 1% to 80% by weight of the solid composition.

The second aspect of the invention relates to a cocrystal of a cannabinoid selected from CBD, THC and delta8-THC and a zwitterion coformer.

The third aspect of the invention relates to a process for the preparation of the cocrystal as defined in the second aspect of the invention, which comprises: (c) slurrying the cannabinoid with the coformer and an organic solvent; and (d) isolating the cocrystal thus obtained.

Finally, the fourth aspect of the invention relates to a process for the purification of a cannabinoid which comprises: (e) dissociating a cocrystal as defined in the present invention under such reaction conditions to obtain the cannabinoid; and (f) isolating the cannabinoid thus obtained.

DETAILED DESCRIPTION OF THE INVENTION

Figure 1:
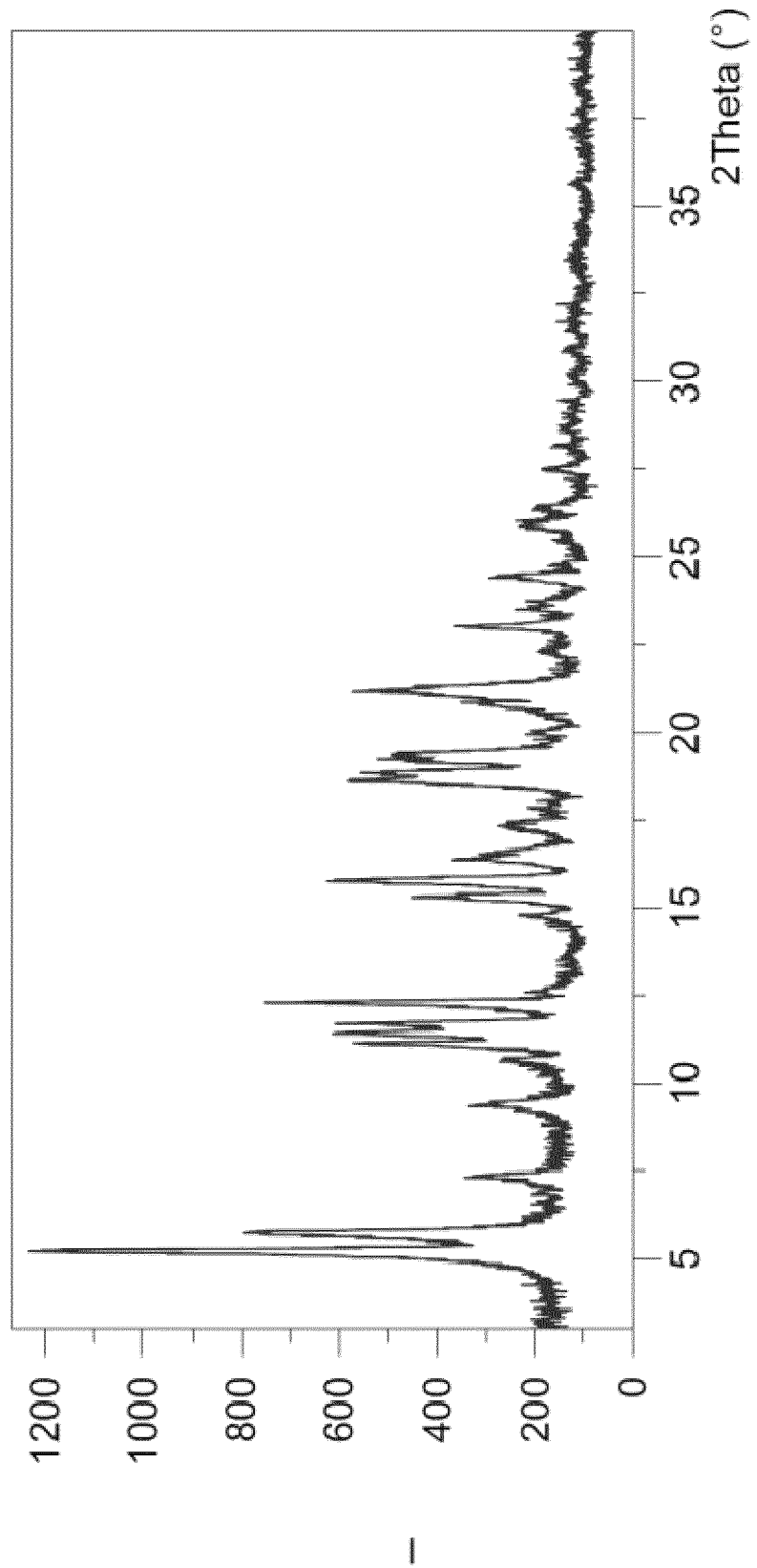
FIG. 1 shows the X-ray powder diffractogram (XRPD) of the cocrystal Form I. The spectrum expresses intensity (I; counts) versus degrees 2 theta (°).

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges and values given, such as temperatures, times, and the like, should be considered approximate, unless specifically stated.

When values of characteristic peaks of an X-ray diffractogram are given it is said that these are "approximate" values. It should be understood that the values are the ones shown in the corresponding lists or tables±0.3 degrees 2 theta measured in an X-ray diffractometer with Cu—K$_\alpha$ radiation λ=1.5406 Å.

The term "percentage (%) by weight" refers to the percentage of each ingredient of the composition in relation to the total weight.

The first aspect of the invention refers to a solid composition comprising an effective amount of one or more cocrystals of a cannabinoid and a zwitterion coformer; and one or more acceptable excipients or carriers; wherein the effective amount of the cocrystal is from 1% to 80% by weight of the solid composition.

In an embodiment, the solid composition of the present invention comprises an effective amount of the cocrystal is from 4% to 70% by weight of the solid composition; particularly from 6% to 60%, more particularly from 9% to 40%.

For the purposes of the invention, the term "solid composition" refers to any solid-state composition that is completely absence of liquid media. The solid compositions of the present invention can be prepared according to methods well known in the state of the art.

The appropriate excipients and/or carriers, and their amounts, can readily be determined by those skilled in the art according to the type of formulation being prepared.

In an embodiment, the solid composition is a "pharmaceutical solid composition" comprising a "pharmaceutically effective amount of the cocrystal" which comprises the cannabinoid and a "pharmaceutically acceptable coformer" together with one or more "pharmaceutically acceptable excipients or carriers". The term "pharmaceutical solid composition" refers to a solid composition suitable for use in the pharmaceutical technology with medical use. The term "pharmaceutically effective amount of the cocrystal" refers to the amount of the cocrystal which provides after its dissociation after administration a therapeutically (pharmaceutically) effective amount of the cannabinoid. The term "pharmaceutically acceptable coformer" refers to a coformer suitable for being used in the preparation of a pharmaceutical composition having medical use. It must also be suitable for use in contact with the tissue or organ of humans and animals without excessive toxicity, irritation, allergic response, immunogenicity or other problems or complications commensurate with a reasonable benefit/risk ratio. The term "pharmaceutically acceptable excipients or carriers" refers to that excipients or carriers suitable for use in the pharmaceutical technology for preparing compositions with medical use. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

In an embodiment, the solid composition is a "cosmetic solid composition" comprising a "cosmetically effective amount of the cocrystal" which comprises the cannabinoid and a "cosmetically acceptable coformer" together with one or more "cosmetically acceptable excipients or carriers". The term "cosmetic solid composition" refers to a solid composition suitable for improving the appearance or to beautify, preserve, condition, cleanse, color or protect the body, such as skin, nails and hair. Therefore, the above cosmetic solid composition is adjectivally used for a non-medical application (cf. Academic press Dictionary of Science and Technology, 1992, pp. 531; A terminological Dictionary of the Pharmaceutical Sciences. 2007, pp. 190). The term "cosmetically effective amount of the cocrystal" refers to the amount of the cocrystal which provides after its dissociation after administration a cosmetically effective amount of the cannabinoid. The term "cosmetically acceptable coformer" refers to a coformer suitable for being used in the preparation of a cosmetic composition having a non-medical use. It must also be suitable for use in contact with the tissue or organ of humans and animals without excessive toxicity, irritation, allergic response, immunogenicity or other problems or complications commensurate with a reasonable benefit/risk ratio. The term "cosmetically acceptable excipients or carriers" refers to that excipients or carriers suitable for use in the cosmetic technology for preparing compositions with medical use. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

In an embodiment, the pharmaceutical or cosmetic solid compositions of the invention can be formulated in any form that includes any single unit dosage form and any multiple unit dosage forms. The term "single unit" encompasses one entity such as a single tablet, a single capsule, a single granule, a powder and a single pellet. The term "single unit dosage form" defines a dosage form which consists only of one unit which contains the effective amount of the cocrystal of cannabinoid. The term "multiple unit dosage form" defines a dosage from which consists of more than one unit which contains the effective amount of the cocrystal of cannabinoid. Usually the multiple unit dosage forms are based on subunits such as granules, pellets or minitablets. They are usually delivered in hard capsules or transformed into tablets. Thus, it is also part of the invention a unit dosage form which comprises the composition of the present invention. In an embodiment, the unit dosage form which comprises the composition of the present invention is a single unit dosage form. In an embodiment, the unit dosage from which comprises the composition of the present invention is a multiple unit dosage form. In an embodiment, the solid composition is a capsule; particularly a hard capsule. In an embodiment, the solid composition is a tablet; particularly a direct-compressed tablet or a dry-granulation tablet.

In an embodiment, the pharmaceutical or cosmetic solid composition is an immediate release composition. In an embodiment, the pharmaceutical or cosmetic solid composition is a modified release composition. The term "modified release" refers to a composition in which the rate of release of the cannabinoid from the composition after administration has been changed according to the particular circumstances surrounding the case and the particular condition being treated. In other words, it is a composition exhibiting a different release of the cannabinoid than that of a conventional immediate release composition administered by the same route. For the purpose of the invention, the term "modified release" includes a controlled release, a sustained release, a prolonged release or an extended release.

The pharmaceutical or cosmetic composition as defined above comprise appropriate excipients or carriers including, but not limited to, binders, fillers, disintegrants, glidants, lubricants or their mixtures. Additionally, the compositions of the present invention may contain other ingredients, such as colorants, and other components known in the state of the art for use in pharmaceutical and cosmetic compositions.

The term "binder" refers to any pharmaceutically acceptable compound having binding properties. Materials commonly used as binders include povidone such as polyvinylpyrrolidone, methylcellulose polymers, hydroxyethyl cellulose, hydroxypropyl cellulose, L-hydroxypropyl cellulose (low substituted), hydroxypropylmethyl cellulose (HPMC), sodium carboxymethyl cellulose, carboxymethylene, carboxymethylhydroxyethyl cellulose and other cellulose derivatives, starches or modified starches, gelatine, sugars such as sucrose, glucose and sorbitol, gums such as sum arabic, tragacanth, agar and carragenenan; and mixture thereof. In an embodiment, the composition of the invention is one wherein the pharmaceutically or cosmetically acceptable excipients or carriers comprise one or more binder; preferably comprise polyvinylpyrrolidone. In an embodiment, the composition of the invention is one wherein the pharmaceutically or cosmetically acceptable excipients or carriers comprise one or more binder in an amount from 1% to 10% by weight, preferably from 1% to 6% by weight, more preferably from 1% to 3% by weight of the composition.

The terms "filler" and "diluent" have the same meaning and are used interchangeably. They refer to any pharmaceutically acceptable excipient or carrier (material) that fill out the size of a composition, making it practical to produce and convenient for the consumer to use. Materials commonly used as filler include calcium carbonate, calcium phosphate, dibasic calcium phosphate, tribasic calcium sulfate, calcium carboxymethyl cellulose, cellulose, cellulose products such as microcrystalline cellulose and its salts, dextrin derivatives, dextrin, dextrose, fructose, lactitol, lactose, starches or modified starches, magnesium carbonate, magnesium oxide, maltitol, maltodextrins, maltose, mannitol, sorbitol, starch, sucrose, sugar, xylitol, erythritol and mixtures thereof. In an embodiment, the composition of the invention is one wherein the pharmaceutically or cosmetically acceptable excipients or carriers comprises one or more filler; preferably comprises microcrystalline cellulose and its salts.

The term "disintegrant" refers to a substance which helps the composition break up once ingested. Materials commonly used as a disintegrant are, but not limited to, cross linked polyvinylpyrolidone; starches such as maize starch and dried sodium starch glycolate; gums such as maize starch and dried sodium starch glycolate; gums such as alginic acid, sodium alginate, guar gum; croscarmellose sodium; low-substituted hydroxypropyl cellulose and mixtures thereof. In an embodiment, the composition of the invention is one wherein the pharmaceutically or cosmetically acceptable excipients or carriers comprises one or more disintegrants; preferably comprises croscarmellose sodium.

The term "glidant" refers to a substance which improves the flow characteristics of powder mixtures in the dry state. Materials commonly used as a glidant include magnesium stearate, colloidal silicon dioxide or talc. In an embodiment, the composition of the invention is one wherein the pharmaceutically or cosmetically acceptable excipients or carriers comprises one or more glidant; preferably comprises magnesium stearate, talc or mixture thereof.

The term "lubricant" refers to a substance that prevents composition ingredients from clumping together and from sticking to the tablet punches or capsule filling machine and improves flowability of the composition mixture. Materials commonly used as a lubricant include sodium oleate, sodium stearate, sodium benzoate, sodium stearate, sodium chloride, stearic acid, sodium stearyl fumarate, calcium stearate, magnesium stearate, magnesium lauryl sulfate, sodium stearyl fumarate, sucrose esters or fatty acid, zinc, polyethylene glycol, talc and mixtures thereof. The presence of a lubricant is particularly preferred when the composition is a tablet to improve the tableting process. In an embodiment, the composition of the invention is one wherein the pharmaceutically or cosmetically acceptable excipients or carriers comprises one or more lubricants; preferably comprises magnesium stearate.

The pharmaceutical and cosmetic compositions of the present invention can be prepared according to methods well known in the state of the art. The appropriate excipients and/or carriers, and their amounts, can readily be determined by those skilled in the art according to the type of formulation being prepared.

In an embodiment, the pharmaceutical or cosmetic composition is a tablet. In an embodiment, the pharmaceutical or cosmetic composition is a direct-compressed tablet. In an embodiment, the pharmaceutical or cosmetic direct-compressed tablet comprises: from 1% to 80% by weight of one or more of the cocrystal of the cannabinoid; from 20% to 99% by weight of one or more fillers; and from 0.25% to 10% by weight of one or more glidants; being the sum of components of the composition of 100% by weight.

In an embodiment, the pharmaceutical or cosmetic direct-compressed tablet comprises: from 9% to 40% by weight of one or more of the cocrystal of the cannabinoid; from 50% to 90% by weight of microcrystalline cellulose; and from 0.25% to 2% by weight of magnesium stearate; being the sum of components of the composition of 100% by weight.

The process for the preparation of a direct-compressed tablet comprises only blending the ingredients in an appropriate order without granulation and avoids the use of organic solvents, water and/or high temperatures, wherein the cannabinoid could degrade.

In an embodiment, the pharmaceutical or cosmetic composition is a dry-granulation tablet. In an embodiment, the pharmaceutical or cosmetic dry-granulation tablet comprises: from 1% to 80% by weight of one or more of the cocrystal of the cannabinoid; from 20% to 99% by weight of one or more fillers; from 1% to 15% by weight of one or more disintegrants; from 0.25% to 10% by weight of one or more glidants; and from 0.25% to 10% by weight of one or more lubricant; being the sum of components of the composition of 100% by weight.

In an embodiment, the pharmaceutical or cosmetic dry-granulation tablet comprises: from 9% to 40% by weight of one or more of the cocrystal of the cannabinoid; from 50% to 90% by weight of one or more fillers; from 1% to 6% by weight of one or more disintegrants; from 0.25% to 4% by weight of one or more glidants; and from 0.25% to 2% by weight of one or more lubricant; being the sum of components of the composition of 100% by weight.

In an embodiment, the pharmaceutical or cosmetic dry-granulation tablet comprises: from 30% to 40% by weight of one or more of the cocrystal of the cannabinoid; from 50% to 60% by weight of microcrystalline cellulose; from 2% to 4% by weight of croscarmellose sodium; from 0.5% to 2% by weight of magnesium stearate; and from 1% to 4% by weight of talc; being the sum of components of the composition of 100% by weight.

The process for the preparation of a dry-granulation tablet comprises preparing a blend of the ingredients by mixing the ingredients in an appropriate order; compacting the blend thus obtained to form compacted forms (i.e. preforms or slugs); sieving the compacted forms to obtain granules; and finally compressing the obtained granules into tablets.

The manufacturing conditions of the process for compressing into tablets as defined above can readily be determined by those skilled in the art. In an embodiment, the compressing step is performed at a compression force to obtain tablets having a hardness from 50N to 150N; particularly from 70N to 100N; more particularly about 80N to obtain tablets having a weight about 200 to 600 mg.

Both processes disclosed above for the preparation of the solid compositions of the invention in form of tablets comprising a cocrystal of a cannabinoid are advantageous because avoid the use of solvents; particularly organic solvents and are performed under mild manufacturing conditions. Therefore, these processes are especially advantageous for avoiding the degradation of the cannabinoid during the manufacturing of the solid composition and also during its storage.

In an embodiment, the pharmaceutical or cosmetic composition is a capsule. In an embodiment, the pharmaceutical or cosmetic composition is a hard capsule. In an embodiment, the pharmaceutical or cosmetic composition is a hard capsule selected from hard gelatine capsule and hard hydroxypropylmethyl cellulose (HMPC) capsule.

In an embodiment, the pharmaceutical or cosmetic capsule comprising comprises: from 1% to 80% by weight of one or more of the cocrystal of the cannabinoid; from 20% to 99% by weight of one or more fillers; and from 0.25% to 10% by weight of one or more glidants; being the sum of components of the composition of 100% by weight.

In an embodiment, the pharmaceutical or cosmetic capsule comprising comprises: from 10% to 40% by weight of one or more of the cocrystal of the cannabinoid; from 55% to 90% by weight of one or more fillers; and from 0.25% to 10% by weight of one or more glidants; being the sum of components of the composition of 100% by weight.

In an embodiment, the pharmaceutical or cosmetic capsule comprising comprises: from 10% to 40% by weight of one or more of the cocrystal of the cannabinoid; from 60% to 90% by weight microcrystalline cellulose; and from 0.25% to 2% by weight magnesium stearate; being the sum of components of the composition of 100% by weight.

The capsules as defined above can be prepared by any capsule filling method known in the state of the art. Thus, a process for preparing the capsules comprises: (a) preparing a blend of the ingredients by mixing the ingredients in an appropriate order; (b) filling the pharmaceutical capsule with the blend obtained in step (a); and (c) sealing the pharmaceutical capsule.

In an embodiment, the pharmaceutical or cosmetic composition is a "chewable" composition. The term chewable" refers to a composition that breaks and chews in between the teeth before ingestion. Commonly, chewable compositions comprise a gum core, optionally coated. The core often comprises an insoluble gum selected from the group consisting of fillers, waxes, antioxidants, sweeteners and flavouring agents. In an embodiment, the pharmaceutical or cosmetic composition is a "chewable" tablet.

In an embodiment, the solid composition is a "food supplement" comprising the cocrystal of the cannabinoid and an "edible acceptable coformer" together with one or more "edible acceptable excipients or carriers". The terms "dietary supplement", "food supplement" or "nutritional supplement" as used herein interchangeably refers to a preparation intended to supplement the diet and provide nutrients, such as vitamins, minerals, fiber, fatty acids, or amino acids, that may be missing or may not be consumed in sufficient quantity in a person's diet. The term "edible" refers to a coformer, excipient or carrier which can be consumed by humans or animals without significant deleterious health consequences. Suitable food supplement can be fried or not, frozen or not, low fat or not, marinated, battered, chilled, dehydrated, instant, canned, reconstituted, retorted or preserve product. Examples of food supplement for the present invention include, without limitation: a seasonings or condiment, such as a stock, a savoury cube, a powder mix; a meat-based product, such as a poultry, beef or pork based product, a seafood, surimi, or a fish sausage; a dehydrated, instant, reconstituted soup, such as a clear soup, a cream soup, a chicken or beef soup or a vegetable soup; a carbohydrate-based product, such as instant noodles, rice, pasta, potatoes flakes or fried, noodles, pizza, tortillas or wraps; a dairy or fat product, such as a spread, a cheese, or regular or low fat margarine, a butter/margarine blend, a butter, a peanut butter, a shortening, a processed and flavoured cheese; a savoury product, such as a snack, a biscuit (e.g. chips or crisps) or an egg product, a potato/tortilla chip, a microwave popcorn, nuts, a bretzel, a rice cake, or a rice cracker; an imitation products, such as a dairy (e.g a reformed cheese made from oils, fats and thickeners) or seafood or meat (e.g. a vegetarian meat replacer, veggie burgers) analogue; or a pet or animal food (i.e. feed); amongst others.

In an embodiment, the solid composition is a "smoking composition" comprising the cocrystal of the cannabinoid and a "smoking acceptable coformer" together with one or more "smoking acceptable excipients or carriers". The term "smoking composition" is intended to include cigarettes, cigars and pipes. In particular, the smoking composition can be a traditional or non-traditional lit-end cigarette comprising a tobacco rod and a filter attached thereto. Non-traditional cigarettes include, but are not limited to, cigarettes for electrical smoking systems.

In an embodiment, the solid composition is a non-supported composition. The term "non-supported" refers to a composition wherein the cannabinoid is not absorbed in or adsorbed on the surface of a solid support.

The term "cocrystal" refers herein to a crystalline entity with at least two different components (also named "coformers") constituting the unit cell at room temperature (20-25° C.) and interacting by weak interactions. Thus, in a cocrystal, one component crystallizes with one or more neutral components. The cocrystals may include one or more solvent molecules in the crystal lattice. In other words, the term cocrystal refers to solids that are crystalline single-phase materials composed of two or more different molecular and/or ionic compounds generally in a stoichiometric ratio which are neither solvates nor simple salts (cf. Indian J. Pharm. Sci. 2017, vol. 79(6), pp. 858-871).

In an embodiment, the solid composition comprises a cocrystal having a particle size from 50 μm to 250 μm; particularly from 100 μm to 200 μm. In an embodiment, the solid composition comprises a cocrystal having a D50 from 50 μm to 250 μm; particularly from 100 μm to 200 μm. These particle size allows preparing the solid composition of the present invention by simple, cost-effective and industrial scalable process without compromising neither the stability of the cannabinoids in the composition nor the own solid composition stability and uniformity of the solid composition. The term "particle size" refers to the size of the cocrystal measured in μm. The measurement was performed with an appropriate apparatus by conventional analytical techniques such as, for example, microscopic determination utilizing a scanning electron microscope (SEM). In the present invention the particle size was measured by a Mastersizer 2000 particle size analyzer.

Such apparatus uses a technique of laser diffraction to measure the size of particles. It operates by measuring the intensity of light scattered, as a laser beam passes through a dispersed particles sample. This data is then analyzed using the general purpose model to calculate the size of the particles that created the scattering pattern, assuming a spherical particle shape. The terms "particle size distribution" or "PSD" have the same meaning and are used interchangeably. They refer to the percentage of the cocrystals within a certain size range. The term "D50" refers to the value of particle size distribution where at least 50% of the cocrystals have a size less or equal to the given value.

The term "cannabinoid" refers to the class of chemical compounds acting with various affinities on the endogenous cannabinoid receptors (CB1 and CB2). This group include the endocannabinoids (produced naturally by humans and animals), phytocannabinoids (found in Cannabis and some other plants), and synthetic cannabinoids (manufactured totally or partially by an artificial route), the most notable of which are THC and CBD. Cannabinoid compounds are characterized by having a poor oral bioavailability, particularly THC and CBD. Cannabinoids are highly lipophilic and therefore are poorly soluble ex-vivo and in-vivo. This fact in combination with certain pre-systemic events at the gastro intestinal (GI) tract and first pass metabolism, also contribute to their poor bioavailability.

In an embodiment, the solid composition comprises a cocrystal of a cannabinoid which is an oily or a gum at room temperature. The term "room temperature" refers to a temperature of the environment, without heating or cooling, and is generally comprised from 20° C. to 25° C.

In an embodiment, the solid composition comprises a cocrystal of a cannabinoid wherein the cannabinoid is obtainable by an extractive process from plants of the genus Cannabis, such as Cannabis indica and Cannabis sativa. In an embodiment, the solid composition comprises a cocrystal of a cannabinoid wherein the cannabinoid is obtainable by a totally-synthetic or a semi-synthetic process.

In an embodiment, the solid composition comprises one or more acceptable excipients or carriers and a cocrystal wherein the cannabinoid is selected from the group consisting of tetrahydrocannabinol (THC), cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), delta8-tetrahydrocannabinol (delta8-THC) or isoforms, derivatives, precursors, metabolites thereof; the combinations being of any two or more of the listed cannabinoids.

In an embodiment, the solid composition comprises a cocrystal wherein the cannabinoid is selected from the group consisting of tetrahydrocannabinol (THC), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), delta8-tetrahydrocannabinol (delta8-THC) or isoforms, derivatives, precursors, metabolites thereof; the combinations being of any two or more of the listed cannabinoids.

In an embodiment, the solid composition comprises a cocrystal wherein the cannabinoid is selected from the group consisting of Tetrahydrocannabinol (THC), Cannabidiol (CBD), delta8-THC, Cannabinol (CBN), Cannabigerol (CBG), Cannabidivarin (CBDV) and a mixture thereof. In an embodiment, the solid composition comprises a cocrystal wherein the cannabinoid is selected from the group consisting of Tetrahydrocannabinol (THC), Cannabidiol (CBD), Cannabinol (CBN), Cannabigerol (CBG), Cannabidivarin (CBDV) and a mixture thereof. In an embodiment, the solid composition comprises a cocrystal wherein the cannabinoid is selected from the group consisting of tetrahydrocannabinol (THC), cannabidiol (CBD), delta8-THC and a mixture thereof. In an embodiment, the solid composition comprises a cocrystal wherein the cannabinoid is selected from the group consisting of tetrahydrocannabinol (THC), cannabidiol (CBD) and a mixture thereof. In an embodiment, the solid composition comprises a cocrystal wherein the cannabinoid is selected from the group consisting of tetrahydrocannabinoid (THC), delta8-tetrahydrocannabinol (delta8-THC) and a mixture thereof. In an embodiment, the solid composition comprises a cocrystal wherein the cannabinoid is selected from the group consisting of tetrahydrocannabinoid (THC).

In a particular embodiment, the solid composition comprises a cocrystal wherein the cannabinoid is CBD. Cannabidiol (abbreviated as (−)-CBD or CBD)) is the International Nonpropietary Name of 2-[(1R,6R)-6-isopropenyl-3-methylcyclohex-2-en-1-yl]-5-pentylbenzene-1,3-diol having the CAS number 13956-29-1. The structure of Cannabidiol corresponds to the formula (I):

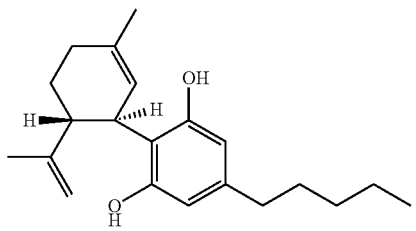

(I)

In a particular embodiment, the solid composition comprises a cocrystal wherein the cannabinoid is THC. Tetrahydrocannabinol or Trans+)-$\Delta^9$-tetrahydrocannabinol (abbreviated as $\Delta^9$-THC, (−)-$\Delta^9$-THC, trans-(−)-$\Delta^9$-THC or THC) is the International Nonpropietary Name of (−)-(6aR,10aR)-6,6,9-trimethyl-3-pentyl-6a,7,8,10a-tetrahydro-6H-benzo[c]chromen-1-ol having the CAS number 1972-08-3. The structure of $\Delta^9$-THC corresponds to the formula (II):

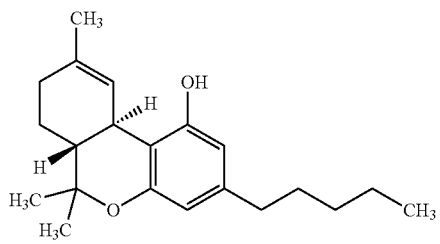

(II)

In a particular embodiment, the solid composition comprises a cocrystal wherein the cannabinoid is delta8-THC. (−)-Delta8-trans-Tetrahydrocannabinol (abbreviated as $\Delta^8$-THC, (−)-$\Delta^8$-THC, trans-(−)-$\Delta^8$-THC or delta8-THC) is the International Nonpropietary Name of (6aR,10aR)-6,6,9-Trimethyl-3-pentyl-6a,7,10,10a-tetrahydro-6H-benzo[c]chromen-1-ol having the CAS number 5957-75-5. The structure of $\Delta^8$-THC corresponds to the formula (III):

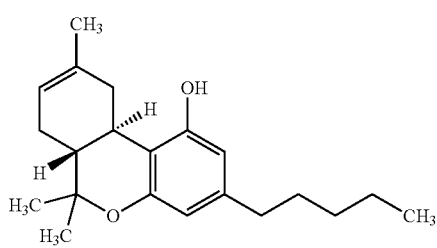

(III)

In a particular embodiment, the solid composition comprises a cocrystal wherein the cannabinoid is CBN. Cannabinol (abbreviated as CBN) is the International Nonpropietary Name of 6,6,9-trimethyl-3-pentylbenzo[c]chromen-1-ol having the CAS number 521-35-7. The structure of Cannabinol corresponds to the formula (IV):

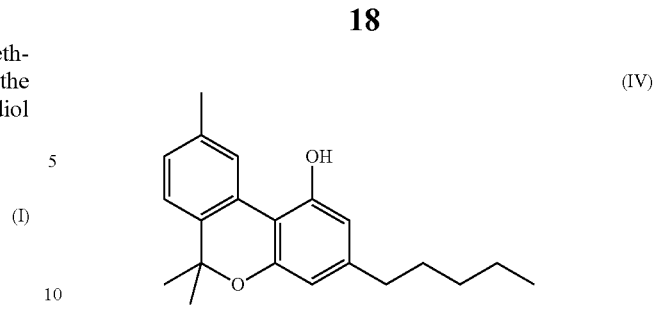

(IV)

In a particular embodiment, the solid composition comprises a cocrystal wherein the cannabinoid is CBG. Cannabigerol (abbreviated as CBG) is the International Nonpropietary Name of 2-[(2E)-3,7-dimethylocta-2,6-dien-1-yl]-5-pentylbenzene-1,3-diol having the CAS number 25654-31-3. The structure of corresponds to the formula (V):

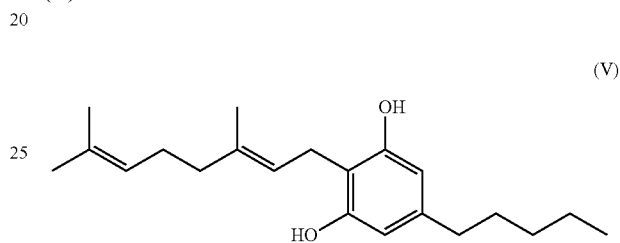

(V)

In a particular embodiment, the solid composition comprises a cocrystal wherein the cannabinoid is CBDV. Cannabidivarin (abbreviated as CBDV) is the International Nonpropietary Name of 2-((1R,6R)-3-methyl-6-(prop-1-en-2-yl) cyclohex-2-en-1-yl)-5-propylbenzene-1,3-diol having the CAS number 24274-48-4. The structure of corresponds to the formula (VI):

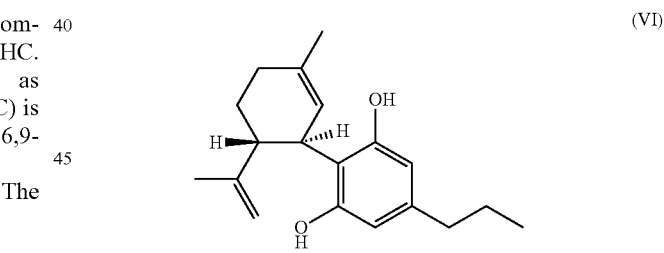

(VI)

As it is mentioned above, the solid composition comprises a zwitterion. The term "zwitterion" refers to a molecule having separate and distinct positively and negatively charged moieties resident on the same molecule with a net charge of zero. Thus, this coformer comprises one or more charged functional groups. Without being bound to any theory, the presence of one or more protonable group in the coformer allows increasing the solubility of the cannabinoid after its dissociation from the cocrystal. Thus, the cocrystal of the invention having one or more protonable groups allows modifying the solubility of the cannabinoid at physiological conditions. It means that the cocrystals of the present invention which comprises an aqueous soluble coformers (zwitterions) can generate a solubility improvement by formation of a complex in solution, by dissociation of the cocrystal (if the re-precipitation is not immediate) or by re-precipitation of a more soluble crystalline form.

In an embodiment, the zwitterion comprises a positively charged nitrogen atom and a negatively charged group distal to the positively charged nitrogen atom on the organic zwitterion such that there is a separation by at least one carbon atom; preferably from 1 to 4 carbon atoms. In an embodiment, the coformer is an amino acid.

In an embodiment, the solid composition comprises a cocrystal wherein the coformer is selected from the group consisting of L-proline, betaine, L-carnitine, D-proline, and DL-proline. Particularly selected from L-proline, D-proline and DL-proline. Particularly, L-proline, betaine and L-carnitine.

In an embodiment, the solid composition comprises a cocrystal wherein the cannabinoid is CBD, THC, delta8-THC, CBN, CBG or CBVD and the coformer is selected from the group consisting of L-proline, betaine, L-carnitine, D-proline and DL-proline. Particularly selected from L-proline, D-proline, betaine and L-carnitine.

In an embodiment, the solid composition comprises a cocrystal wherein the cannabinoid is THC or delta8-THC, and the coformer is selected from the group consisting of L-proline, D-proline and DL-proline. Particularly selected from L-proline, D-proline; more particularly L-proline.

In an embodiment, the solid composition comprises a cocrystal wherein the cannabinoid is CBD, CBDV, CBG or CBN, and the coformer is selected from the group consisting of L-proline, D-proline and DL-proline, L-Carnitine and betaine. Particularly selected from L-proline, D-proline, L-Carnitine and betaine; more particularly betaine.

In an embodiment, the solid composition comprises a cocrystal Form I, II, III, IV, V, VII, VIII, IX, X, XI, XII, XIII, XIV, XV, XVI, XVII, XVIII or XIX as defined above in the present invention. In an embodiment, the solid composition comprises a cocrystal Form I, II, III, IV, V, VII, VIII, IX and X as defined above in the present invention. Particularly, the solid composition comprises a cocrystal Form I, VII, IX, XI, XII, XVI, XVII, XVIII and XIX. Particularly, the solid composition comprises a cocrystal Form I, VII, IX, XI and XII. Particularly, the solid composition comprises a cocrystal Form I, VII and IX, The second aspect of the invention refers to a cocrystal of a cannabinoid selected from THC, delta8-THC, CBN, CBG, CBDV and a zwitterion coformer. In an embodiment, the cocrystal of the invention is a cocrystal wherein the coformer is selected from the group consisting of L-proline, betaine, L-carnitine, D-proline and DL-proline. The coformer L-proline, L-carnitine and betaine; more particularly L-proline, are especially advantageous because it is useful for both the purification of cannabinoid after being dissociated from the cocrystal and for being used as a medicament forming part of a pharmaceutical composition due to the fact that the L-proline, L-carnitine and betaine are classified as Substance Added to Food by the FDA. Particularly, the invention refers to a cocrystal Form VII, VIII, IX, XI, XII, XIII, XVI, XVII, XVIII and XIX; more particularly VII, IX, XI, XIII, XIX. In an embodiment, the cocrystal of the second aspect of the invention is a cocrystal of a cannabinoid selected from THC and delta8-THC and a zwitterion coformer. In an embodiment, the cocrystal of the invention is a cocrystal of THC or delta8-THC wherein the coformer is selected from the group consisting of L-proline, D-proline. Particularly, the cocrystal of the present invention refers to a cocrystal Form VII, VIII, IX and X; more particularly VII and IX.

In an embodiment, the solid composition comprises a cocrystal of 2-[(1R,6R)-6-isopropenyl-3-methylcyclohex-2-en-1-yl]-5-pentylbenzene-1,3-diol (CBD) and a coformer selected from the group consisting of L-proline, betaine, L-carnitine, D-proline and DL-proline. Particularly, the solid composition comprises the cocrystal of the present invention refers to a cocrystal Form I, II, III, IV and V.

In an embodiment, the cocrystal is a cocrystal of CBD and L-proline, also named Form I. For the purposes of the invention, L-proline is the International Nonproprietary Name (INN) of (S)-2-pyrrolidinecarboxylic acid, and has the CAS No. 147-85-3. The structure of L-proline is the following:

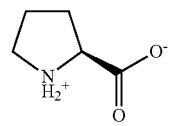

In an embodiment, the cocrystal Form I is characterized by having an X-ray powder diffractogram that comprises characteristic peaks at 5.8, 11.1 and 15.8±0.3 degrees 2 theta at a Cu—K$_\alpha$ radiation, λ=1.5406 Å. In an embodiment, the cocrystal Form I is characterized by having an X-ray powder diffractogram that comprises further characteristic peaks at 7.4, 11.4 and 21.2±0.3 degrees 2 theta at a Cu—K$_\alpha$ radiation, λ=1.5406 Å.

More specifically, the cocrystal Form I is characterized by exhibiting in the X-ray powder diffractogram a pattern of peaks, expressed in 2 theta units in degrees, 2θ (°), which is shown in Table 1.

TABLE 1

List of selected peaks (only peaks with relative intensity greater than or equal to 1% are indicated):

| Pos. [°2θ] | d-spacing [Å] | Rel. Int. [%] |
|---|---|---|
| 5.3 | 16.8 | 100 |
| 5.8 | 15.3 | 63 |
| 7.4 | 12.0 | 17 |
| 9.4 | 9.4 | 16 |
| 10.6 | 8.3 | 10 |
| 11.1 | 7.9 | 40 |
| 11.4 | 7.7 | 44 |
| 11.7 | 7.6 | 40 |
| 12.3 | 7.2 | 61 |
| 14.8 | 6.0 | 9 |
| 15.3 | 5.8 | 26 |
| 15.8 | 5.6 | 42 |
| 16.4 | 5.4 | 18 |
| 17.4 | 5.1 | 10 |
| 18.6 | 4.8 | 41 |
| 18.9 | 4.7 | 37 |
| 19.4 | 4.6 | 32 |
| 20.0 | 4.4 | 6 |
| 21.2 | 4.2 | 38 |
| 22.3 | 4.0 | 3 |
| 23.0 | 3.9 | 21 |
| 23.5 | 3.8 | 8 |
| 24.5 | 3.6 | 14 |
| 25.9 | 3.4 | 10 |
| 26.4 | 3.4 | 8 |
| 27.5 | 3.2 | 6 |
| 29.0 | 3.1 | 1 |
| 30.1 | 3.0 | 2 |
| 35.6 | 2.5 | 2 |

The cocrystal Form I may be further characterized by an X-ray diffractogram as in FIG. 1.

The cocrystal Form I may also be further characterized by the following $^1$H NMR spectrum (CD$_3$OD, 400 MHz, δ): 6.08 (s, 2H, ArH); 5.29 (s, 1H); 4.45 (d, 2H, J=14.4 Hz);

3.98-3.90 (m, 2H); 3.42-3.35 (m, 1H); 3.26-3.19 (m, 1H); 2.94-2.87 (m, 1H); 2.38 (t, 2H, J=7.2 Hz); 2.34-2.25 (m, 1H); 2.24-2.08 (m, 2H); 2.04-1.91 (m, 3H); 1.76-1.71 (m, 2H); 1.68 (s, 3H); 1.64 (s, 3H); 1.58-1.51 (m, 2H); 1.39-1.24 (m, 4H); 0.90 (t, 3H, J=7.2 Hz).

Figure 11:
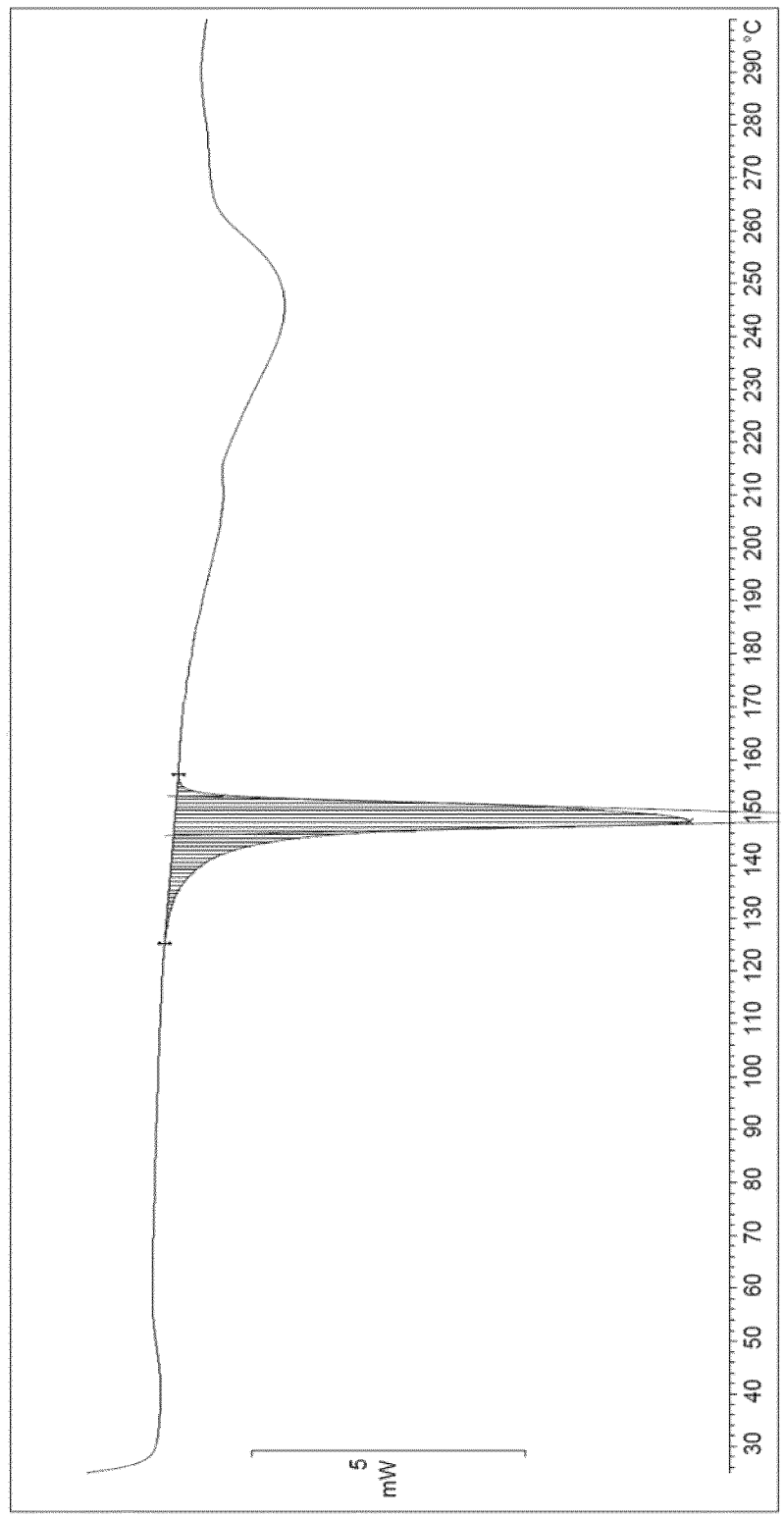
FIG. 11 shows the DSC of cocrystal Form I. The spectrum expresses the heat flow (mW/mg) versus temperature (° C.).

The cocrystal Form I may also be further characterized by DSC (differential scanning calorimetry) analysis as shown in FIG. 11. The DSC analysis of cocrystal Form I shows an endothermic event with an onset at 145.3° C. which corresponds to the melting point of cocrystal Form I followed by endothermic peaks possibly due to degradation (decomposition) events. The cocrystal Form I may also be further characterized by having a melting range of 142-152° C.

The cocrystal Form I may also be further characterized by thermogravimetric analysis (TGA). The TG analysis of cocrystal Form I shows a weight loss between 26.7° C. and 61.5° C. that corresponds to the loss of about 0.05 water molecules (0.20%, where the calculated value corresponding to one water molecule is 4.0%). Therefore, TGA confirms that cocrystal Form I is not a hydrate. The TGA of cocrystal Form I shows no significant weight loss before its melting (cf. FIG. 2).

The cocrystal of Form I prepared from pure commercial CBD (98.8% a/a HPLC—method 1) has purity equal to or higher than 99% a/a measured by HPLC (method 1). It is worth noting that the coformer is not detected in the HPLC conditions used in this analysis (method 1).

The cocrystal Form I is in a molar ratio 1:1 (CBD:L-proline).

In an embodiment, the cocrystal is a cocrystal of CBD and betaine, also named Form II. For the purposes of the invention, betaine is the International Nonproprietary Name (INN) of 2-trimethylammonioacetate, and has the CAS No. 107-43-7. The structure of betaine is the following:

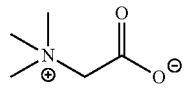

In an embodiment, the cocrystal Form II is characterized by having an X-ray powder diffractogram that comprises characteristic peaks at 9.1, 10.7 and 18.4±0.3 degrees 2 theta at a Cu—K$_\alpha$ radiation, λ=1.5406 Å. In an embodiment, the cocrystal Form II is characterized by having an X-ray powder diffractogram that comprises further characteristic peaks at 5.3 and 13.0±0.3 degrees 2 theta at a Cu—K$_\alpha$ radiation, λ=1.5406 Å.

More specifically, the cocrystal Form II is characterized by exhibiting in the X-ray powder diffractogram a pattern of peaks, expressed in 2 theta units in degrees, 2θ (°), which is shown in Table 2.

TABLE 2

List of selected peaks (only peaks with relative intensity greater than or equal to 1% are indicated):

| Pos. [°2θ] | d-spacing [Å] | Rel. Int. [%] |
|---|---|---|
| 5.3 | 16.6 | 100 |
| 9.1 | 9.7 | 46 |
| 10.7 | 8.3 | 11 |
| 12.0 | 7.4 | 4 |
| 12.4 | 7.2 | 5 |
| 13.0 | 6.8 | 69 |
| 14.0 | 6.3 | 6 |
| 14.4 | 6.1 | 7 |
| 15.2 | 5.8 | 13 |
| 16.1 | 5.5 | 4 |
| 16.6 | 5.3 | 38 |
| 16.9 | 5.3 | 12 |
| 17.1 | 5.2 | 7 |
| 17.7 | 5.0 | 18 |
| 18.4 | 4.8 | 77 |
| 19.0 | 4.7 | 5 |
| 20.0 | 4.4 | 6 |
| 20.5 | 4.3 | 1 |
| 21.0 | 4.2 | 13 |
| 21.6 | 4.1 | 19 |
| 21.9 | 4.0 | 6 |
| 23.5 | 3.8 | 6 |
| 23.8 | 3.7 | 10 |
| 24.5 | 3.6 | 6 |
| 25.6 | 3.5 | 4 |
| 26.2 | 3.4 | 5 |
| 26.8 | 3.3 | 3 |
| 27.7 | 3.2 | 5 |

Figure 3:
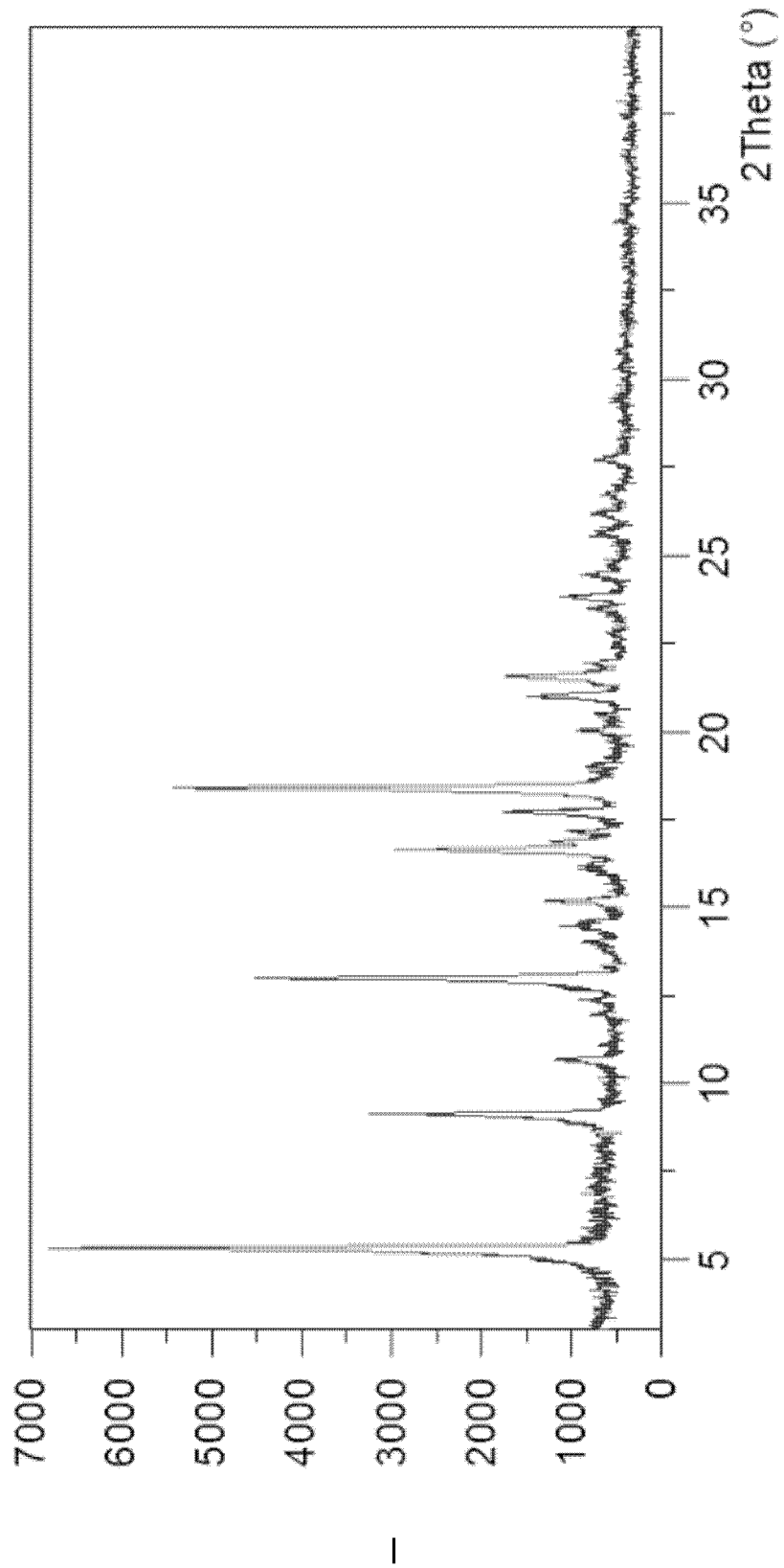
FIG. 3 shows the X-ray powder diffractogram (XRPD) of the cocrystal Form II. The spectrum expresses intensity (I; counts) versus degrees 2 theta (°).

The cocrystal Form II may be further characterized by an X-ray diffractogram as in FIG. 3.

The cocrystal Form II may also be further characterized by the following $^1$H NMR spectrum (CD$_3$OD, 400 MHz, δ): 6.08 (s, 2H, ArH); 5.29 (s, 1H); 4.47-4.43 (m, 2H); 3.95-3.90 (m, 1H); 3.62 (s, 2H); 3.27 (s, 9H); 2.94-2.86 (m, 1H); 2.38 (t, 2H, J=7.2 Hz); 2.25-2.15 (m, 1H); 2.04-1.96 (m, 1H); 1.76-1.71 (m, 2H); 1.68 (s, 3H); 1.64 (s, 3H); 1.59-1.51 (m, 2H); 1.38-1.24 (m, 4H); 0.90 (t, 3H, J=7.2 Hz).

The cocrystal Form II may also be further characterized by DSC (differential scanning calorimetry) analysis. The DSC analysis of cocrystal Form II shows endothermic events with an onset at 32.0° C., 79.2° C., 159.0° C. and 233.0° C.

The cocrystal of Form II prepared from pure commercial CBD (98.8% a/a HPLC—method 1) has a purity equal to or higher than 99% a/a measured by HPLC (method 1). It is worth noting that the coformer is not detected in the HPLC conditions used in this analysis.

The cocrystal Form II is in a molar ratio 1:1 (CBD: betaine).

In an embodiment, the cocrystal is a cocrystal of CBD and L-carnitine, also named Form III. For the purposes of the invention, L-carnitine is the International Nonproprietary Name (INN) of (3R)-3-hydroxy-4-(trimethylammonio)butanoate (also named 3-Hydroxy-4-(trimethylazaniumyl)butanoate) and has the CAS No. 541-15-1. The structure of L-carnitine is the following:

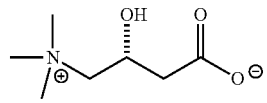

In an embodiment, the cocrystal Form III is characterized by having an X-ray powder diffractogram that comprises characteristic peaks at 6.8, 11.3 and 20.0±0.3 degrees 2 theta at a Cu—K$_\alpha$ radiation, λ=1.5406 Å. In an embodiment, the cocrystal Form III is characterized by having an X-ray powder diffractogram that comprises further characteristic peaks at 12.7, 13.6, and 15.6±0.3 degrees 2 theta at a Cu—K$_\alpha$ radiation, λ=1.5406 Å.

More specifically, the cocrystal Form III is characterized by exhibiting in the X-ray powder diffractogram a pattern of peaks, expressed in 2 theta units in degrees, 2θ (°), which is shown in Table 3.

TABLE 3

List of selected peaks (only peaks with relative intensity greater than or equal to 1% are indicated):

| Pos. [°2θ] | d-spacing [Å] | Rel. Int. [%] |
|---|---|---|
| 6.8 | 13.0 | 100 |
| 8.8 | 10.1 | 26 |
| 10.2 | 8.7 | 15 |
| 11.3 | 7.9 | 44 |
| 11.6 | 7.6 | 22 |
| 11.9 | 7.4 | 11 |
| 12.7 | 7.0 | 17 |
| 13.6 | 6.5 | 33 |
| 13.9 | 6.4 | 34 |
| 14.9 | 6.0 | 5 |
| 15.6 | 5.7 | 35 |
| 16.2 | 5.5 | 70 |
| 17.0 | 5.2 | 13 |
| 17.7 | 5.0 | 29 |
| 17.9 | 5.0 | 18 |
| 19.5 | 4.5 | 30 |
| 20.0 | 4.4 | 42 |
| 21.0 | 4.2 | 51 |
| 22.2 | 4.0 | 33 |
| 22.7 | 3.9 | 11 |
| 24.5 | 3.6 | 26 |
| 28.3 | 3.2 | 5 |
| 28.3 | 3.1 | 7 |
| 29.4 | 3.0 | 7 |
| 30.0 | 3.0 | 6 |

Figure 4:
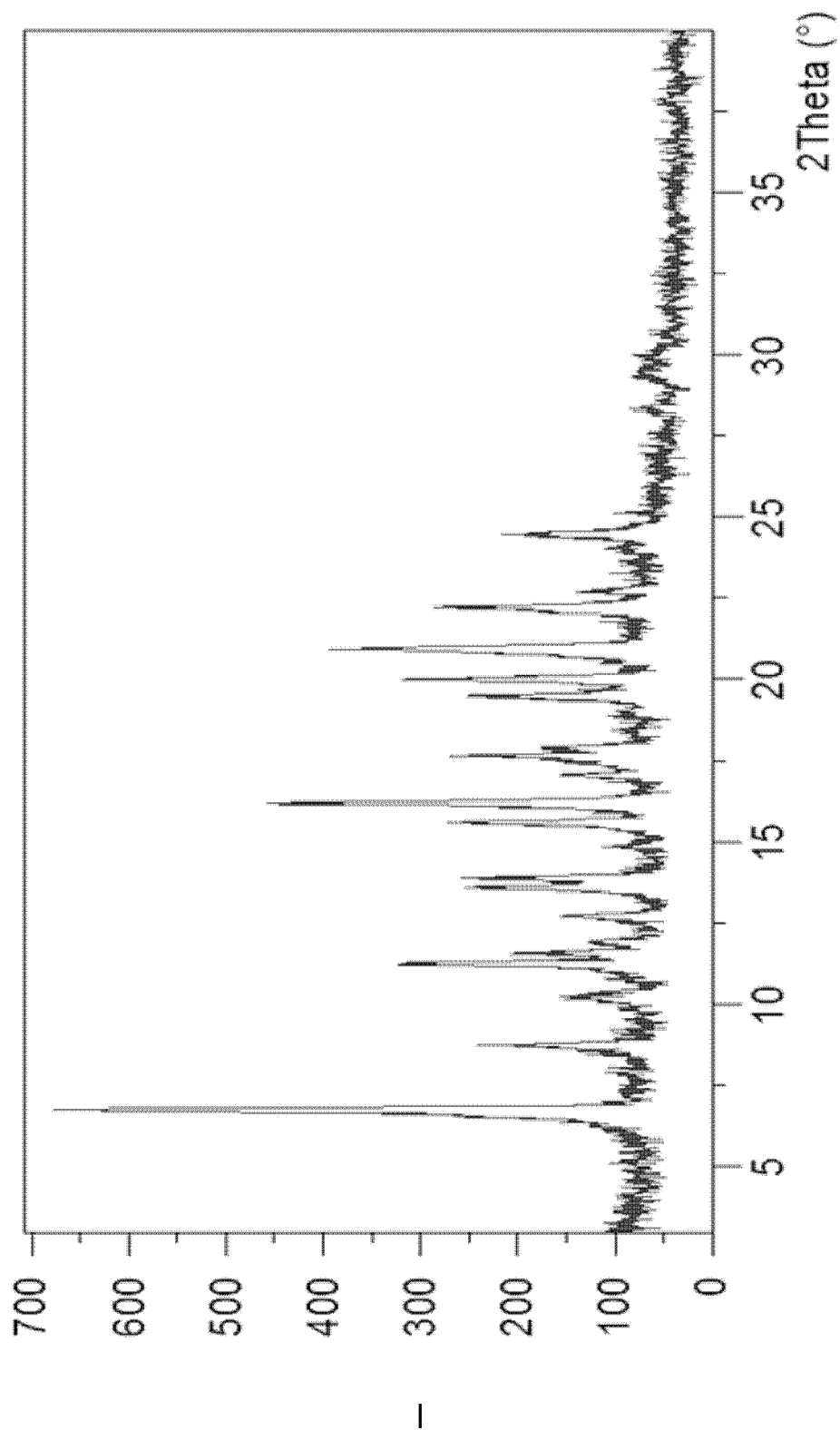
FIG. 4 shows the X-ray powder diffractogram (XRPD) of the cocrystal Form III. The spectrum expresses intensity (I; counts) versus degrees 2 theta (°).

The cocrystal Form III may be further characterized by an X-ray diffractogram as in FIG. 4.

The cocrystal Form III may also be further characterized by the following $^1$H NMR spectrum (CD$_3$OD, 400 MHz, δ): 6.08 (s, 2H, ArH); 5.29 (s, 1H); 4.48-4.42 (m, 4H); 3.95-3.90 (m, 1H); 3.42-3.33 (m, 4H); 3.22 (s, 18H); 2.94-2.88 (m, 1H); 2.40-2.16 (m, 7H); 2.04-1.95 (m, 1H); 1.76-1.71 (m, 2H); 1.68 (s, 3H); 1.64 (s, 3H); 1.58-1.51 (m, 2H); 1.39-1.24 (m, 4H); 0.90 (t, 3H, J=7.2 Hz).

The cocrystal Form III may also be further characterized by DSC (differential scanning calorimetry) analysis. The DSC analysis of cocrystal Form III shows a first endothermic event with an onset at 56.4° C.; a second event with an onset at 112.7° C.; a third event having an onset at 138.7° C. and finally, an endothermic event with an onset at 174.7° C. It was checked that the two first thermal events with an onset at 56.4 and 112.7° C. do not correspond to melting events. The solids obtained after both events correspond after rapid cooling to room temperature to Form III. Therefore, these events should correspond to water desorption and/or dehydration. In case of dehydration, the crystalline form could lead to a dehydrated form with a unit cell size identical to Form III or, it is possible that this dehydrated form converted into Form III before XRPD analysis. The third event with an onset at 138.7° C. corresponds to a solid-solid transformation of Form III to another crystal form. Therefore melting of cocrystal Form III was not observed.

The cocrystal of Form III prepared from pure commercial CBD (98.9% a/a HPLC—method 1) has a purity similar to the starting material. It is worth noting that the coformer is not detected in the HPLC conditions used in this analysis.

The cocrystal Form III is in a molar ratio 1:2 (CBD:L-carnitine).

In an embodiment, the cocrystal is a cocrystal of CBD and D-proline, also named Form IV. For the purposes of the invention, D-proline is the International Nonproprietary Name (INN) of (R)-pyrrolidinecarboxylic acid, and has the CAS No. 344-25-2. The structure of D-proline is the following:

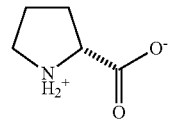

In an embodiment, the cocrystal Form IV is characterized by having an X-ray powder diffractogram that comprises characteristic peaks at 5.7, 11.2 and 15.7±0.3 degrees 2 theta at a Cu—K$_α$ radiation, λ=1.5406 Å. In an embodiment, the cocrystal Form IV is characterized by having an X-ray powder diffractogram that comprises further characteristic peaks at 11.5 and 21.1±0.3 degrees 2 theta at a Cu—K$_α$ radiation, λ=1.5406 Å.

More specifically, the cocrystal Form IV is characterized by exhibiting in the X-ray powder diffractogram a pattern of peaks, expressed in 2 theta units in degrees, 2θ (°), which is shown in Table 4.

TABLE 4

List of selected peaks (only peaks with relative intensity greater than or equal to 1% are indicated):

| Pos. [°2θ] | d-spacing [Å] | Rel. Int. [%] |
|---|---|---|
| 5.2 | 17.0 | 100 |
| 5.7 | 15.4 | 99 |
| 9.4 | 9.4 | 24 |
| 10.3 | 8.6 | 6 |
| 10.6 | 8.3 | 11 |
| 11.2 | 7.9 | 35 |
| 11.5 | 7.7 | 58 |
| 12.4 | 7.1 | 40 |
| 12.7 | 7.0 | 11 |
| 13.7 | 6.5 | 1 |
| 14.7 | 6.0 | 8 |
| 15.3 | 5.8 | 19 |
| 15.7 | 5.6 | 39 |
| 16.3 | 5.4 | 28 |
| 17.3 | 5.1 | 27 |
| 18.6 | 4.8 | 45 |
| 19.2 | 4.6 | 18 |
| 19.4 | 4.6 | 15 |
| 20.2 | 4.4 | 8 |
| 20.7 | 4.3 | 20 |
| 21.1 | 4.2 | 34 |
| 22.2 | 4.0 | 5 |
| 22.7 | 3.9 | 2 |
| 23.2 | 3.8 | 17 |
| 23.9 | 3.7 | 6 |
| 24.6 | 3.6 | 9 |
| 25.6 | 3.5 | 6 |
| 26.2 | 3.4 | 10 |
| 27.6 | 3.2 | 3 |
| 28.3 | 3.2 | 2 |
| 31.3 | 2.9 | 3 |
| 32.1 | 2.8 | 1 |
| 33.1 | 2.7 | 2 |
| 33.9 | 2.6 | 3 |

Figure 7:
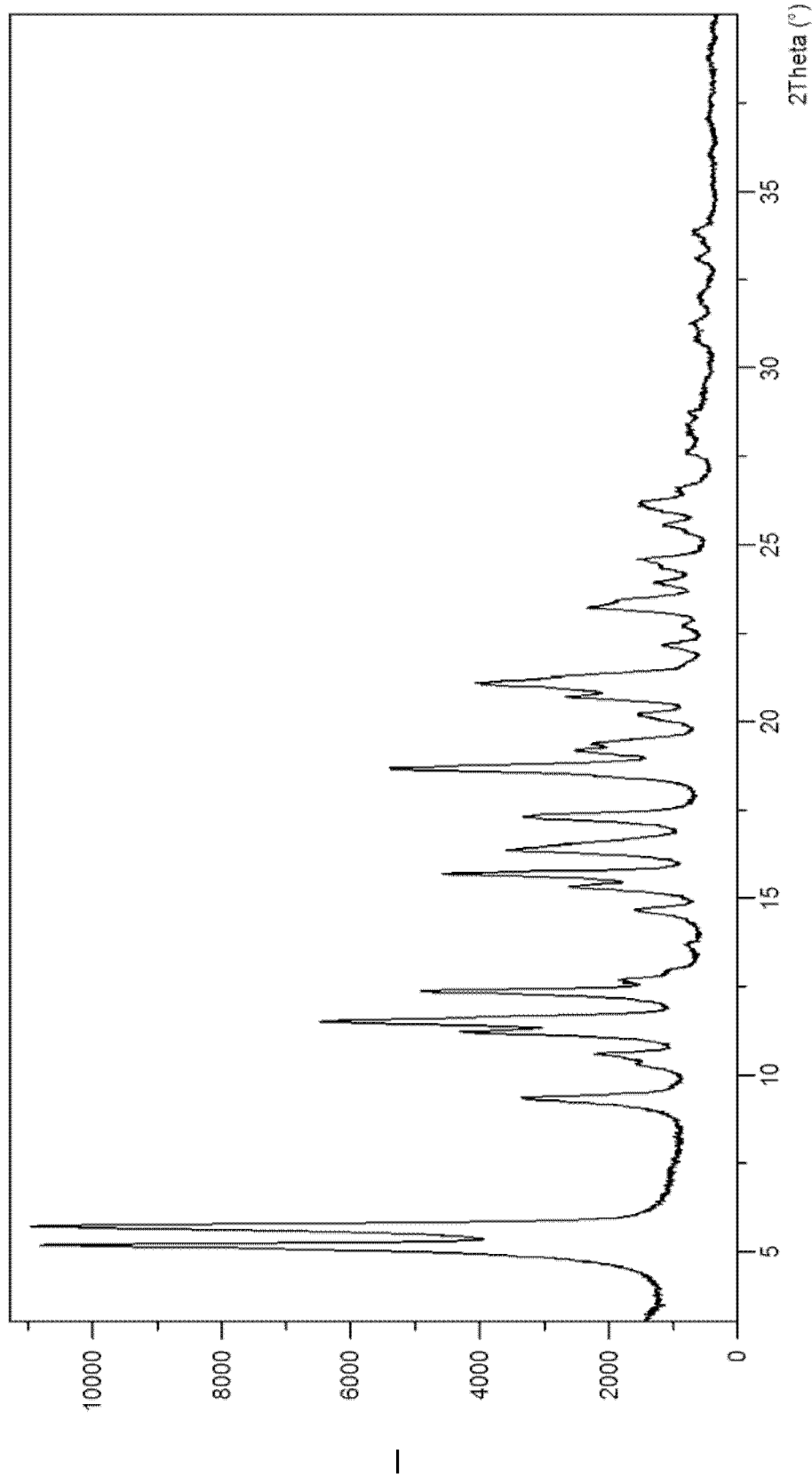
FIG. 7 shows the X-ray powder diffractogram (XRPD) of the cocrystal Form IV. The spectrum expresses intensity (I; counts) versus degrees 2 theta (°).

The cocrystal Form IV may be further characterized by an X-ray diffractogram as in FIG. 7.

The cocrystal Form IV may also be further characterized by the following $^1$H NMR spectrum (CD$_3$OD, 400 MHz, δ): 6.08 (s, 2H, ArH); 5.29 (s, 1H); 4.45 (d, 2H, J=14.2 Hz);

3.99-3.90 (m, 2H); 3.42-3.35 (m, 1H); 3.26-3.20 (m, 1H); 2.94-2.86 (m, 1H); 2.38 (t, 2H, J=7.7 Hz); 2.35-2.25 (m, 1H); 2.24-2.08 (m, 2H); 2.02-1.92 (m, 3H); 1.77-1.71 (m, 2H); 1.68 (s, 3H); 1.64 (s, 3H); 1.59-1.51 (m, 2H); 1.39-1.25 (m, 4H); 0.90 (t, 3H, J=7.0 Hz).

Figure 8:
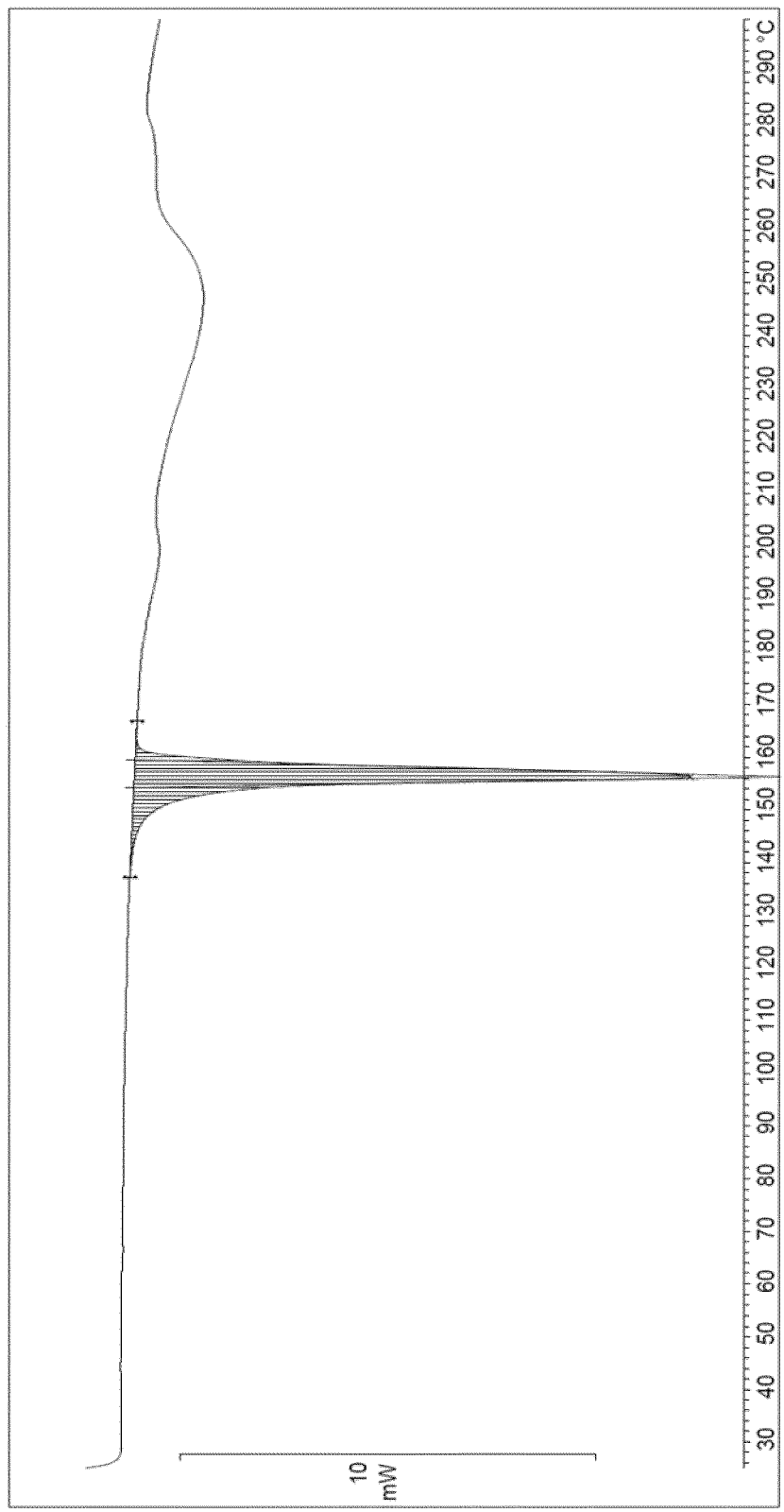
FIG. 8 shows the DSC of cocrystal Form IV. The spectrum expresses the heat flow (mW/mg) versus temperature (° C.).

The cocrystal Form IV may also be further characterized by DSC (differential scanning calorimetry) analysis as shown in FIG. 8. The DSC analysis of cocrystal Form IV shows an endothermic event with an onset at 154.0° C. which corresponds to the melting point of cocrystal Form IV followed by endothermic peaks possibly due to degradation (decomposition) events. The cocrystal Form IV may also be further characterized by having a melting range of 152-160° C.

The cocrystal of Form IV prepared from pure commercial CBD (98.6% a/a HPLC—method 1) has a purity similar to the starting material. It is worth noting that the coformer is not detected in the HPLC conditions used in this analysis.

The cocrystal Form IV is in a molar ratio 1:1 (CBD:D-proline).

In an embodiment, the cocrystal is a cocrystal of CBD and DL-proline, also named Form V. For the purposes of the invention, DL-proline is the International Nonproprietary Name (INN) of (rac)-pyrrolidinecarboxylic acid, and has the CAS No. 609-36-9. The structure of DL-proline is the following:

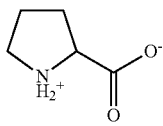

In an embodiment, the cocrystal Form V is characterized by having an X-ray powder diffractogram that comprises characteristic peaks at 5.7, 11.1 and 15.7±0.3 degrees 2 theta at a Cu—$K_\alpha$ radiation, λ=1.5406 Å. In an embodiment, the cocrystal Form V is characterized by having an X-ray powder diffractogram that comprises further characteristic peaks at 11.4 and 21.0±0.3 degrees 2 theta at a Cu—$K_\alpha$ radiation, λ=1.5406 Å.

More specifically, the cocrystal Form V is characterized by exhibiting in the X-ray powder diffractogram a pattern of peaks, expressed in 2 theta units in degrees, 2θ (°), which is shown in Table 5.

TABLE 5

List of selected peaks (only peaks with relative intensity greater than or equal to 1% are indicated):

| Pos. [°2θ] | d-spacing [Å] | Rel. Int. [%] |
|---|---|---|
| 5.2 | 17.1 | 100 |
| 5.7 | 15.5 | 97 |
| 9.4 | 9.5 | 27 |
| 10.6 | 8.4 | 15 |
| 11.1 | 7.9 | 32 |
| 11.4 | 7.7 | 53 |
| 12.3 | 7.2 | 37 |
| 12.6 | 7.0 | 8 |
| 13.6 | 6.5 | 2 |
| 14.7 | 6.0 | 8 |
| 15.3 | 5.8 | 19 |
| 15.7 | 5.6 | 46 |
| 16.3 | 5.4 | 24 |
| 17.3 | 5.1 | 21 |
| 18.6 | 4.8 | 41 |
| 19.1 | 4.6 | 21 |
| 20.1 | 4.4 | 5 |
| 20.7 | 4.3 | 18 |
| 21.0 | 4.2 | 37 |
| 22.2 | 4.0 | 4 |
| 23.1 | 3.8 | 11 |
| 24.4 | 3.7 | 8 |
| 25.5 | 3.5 | 3 |
| 25.9 | 3.4 | 6 |
| 27.5 | 3.2 | 2 |
| 28.5 | 3.1 | 1 |
| 30.8 | 2.9 | 1 |
| 32.0 | 2.8 | 2 |
| 33.1 | 2.7 | 1 |
| 33.8 | 2.7 | 1 |

Figure 9:
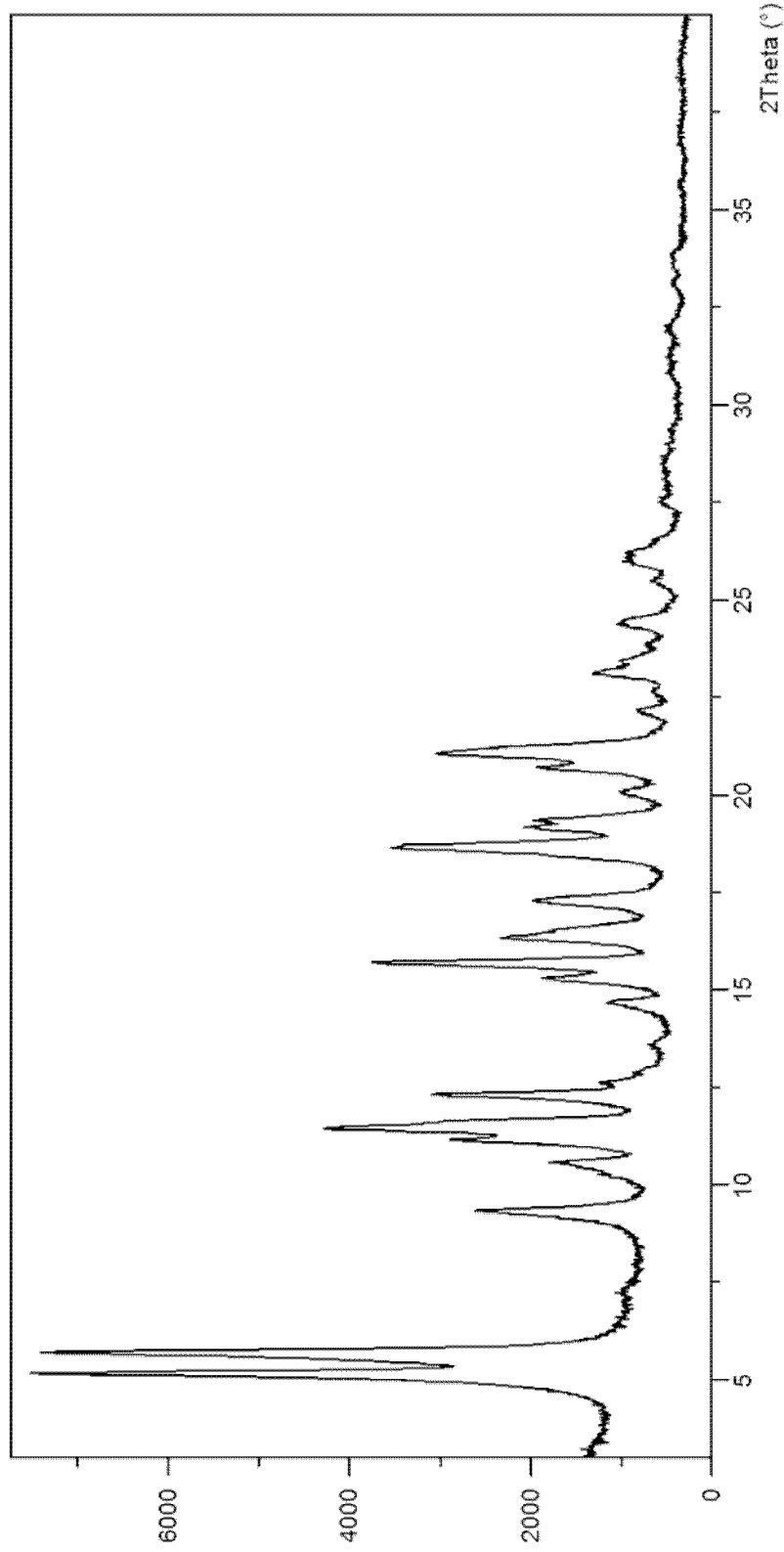
FIG. 9 shows the X-ray powder diffractogram (XRPD) of the cocrystal Form V. The spectrum expresses intensity (I; counts) versus degrees 2 theta (°).

The cocrystal Form V may be further characterized by an X-ray diffractogram as in FIG. 9.

The cocrystal Form V may also be further characterized by the following $^1$H NMR spectrum (CD$_3$OD, 400 MHz, δ): 6.08 (s, 2H, ArH); 5.29 (s, 1H); 4.45 (d, 2H, J=14.1 Hz); 3.99-3.90 (m, 2H); 3.42-3.35 (m, 1H); 3.26-3.19 (m, 1H); 2.94-2.87 (m, 1H); 2.38 (t, 2H, J=7.7 Hz); 2.35-2.25 (m, 1H); 2.24-2.08 (m, 2H); 2.02-1.92 (m, 3H); 1.77-1.71 (m, 2H); 1.68 (s, 3H); 1.64 (s, 3H); 1.59-1.51 (m, 2H); 1.39-1.25 (m, 4H); 0.90 (t, 3H, J=7.0 Hz).

Figure 10:
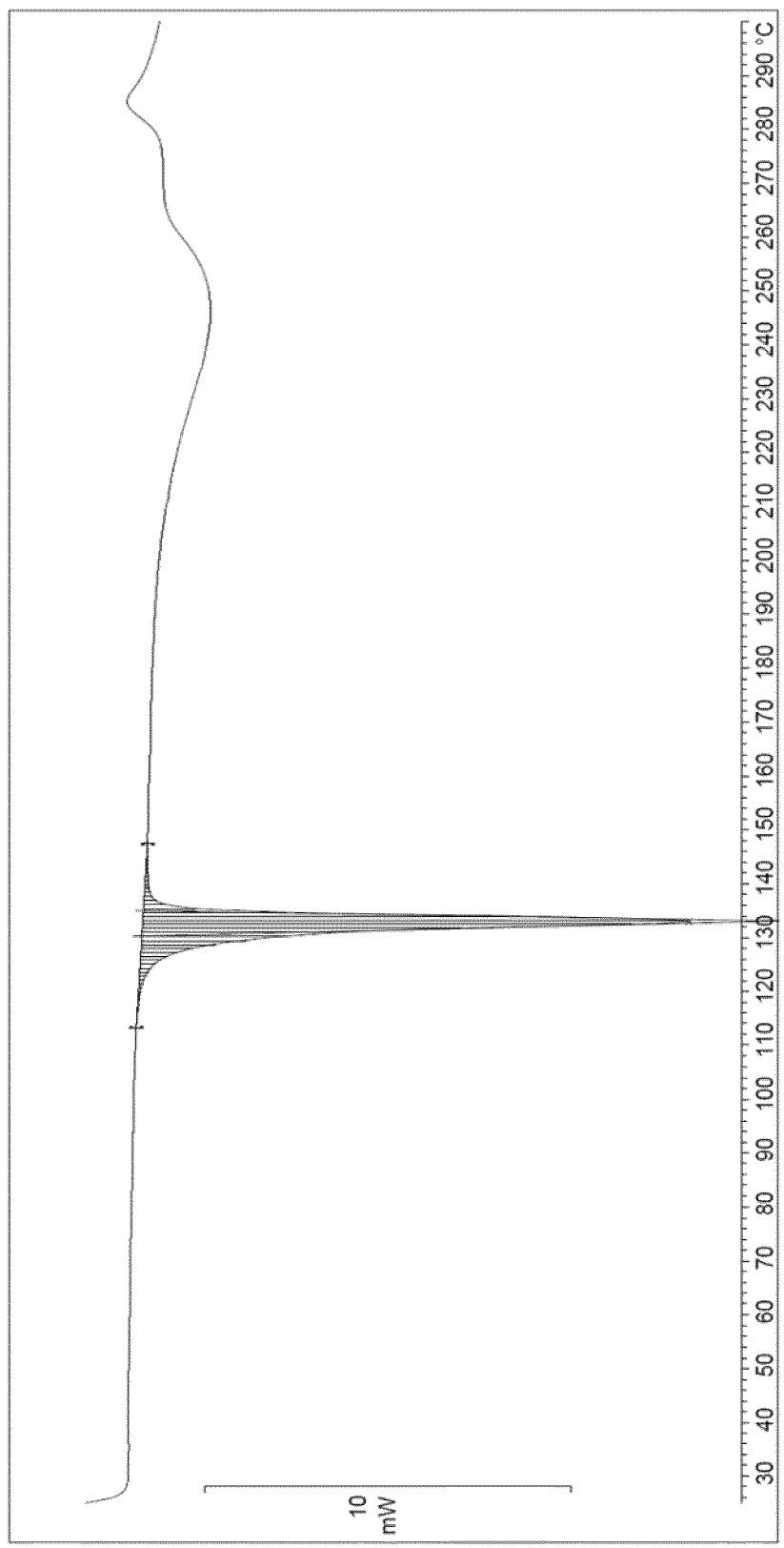
FIG. 10 shows the DSC of cocrystal Form V. The spectrum expresses the heat flow (mW/mg) versus temperature (° C.).

The cocrystal Form V may also be further characterized by DSC (differential scanning calorimetry) analysis as shown in FIG. 10. The DSC analysis of cocrystal Form V shows an endothermic event with an onset at 130° C. which corresponds to the melting point of cocrystal Form V followed by endothermic and exothermic peaks possibly due to degradation (decomposition) events. The cocrystal Form V may also be further characterized by having a melting range of 128-134° C.

The cocrystal of Form V prepared from pure commercial CBD (98.6% a/a HPLC—method 1) has a purity similar to the starting material. It is worth noting that the coformer is not detected in the HPLC conditions used in this analysis.

The cocrystal Form V is in a molar ratio 1:1 (CBD:DL-proline).

In an embodiment, the cocrystal is a cocrystal of CBD and (2S,3aS,7aS)-octahydro-1H-indole-2-carboxylic acid, also named Form VI. For the purposes of the invention, (2S,3aS,7aS)-octahydro-1H-indole-2-carboxylic acid has the CAS No. 80875-98-5. The structure of (2S,3aS,7aS)-octahydro-1H-indole-2-carboxylic acid is the following:

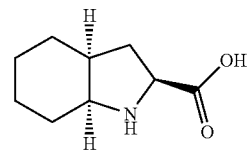 [SMILES: O=C(O)[C@@H]1C[C@@H]2CCCC[C@@H]2N1]

In an embodiment, the cocrystal Form VI is characterized by having an X-ray powder diffractogram that comprises characteristic peaks at 4.4, 6.2 and 8.3±0.3 degrees 2 theta at a Cu—$K_\alpha$ radiation, λ=1.5406 Å. In an embodiment, the cocrystal Form VI is characterized by having an X-ray powder diffractogram that comprises further characteristic peaks at 10.0, 13.3 and 16.0±0.3 degrees 2 theta at a Cu—$K_\alpha$ radiation, λ=1.5406 Å.

More specifically, the cocrystal Form VI is characterized by exhibiting in the X-ray powder diffractogram a pattern of peaks, expressed in 2 theta units in degrees, 2θ (°), which is shown in Table 6.

TABLE 6

List of selected peaks (only peaks with relative intensity greater than or equal to 1% are indicated):

| Pos. [°2θ] | d-spacing [Å] | Rel. Int. [%] |
|---|---|---|
| 4.4 | 20.2 | 100 |
| 5.4 | 16.3 | 31 |
| 6.2 | 14.3 | 68 |
| 8.3 | 10.7 | 39 |
| 8.8 | 10.1 | 33 |
| 10.0 | 8.8 | 88 |
| 10.9 | 8.1 | 12 |
| 11.3 | 7.8 | 19 |
| 12.4 | 7.1 | 31 |
| 13.3 | 6.6 | 29 |
| 13.9 | 6.4 | 11 |
| 14.3 | 6.2 | 9 |
| 15.4 | 5.8 | 8 |
| 16.0 | 5.5 | 64 |
| 16.6 | 5.4 | 47 |
| 17.6 | 5.0 | 32 |
| 18.2 | 4.9 | 61 |
| 18.7 | 4.7 | 3 |
| 19.1 | 4.6 | 5 |
| 19.5 | 4.5 | 19 |
| 20.2 | 4.4 | 8 |
| 20.6 | 4.3 | 24 |
| 21.0 | 4.2 | 4 |
| 21.5 | 4.1 | 8 |
| 21.7 | 4.1 | 12 |
| 22.0 | 4.0 | 9 |
| 22.6 | 3.9 | 7 |
| 22.9 | 3.9 | 18 |
| 23.8 | 3.7 | 8 |
| 24.3 | 3.7 | 15 |
| 25.0 | 3.6 | 5 |
| 25.4 | 3.5 | 5 |
| 25.8 | 3.5 | 7 |
| 26.6 | 3.4 | 2 |
| 28.1 | 3.2 | 3 |
| 28.7 | 3.1 | 3 |
| 29.1 | 3.1 | 3 |
| 29.8 | 3.0 | 4 |
| 31.1 | 2.9 | 2 |
| 32.1 | 2.8 | 2 |
| 33.9 | 2.6 | 1 |
| 35.6 | 2.5 | 1 |
| 37.1 | 2.4 | 2 |

Figure 12:
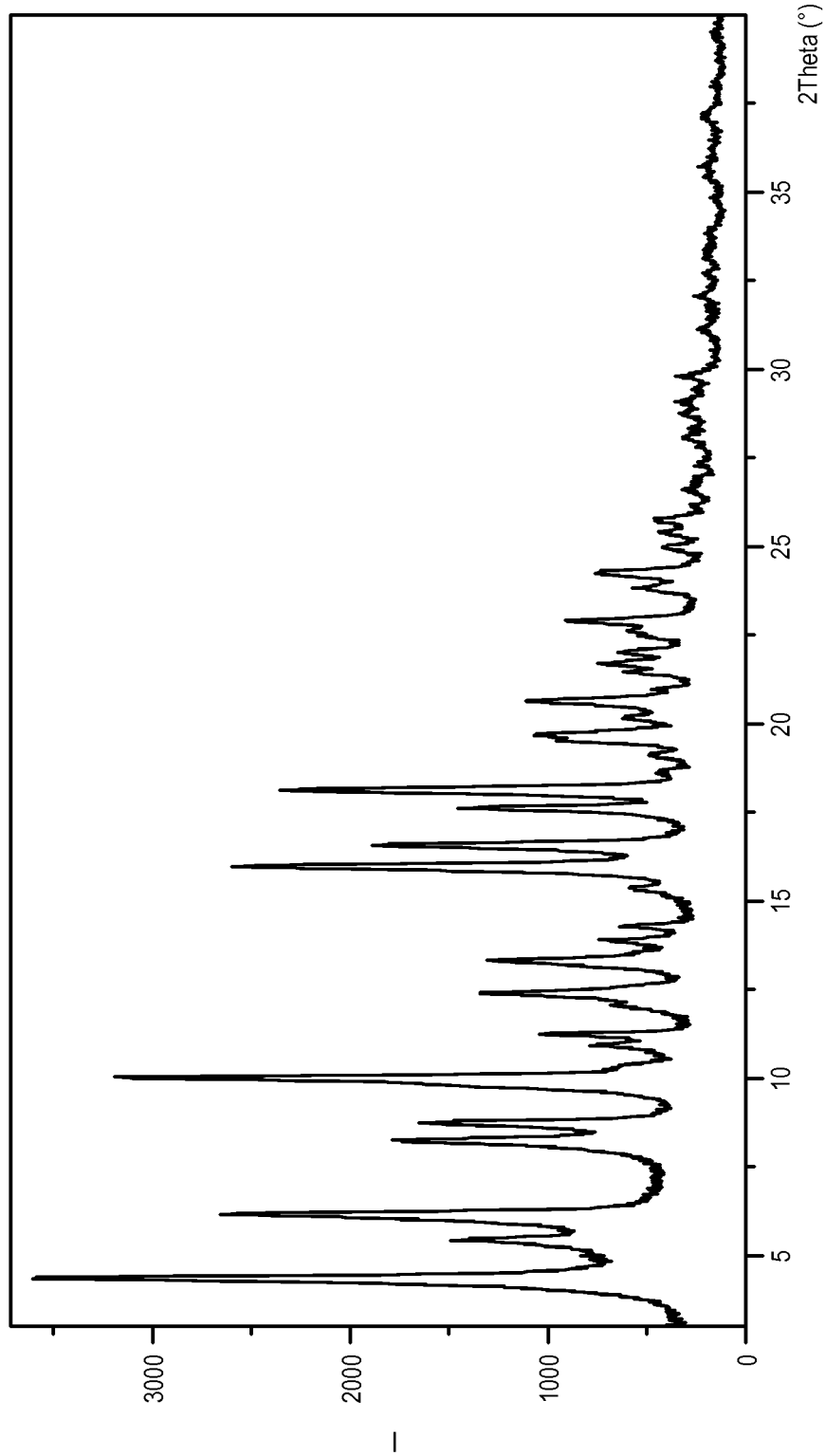
FIG. 12 shows the X-ray powder diffractogram (XRPD) of the cocrystal Form VI. The spectrum expresses intensity (I; counts) versus degrees 2 theta (°).

The cocrystal Form VI may be further characterized by an X-ray diffractogram as in FIG. 12.

The cocrystal Form VI may also be further characterized by the following $^1$H NMR spectrum (CD$_3$OD, 400 MHz, δ): 6.08 (s, 2H, ArH); 5.29 (s, 1H); 4.45 (d, 2H, J=14.2 Hz); 4.01-3.91 (m, 2H); 3.67-3.63 (m, 1H); 2.94-2.87 (m, 1H); 2.41-2.31 (m, 4H); 2.27-2.15 (m, 1H); 2.12-2.05 (m, 1H); 2.04-1.96 (m, 1H); 1.93-1.84 (m, 1H); 1.81-1.61 (m, 11H); 1.59-1.25 (m, 10H); 0.90 (t, 3H, J=7.0 Hz).

Figure 13:
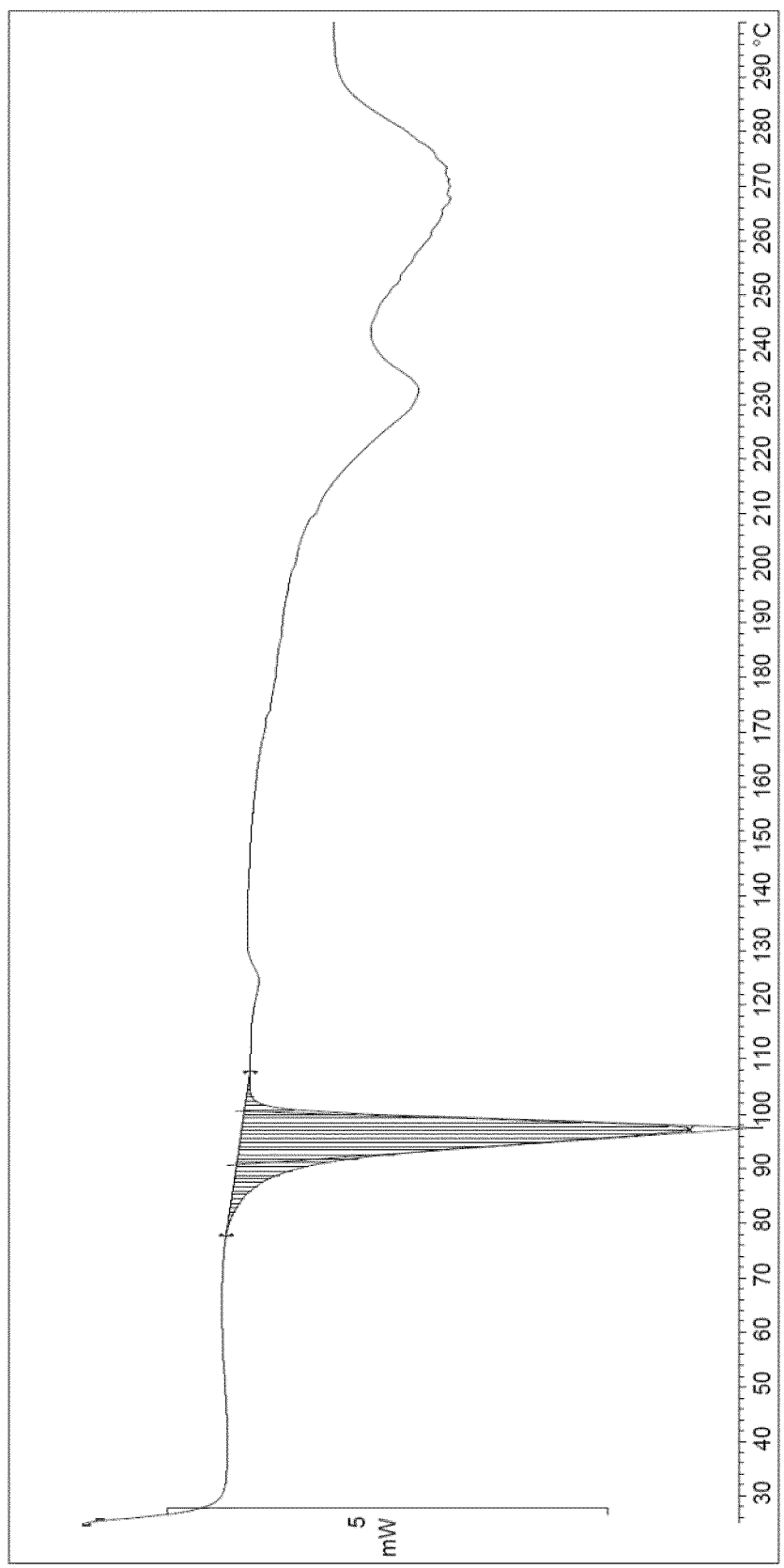
FIG. 13 shows the DSC of cocrystal Form VI. The spectrum expresses the heat flow (mW/mg) versus temperature (° C.).

The cocrystal Form VI may also be further characterized by DSC (differential scanning calorimetry) analysis as shown in FIG. 13. The DSC analysis of cocrystal Form VI shows an endothermic event with an onset at 91° C. which corresponds to the melting point of cocrystal Form VI followed by endothermic peaks possibly due to degradation (decomposition) events. The cocrystal Form VI may also be further characterized by having a melting range of 90-100° C.

The cocrystal of Form VI prepared from pure commercial CBD (98.6% a/a HPLC—method 1) has a purity similar to the starting material. It is worth noting that the coformer is not detected in the HPLC conditions used in this analysis.

The cocrystal Form VI is in a molar ratio 1:1 (CBD:(2S,3aS,7aS)-octahydro-1H-indole-2-carboxylic acid).

In an embodiment, the cocrystal of the invention is a cocrystal of (−)-(6aR,10aR)-6,6,9-trimethyl-3-pentyl-6a,7,8,10a-tetrahydro-6H-benzo[c]chromen-l-ol and L-proline, also named Form VII.

In an embodiment, the cocrystal Form VII of the present invention is characterized by having an X-ray powder diffractogram that comprises characteristic peaks at 5.1, 11.5 and 20.5±0.3 degrees 2 theta at a Cu—K$_α$ radiation, λ=1.5406 Å. In an embodiment, the cocrystal Form I of the present invention is characterized by having an X-ray powder diffractogram that comprises further characteristic peaks at 10.3 and 15.5±0.3 degrees 2 theta at a Cu—K$_α$ radiation, λ=1.5406 Å.

More specifically, the cocrystal Form VII of the present invention is characterized by exhibiting in the X-ray powder diffractogram a pattern of peaks, expressed in 2 theta units in degrees, 2θ (°), which is shown in Table 7.

TABLE 7

List of selected peaks (only peaks with relative intensity greater than or equal to 1% are indicated):

| Pos. [°2θ] | d-spacing [Å] | Rel. Int. [%] |
|---|---|---|
| 5.1 | 17.3 | 100 |
| 7.2 | 12.2 | 6 |
| 8.5 | 10.4 | 3 |
| 10.3 | 8.6 | 6 |
| 11.5 | 7.7 | 7 |
| 12.3 | 7.2 | 31 |
| 14.3 | 6.2 | 6 |
| 14.6 | 6.1 | 1 |
| 15.5 | 5.7 | 8 |
| 16.1 | 5.5 | 27 |
| 16.4 | 5.4 | 6 |
| 17.7 | 5.0 | 7 |
| 18.4 | 4.8 | 11 |
| 18.7 | 4.7 | 14 |
| 19.1 | 4.7 | 6 |
| 19.8 | 4.5 | 4 |
| 20.5 | 4.3 | 14 |
| 20.8 | 4.3 | 15 |
| 21.1 | 4.2 | 1 |
| 21.8 | 4.1 | 10 |
| 23.6 | 3.8 | 7 |
| 24.2 | 3.7 | 1 |
| 24.8 | 3.6 | 5 |
| 26.2 | 3.4 | 3 |
| 28.4 | 3.1 | 5 |

Figure 14:
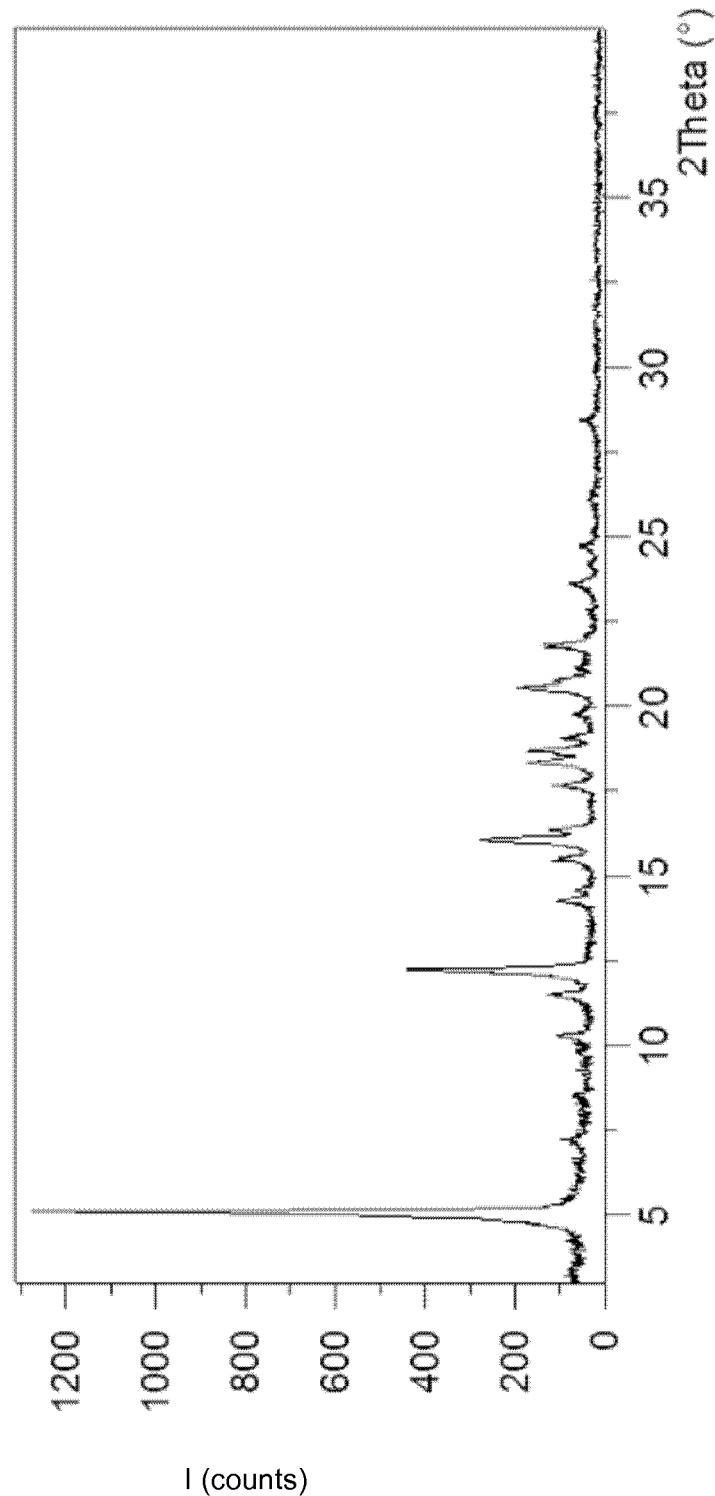
FIG. 14 shows the X-ray powder diffractogram (XRPD) of the cocrystal Form VII. The spectrum expresses intensity (I; counts) versus degrees 2 theta (°).

The cocrystal Form VII of the present invention may be further characterized by an X-ray diffractogram as in FIG. 14.

The cocrystal Form VII of the present invention may also be further characterized by the following $^1$H NMR spectrum (CD$_3$OD, 400 MHz, δ): 6.42 (m, 1H, ArH); 6.15-6.07 (dd, 2H, J=34.0, 1.7 Hz); 3.98-3.94 (dd, 1H, J=8.7, 6.2 Hz); 3.41-3.35 (m, 1H); 3.25-3.19 (m, 1H); 3.16-3.13 (m, 1H); 2.41-2.37 (t, 2H); 2.34-2.25 (m, 1H); 2.15-2.07 (m, 3H); 2.00-1.90 (m, 3H); 1.65 (m, 3H); 1.68 (s, 3H); 1.61-1.51 (m, 3H); 1.45-1.25 (m, 10H); 1.04 (s, 3H); 0.89 (dd, 4H, J=7.4, 6.6 Hz).

Figure 15:
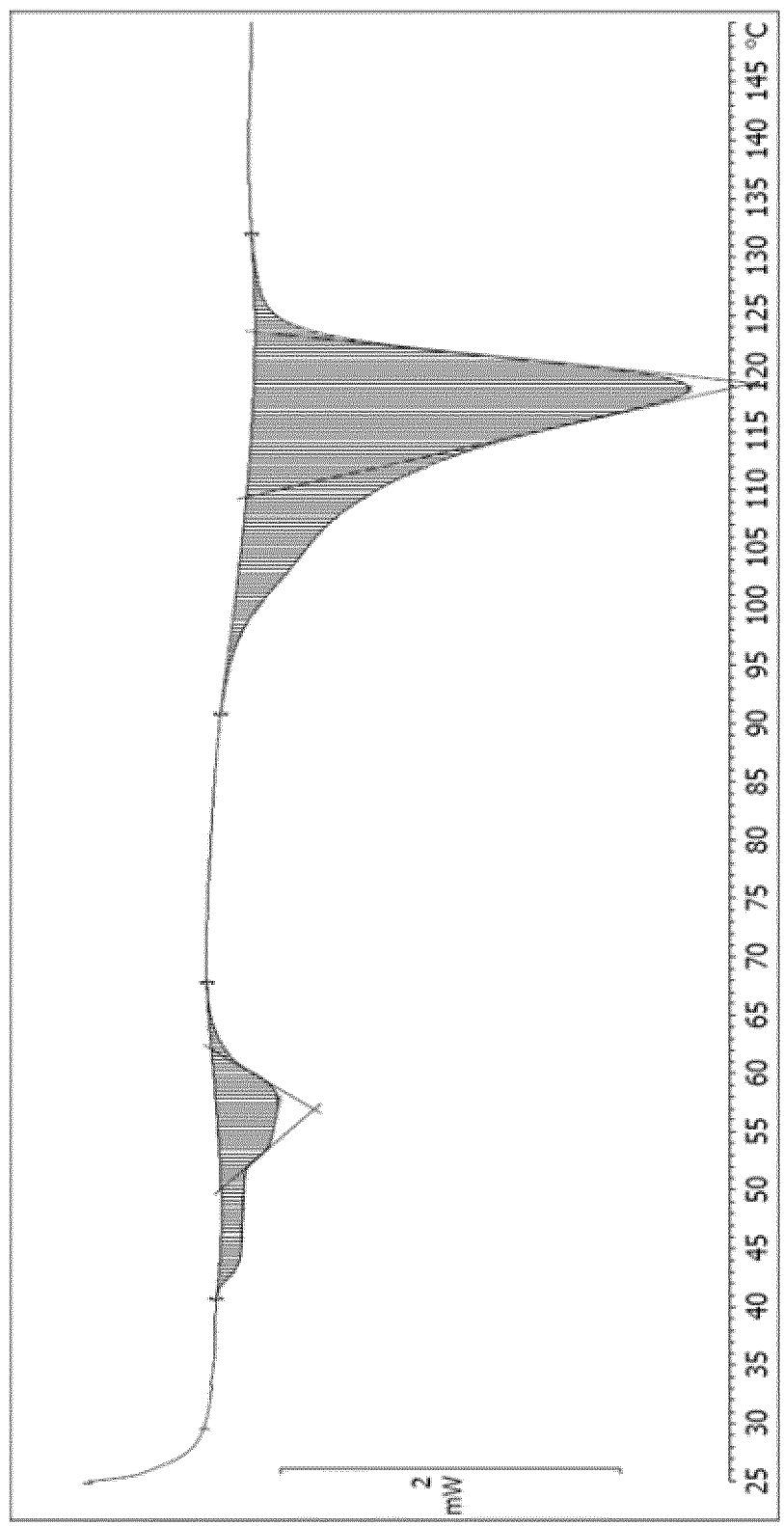
FIG. 15 shows the DSC of cocrystal Form VII. The spectrum expresses the heat flow (mW/mg) versus temperature (° C.).

The cocrystal Form VII of the present invention may also be further characterized by DSC (differential scanning calorimetry) analysis as shown in FIG. 15. The DSC analysis of cocrystal Form VII shows a first endothermic event with an onset at 50° C. followed by a second endothermic event with an onset at ca 109° C. which correspond to the melting of the cocrystal Form VII. The first event should correspond to the evaporation of residual solvents because cocrystal Form VII remained stable after heating up to 75° C. and DSC experiments indicated that this event is not reversible. The cocrystal Form VII of the present invention may also be further characterized by having a melting range of about 109-120° C.

The cocrystal Form VII of the present invention is in a molar ratio 1:1 (THC:L-proline).

In an embodiment, the cocrystal of Form VII of the present invention has a purity equal to or higher than 95% a/a measured by GC.

In an embodiment, the cocrystal of the invention is a cocrystal of (−)-(6aR,10aR)-6,6,9-trimethyl-3-pentyl-6a,7,8,10a-tetrahydro-6H-benzo[c]chromen-I-ol and D-proline, also named Form VIII.

In an embodiment, the cocrystal Form VIII of the present invention is characterized by having an X-ray powder diffractogram that comprises characteristic peaks at 5.1, 11.4 and 20.6±0.3 degrees 2 theta at a Cu—K$_\alpha$ radiation, λ=1.5406 Å.

More specifically, the cocrystal Form VIII of the present invention is characterized by exhibiting in the X-ray powder diffractogram a pattern of peaks, expressed in 2 theta units in degrees, 2θ (°), which is shown in Table 8.

TABLE 8

List of selected peaks (only peaks with relative intensity greater than or equal to 1% are indicated):

| Pos. [°2θ] | d-spacing [Å] | Rel. Int. [%] |
| --- | --- | --- |
| 5.1 | 17.4 | 100 |
| 7.2 | 12.3 | 3 |
| 10.2 | 8.7 | 5 |
| 11.4 | 7.7 | 7 |
| 12.5 | 7.1 | 17 |
| 14.5 | 6.1 | 10 |
| 15.4 | 5.8 | 4 |
| 16.2 | 5.5 | 19 |
| 17.8 | 5.0 | 5 |
| 18.5 | 4.8 | 11 |
| 19.2 | 4.6 | 8 |
| 19.9 | 4.5 | 2 |
| 20.6 | 4.3 | 6 |
| 21.8 | 4.1 | 5 |
| 22.5 | 4.0 | 5 |
| 24.2 | 3.7 | 5 |
| 25.3 | 3.5 | 5 |
| 25.8 | 3.5 | 1 |
| 27.4 | 3.3 | 1 |
| 28.8 | 3.1 | 2 |
| 30.2 | 3.0 | 1 |
| 31.1 | 2.9 | 2 |
| 32.8 | 2.7 | 1 |
| 35.0 | 2.6 | 1 |
| 37.6 | 2.4 | 2 |
| 38.3 | 2.4 | 1 |

Figure 16:
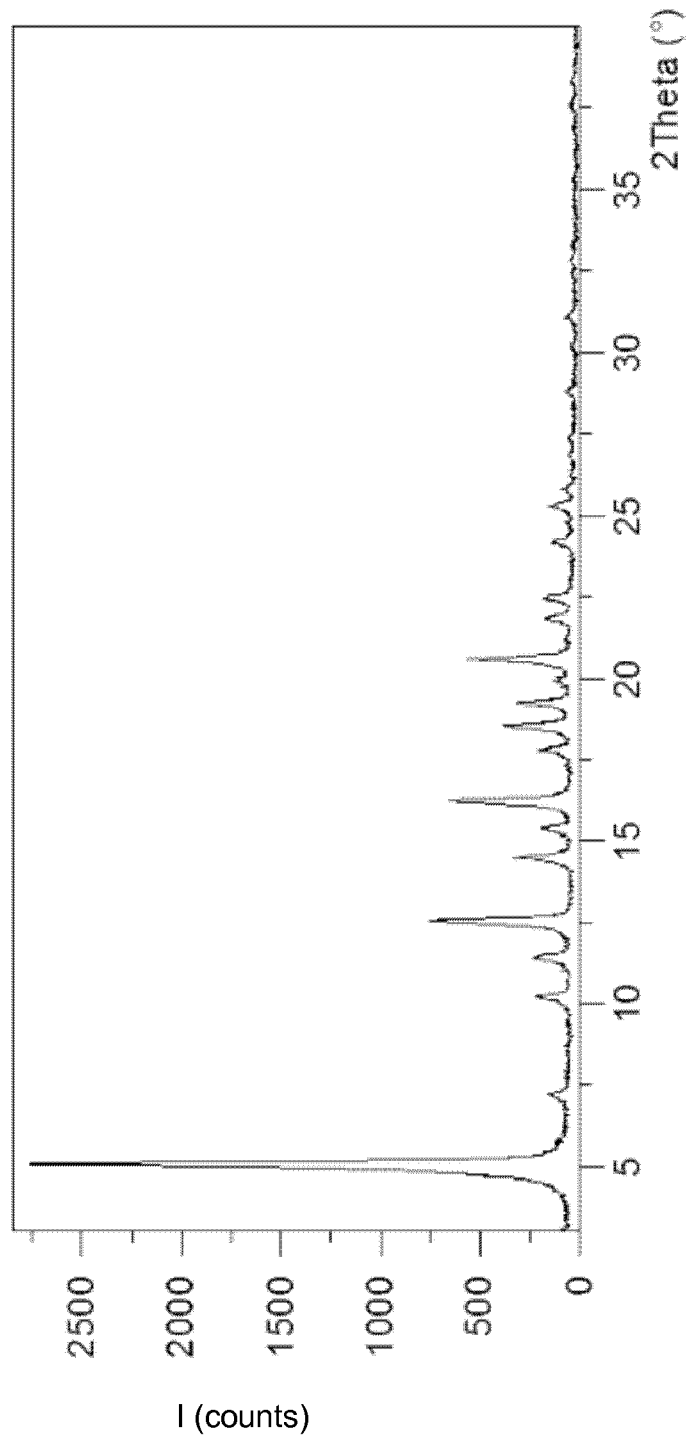
FIG. 16 shows the X-ray powder diffractogram (XRPD) of the cocrystal Form VIII. The spectrum expresses intensity (I; counts) versus degrees 2 theta (°).

The cocrystal Form VIII of the present invention may be further characterized by an X-ray diffractogram as in FIG. 16.

The cocrystal Form VIII of the present invention may also be further characterized by the following $^1$H NMR spectrum (CD$_3$OD, 400 MHz, δ): 6.42 (m, 1H, ArH); 6.15-6.07 (dd, 2H, J=34.0, 1.7 Hz); 3.98-3.94 (dd, 1H, J=8.7, 6.2 Hz); 3.41-3.35 (m, 1H); 3.25-3.19 (m, 1H); 3.16-3.13 (m, 1H); 2.41-2.37 (t, 2H); 2.34-2.25 (m, 1H); 2.15-2.07 (m, 3H); 2.00-1.90 (m, 3H); 1.65 (m, 3H); 1.68 (s, 3H); 1.61-1.51 (m, 3H); 1.45-1.25 (m, 10H); 1.04 (s, 3H); 0.89 (dd, 4H, J=7.4, 6.6 Hz).

Figure 17:
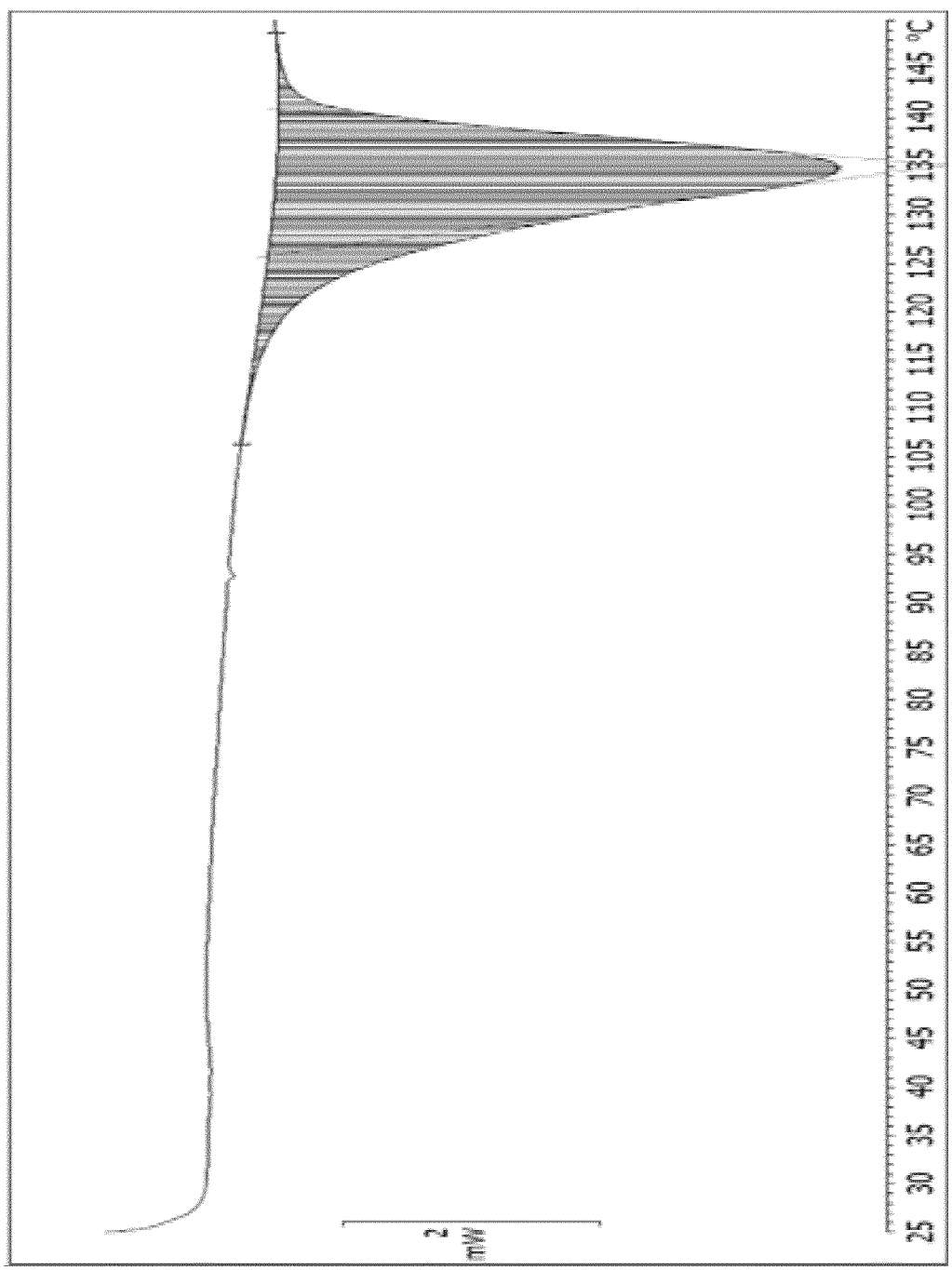
FIG. 17 shows the DSC of cocrystal Form VIII. The spectrum expresses the heat flow (mW/mg) versus temperature (° C.).

The cocrystal Form VIII of the present invention may also be further characterized by DSC (differential scanning calorimetry) analysis as shown in FIG. 17. The DSC analysis of cocrystal Form VIII shows only one endothermic event with an onset at ca 125° C. which should correspond to the melting of Form VIII. The cocrystal Form VIII of the present invention may also be further characterized by having a melting range of about 125-141° C.

The cocrystal Form VIII of the present invention is in a molar ratio 1:1 (THC:D-proline).

In an embodiment, the cocrystal of Form VIII of the present invention has a purity equal to or higher than 95% a/a measured by GC.

In an embodiment, the cocrystal of the invention is a cocrystal of delta8-THC and L-proline, also named Form IX.

In an embodiment, the cocrystal Form IX of the present invention is characterized by having an X-ray powder diffractogram that comprises characteristic peaks at 5.1, 18.7 and 20.5±0.3 degrees 2 theta at a Cu—K$_\alpha$ radiation, λ=1.5406 Å. In an embodiment, the cocrystal Form IX of the present invention is characterized by having an X-ray powder diffractogram that comprises further characteristic peaks at 10.3, 11.5 and 21.9±0.3 degrees 2 theta at a Cu—K$_\alpha$ radiation, λ=1.5406 Å.

More specifically, the cocrystal Form IX of the present invention is characterized by exhibiting in the X-ray powder diffractogram a pattern of peaks, expressed in 2 theta units in degrees, 2θ (°), which is shown in Table 9.

TABLE 9

List of selected peaks (only peaks with relative intensity greater than or equal to 1% are indicated):

| Pos. [°2Th.] | d-spacing [Å] | Rel. Int. [%] |
| --- | --- | --- |
| 5.1 | 17.2 | 100 |
| 10.3 | 8.6 | 3 |
| 11.5 | 7.7 | 4 |
| 12.3 | 7.2 | 17 |
| 14.3 | 6.2 | 4 |
| 15.5 | 5.7 | 4 |
| 16.1 | 5.5 | 7 |
| 17.7 | 5.0 | 3 |
| 18.7 | 4.8 | 11 |
| 20.5 | 4.3 | 7 |
| 21.9 | 4.1 | 5 |
| 23.8 | 3.7 | 2 |
| 28.4 | 3.1 | 2 |
| 31.2 | 2.9 | 1 |

Figure 18:
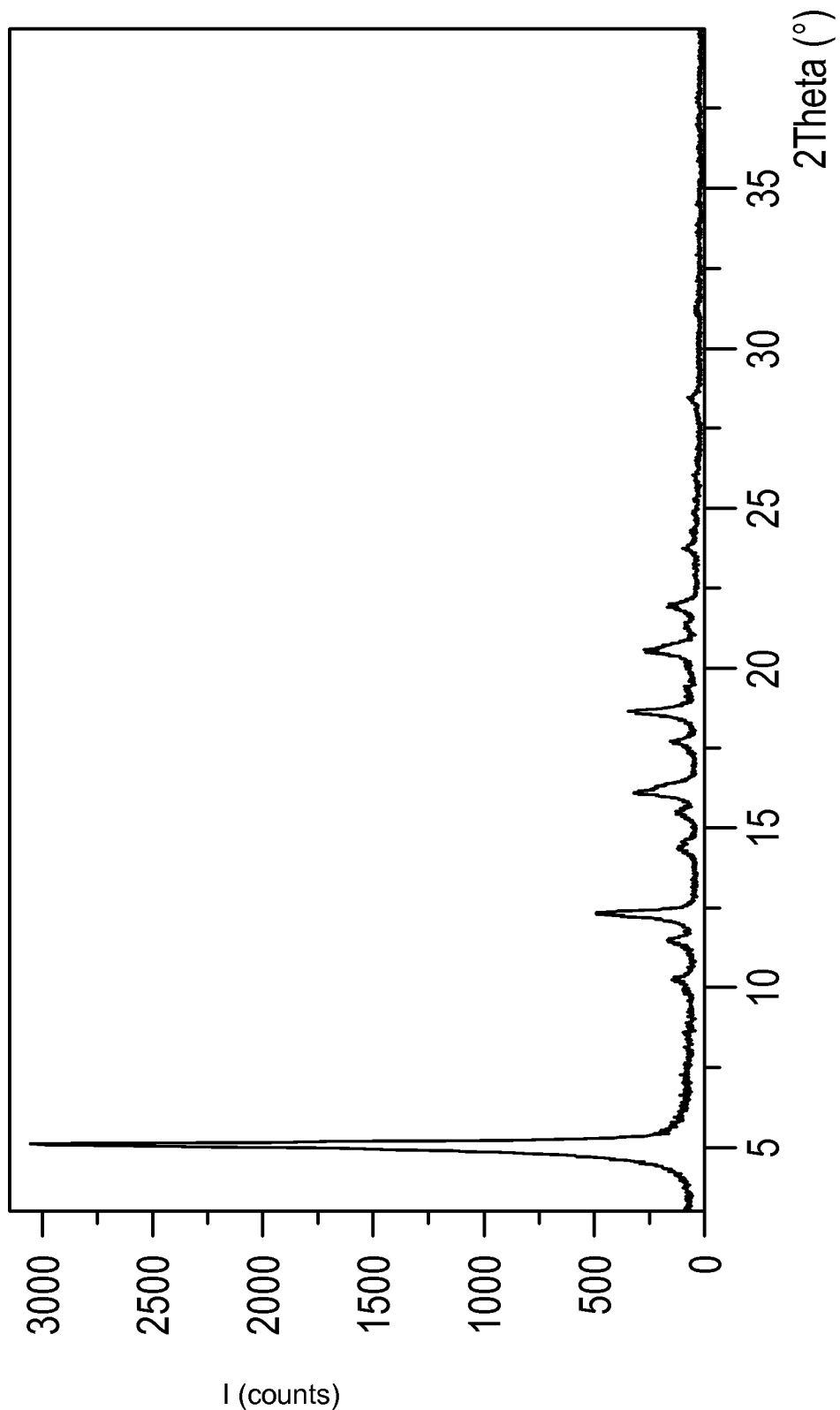
FIG. 18 shows the X-ray powder diffractogram (XRPD) of the cocrystal Form IX. The spectrum expresses intensity (I; counts) versus degrees 2 theta (°).

The cocrystal Form IX of the present invention may be further characterized by an X-ray diffractogram as in FIG. 18.

The cocrystal Form IX of the present invention is in a molar ratio 1:1 (delta8-THC:L-proline).

In an embodiment, the cocrystal of Form IX of the present invention has a purity equal to or higher than 99.3% a/a measured by HPLC (method 1).

In an embodiment, the cocrystal of the invention is a cocrystal of delta8-THC and D-proline, also named Form X.

In an embodiment, the cocrystal Form X of the present invention is characterized by having an X-ray powder diffractogram that comprises characteristic peaks at 5.1, 16.1 and 20.4±0.3 degrees 2 theta at a Cu—K$_\alpha$ radiation, λ=1.5406 Å. In an embodiment, the cocrystal Form X of the present invention is characterized by having an X-ray powder diffractogram that comprises further characteristic peaks at 10.1 and 21.7±0.3 degrees 2 theta at a Cu—K$_\alpha$ radiation, λ=1.5406 Å.

More specifically, the cocrystal Form X of the present invention is characterized by exhibiting in the X-ray powder diffractogram a pattern of peaks, expressed in 2 theta units in degrees, 2θ (°), which is shown in Table 10.

TABLE 10

List of selected peaks (only peaks with relative intensity greater than or equal to 1% are indicated):

| Pos. [°2Th.] | d-spacing [Å] | Rel. Int. [%] |
| --- | --- | --- |
| 5.0 | 17.6 | 100 |
| 7.1 | 12.5 | 4 |
| 10.1 | 8.7 | 9 |
| 11.4 | 7.8 | 12 |
| 12.4 | 7.1 | 18 |
| 14.4 | 6.2 | 9 |
| 15.1 | 5.9 | 4 |
| 15.2 | 5.8 | 3 |
| 16.1 | 5.5 | 23 |
| 17.7 | 5.0 | 5 |
| 18.4 | 4.8 | 12 |
| 19.1 | 4.6 | 12 |
| 20.4 | 4.3 | 17 |
| 21.7 | 4.1 | 8 |
| 22.3 | 4.0 | 6 |
| 24.0 | 3.7 | 4 |
| 25.2 | 3.5 | 8 |
| 25.7 | 3.5 | 1 |

Figure 19:
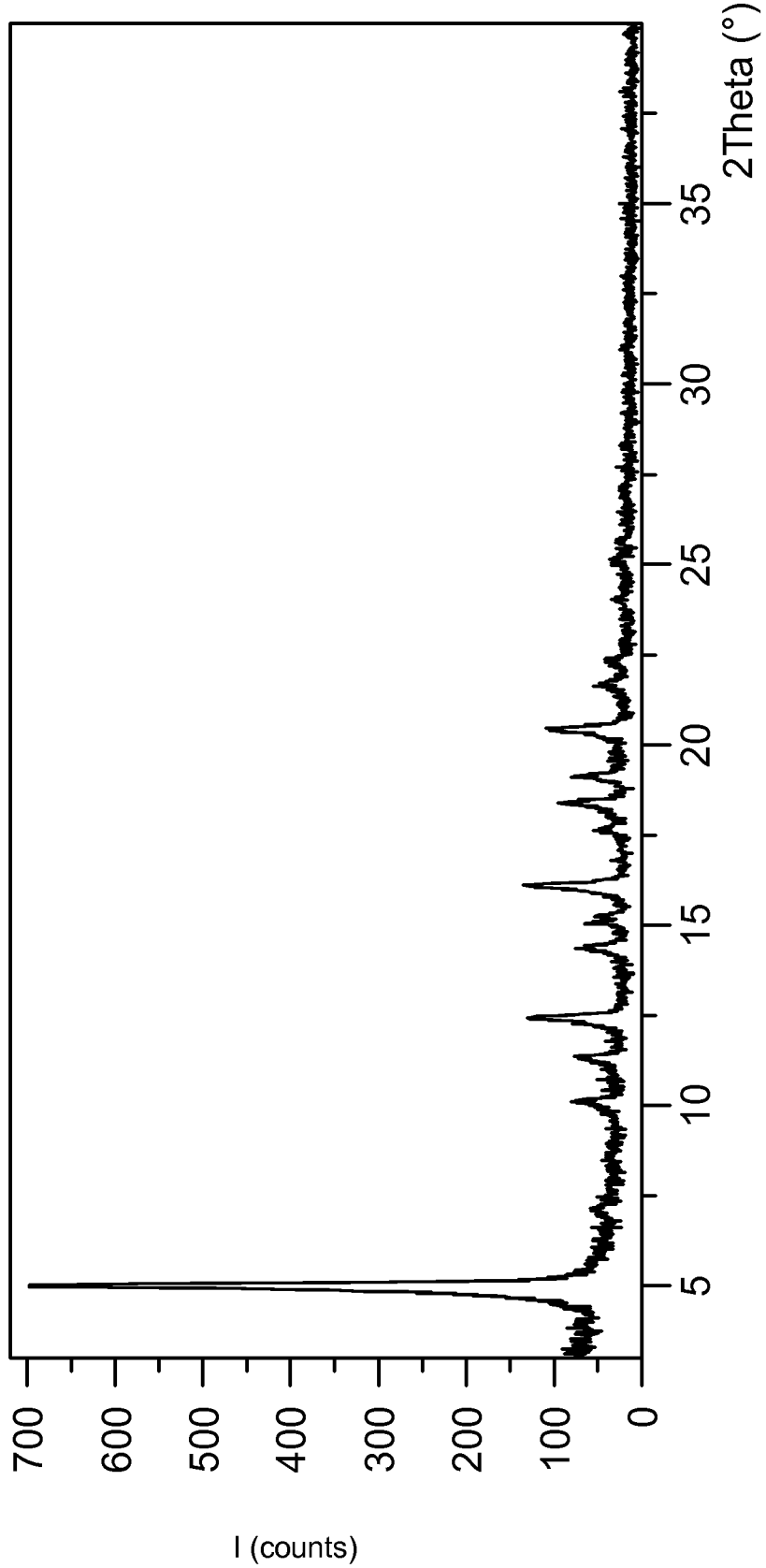
FIG. 19 shows the X-ray powder diffractogram (XRPD) of the cocrystal Form X. The spectrum expresses intensity (I; counts) versus degrees 2 theta (°).

The cocrystal Form X of the present invention may be further characterized by an X-ray diffractogram as in FIG. 19.

The cocrystal Form X of the present invention is in a molar ratio 1:1 (delta8-THC:D-proline).

In an embodiment, the cocrystal of Form X of the present invention has a purity equal to or higher than 96.4% a/a measured by HPLC (method 1).

In a particular embodiment, the solid composition comprises a cocrystal wherein the cannabinoid is CBN and betaine, also named Form XI.

In an embodiment, the cocrystal Form XI of the present invention is characterized by having an X-ray powder diffractogram that comprises characteristic peaks at 6.3, 7.1 and 9.0±0.3 degrees 2 theta at a Cu—K$_\alpha$ radiation, λ=1.5406 Å. Specifically, the cocrystal Form XI of the present invention is characterized by exhibiting in the X-ray powder diffractogram a pattern of peaks, expressed in 2 theta units in degrees, 2θ (°), which is shown in Table 11.

TABLE 11

List of selected peaks (only peaks with relative intensity greater than or equal to 1% are indicated):

| Pos. [°2Th.] | d-spacing [Å] | Rel. Int. [%] |
| --- | --- | --- |
| 5.1 | 17.39 | 8 |
| 6.3 | 14.13 | 100 |
| 7.1 | 12.43 | 13 |
| 8.4 | 10.47 | 21 |
| 9.0 | 9.87 | 13 |
| 10.2 | 8.69 | 21 |
| 12.3 | 7.21 | 11 |
| 12.7 | 6.95 | 5 |
| 13.5 | 6.57 | 8 |
| 15.0 | 5.89 | 4 |
| 16.8 | 5.28 | 7 |
| 18.0 | 4.92 | 6 |
| 18.4 | 4.83 | 6 |
| 18.9 | 4.69 | 15 |
| 19.9 | 4.47 | 5 |
| 20.46 | 4.34 | 7 |
| 21.7 | 4.09 | 5 |

TABLE 11-continued

List of selected peaks (only peaks with relative intensity greater than or equal to 1% are indicated):

| Pos. [°2Th.] | d-spacing [Å] | Rel. Int. [%] |
| --- | --- | --- |
| 22.5 | 3.95 | 6 |
| 24.5 | 3.63 | 3 |
| 25.2 | 3.54 | 4 |
| 25.6 | 3.49 | 13 |
| 27.2 | 3.28 | 3 |

Figure 20:
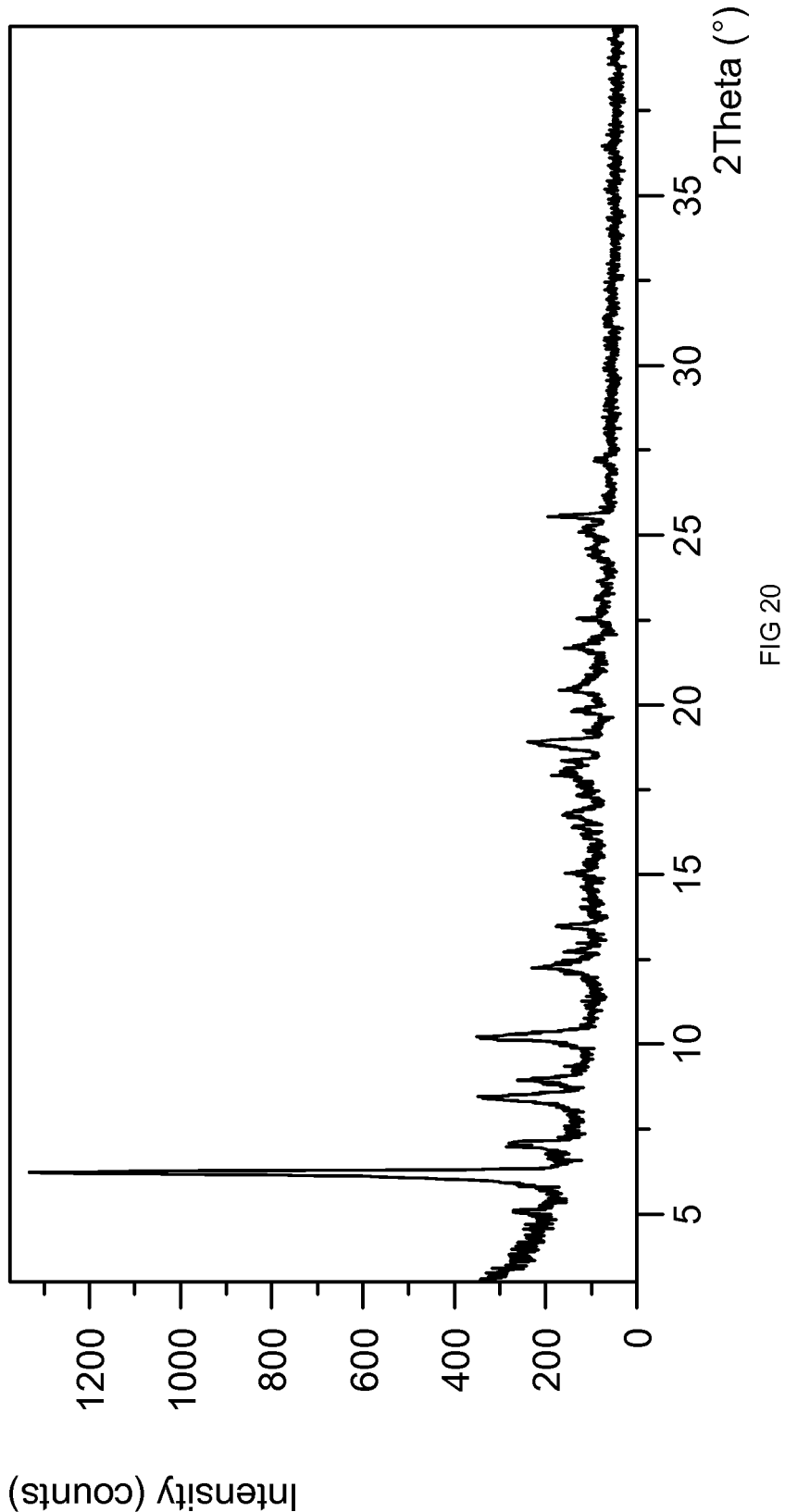
FIG. 20 shows the X-ray powder diffractogram (XRPD) of the cocrystal Form XI. The spectrum expresses intensity (I; counts) versus degrees 2 theta (°).

The cocrystal Form XI of the present invention may be further characterized by an X-ray diffractogram as in FIG. 20.

The cocrystal Form XI of the present invention may also be further characterized by the following $^1$H NMR spectrum (CD$_3$OD, 400 MHz, δ): 8.36-8.33 (m, 1H); 7.13 (d, J=7.8 Hz, 1H); 7.05-7.00 (m, 1H); 6.36 (d, J=2.0 Hz, 1H); 6.26 (d, J=2.0 Hz, 1H); 3.82 (s, 2 H); 3.27 (s, 9H); 2.48 (t, J=7.8 Hz, 2 H); 2.34 (s, 3H); 1.67-1.55 (m, 2H); 1.54 (s, 6H); 1.43-1.27 (m, 4H); 0.92 (t, J=7.0 HZ, 3 H).

Figure 21:
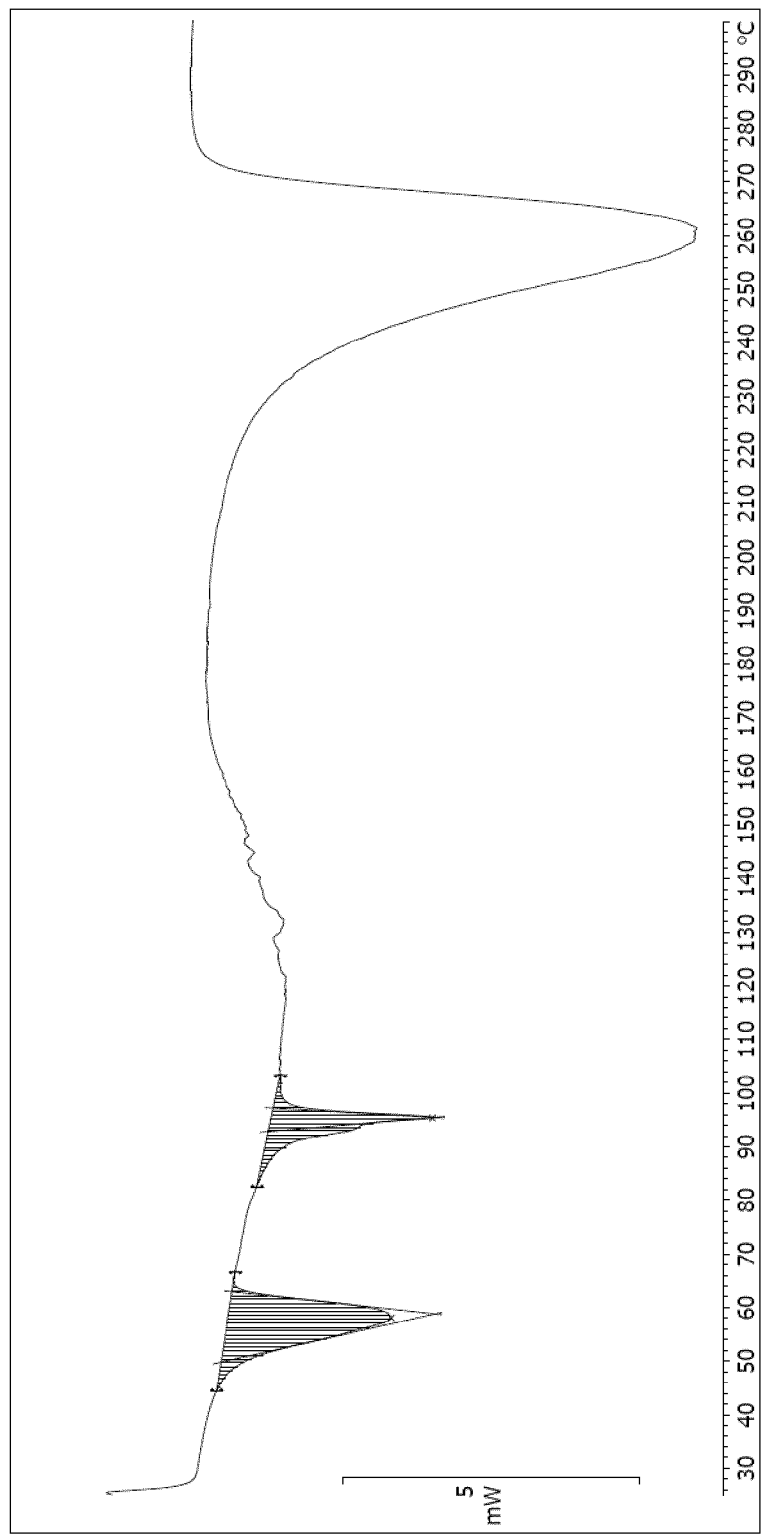
FIG. 21 shows the DSC of cocrystal Form XI. The spectrum expresses the heat flow (mW/mg) versus temperature (° C.).

The cocrystal Form XI of the present invention may also be further characterized by DSC (differential scanning calorimetry) analysis as shown in FIG. 21. The DSC analysis of cocrystal Form XI shows a first broad endothermic event with an onset at 50° C. which could be due to a dehydration event. Then, an endothermic peak with an onset at 93° C. might correspond to a melting event. Therefore, DSC seems to indicate that cocrystal Form XI is a hydrate.

KF analysis of Form XI (11 mg) performed in duplicate gave a water content of 10.6 w/w confirming that this form is a hydrate.

The cocrystal Form XI of the present invention is in a molar ratio 1:1 (CBN:betaine).

In an embodiment, the cocrystal of Form XI of the present invention has a purity equal to or higher than 99.3% a/a measured by HPLC (method 2).

In a particular embodiment, the solid composition comprises a cocrystal wherein the cannabinoid is CBN and L-proline, also named Form XII.

In an embodiment, the cocrystal Form XII of the present invention is characterized by having an X-ray powder diffractogram that comprises characteristic peak at 4.2, 5.6 and 9.0±0.3 degrees 2 theta at a Cu—K$_\alpha$ radiation, λ=1.5406 Å. Specifically, the cocrystal Form XII of the present invention is characterized by exhibiting in the X-ray powder diffractogram a pattern of peaks, expressed in 2 theta units in degrees, 2θ (°), which is shown in Table 12.

TABLE 12

List of selected peaks (only peaks with relative intensity greater than or equal to 1% are indicated):

| Pos. [°2θ] | d-spacing [Å] | Rel. Int. [%] |
| --- | --- | --- |
| 4.2 | 20.97 | 73 |
| 5.6 | 15.87 | 100 |
| 6.2 | 14.23 | 11 |
| 7.2 | 12.35 | 8 |
| 7.4 | 11.93 | 3 |
| 7.7 | 11.48 | 16 |
| 8.5 | 10.36 | 12 |
| 9.0 | 9.80 | 21 |
| 9.4 | 9.37 | 16 |
| 10.6 | 8.34 | 44 |
| 11.1 | 7.99 | 41 |
| 11.4 | 7.78 | 19 |
| 11.8 | 7.53 | 21 |

TABLE 12-continued

List of selected peaks (only peaks with relative intensity greater than or equal to 1% are indicated):

| Pos. [°2θ] | d-spacing [Å] | Rel. Int. [%] |
|---|---|---|
| 12.4 | 7.17 | 24 |
| 12.9 | 6.88 | 17 |
| 13.3 | 6.64 | 8 |
| 13.7 | 6.45 | 7 |
| 14.2 | 6.24 | 16 |
| 14.5 | 6.11 | 10 |
| 14.8 | 6.00 | 9 |
| 15.2 | 5.81 | 4 |
| 15.5 | 5.71 | 4 |
| 16.1 | 5.51 | 13 |
| 16.7 | 5.30 | 9 |
| 16.9 | 5.25 | 19 |
| 17.2 | 5.15 | 6 |
| 18.2 | 4.87 | 31 |
| 19.0 | 4.68 | 15 |
| 19.2 | 4.62 | 7 |
| 19.5 | 4.55 | 7 |
| 19.8 | 4.49 | 10 |
| 20.8 | 4.27 | 9 |
| 21.3 | 4.17 | 18 |
| 21.6 | 4.12 | 17 |
| 21.9 | 4.05 | 10 |
| 22.2 | 4.00 | 6 |
| 23.0 | 3.87 | 5 |
| 23.7 | 3.75 | 6 |
| 24.5 | 3.63 | 4 |

Figure 22:
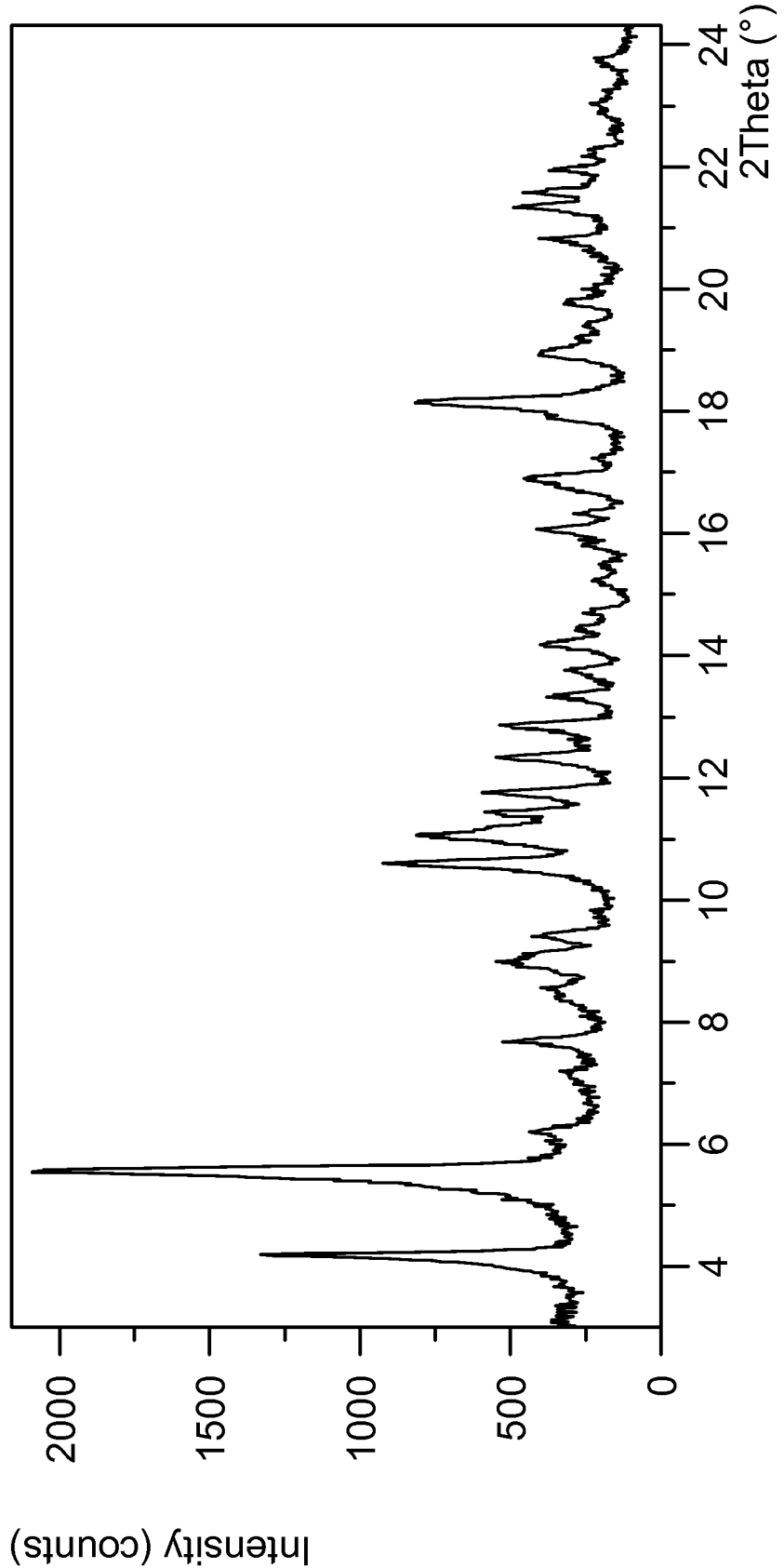
FIG. 22 shows the X-ray powder diffractogram (XRPD) of the cocrystal Form XII. The spectrum expresses intensity (I; counts) versus degrees 2 theta (°).

The cocrystal Form XII of the present invention may be further characterized by an X-ray diffractogram as in FIG. 22.

The cocrystal Form XII of the present invention may also be further characterized by the following 1H NMR spectrum (CDCl$_3$, 400 MHz, δ): 8.17 (m, 1 H); 7.15-7.13 (m, 1H), 7.07-7.05 (m, 1H); 6.43-6.42 (m, 1H); 6.31-6.30 (m, 1H); 4.06-4.02 (m, 1H); 3.45-3.27 (m, 2H); 2.50 (t, J=7.8 Hz, 2H); 2.41-2.32 (m, 4H); 2.19-2.11 (m, 1H); 2.05-1.98 (m, 1H); 1.89-1.80 (m, 1H); 1.36-1.26 (m, 9H), 0.98 (t, J=6.8 Hz, 3 H).

Figure 23:
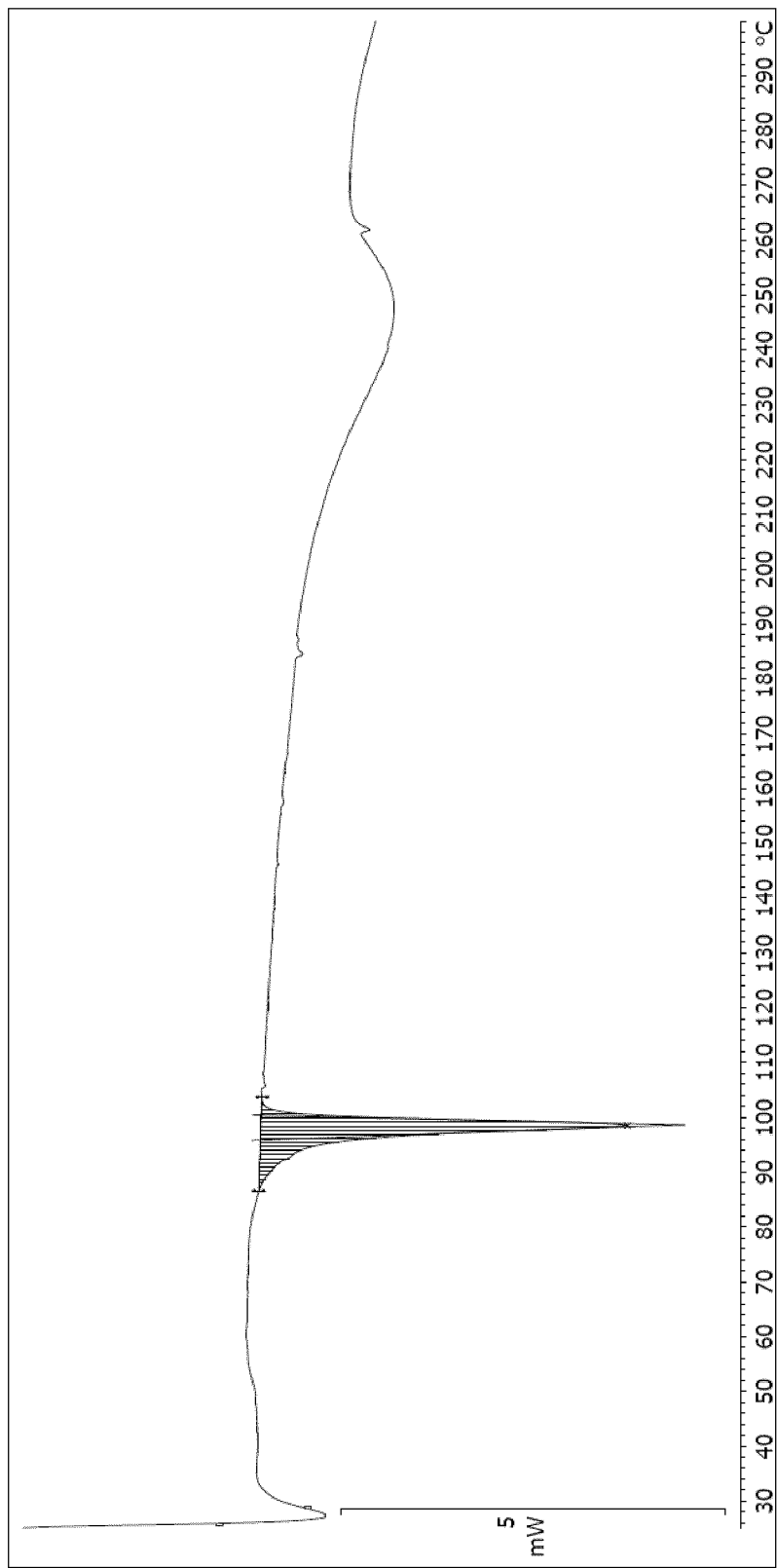
FIG. 23 shows the DSC of cocrystal Form XII. The spectrum expresses the heat flow (mW/mg) versus temperature (° C.).

The cocrystal Form XII of the present invention may also be further characterized by DSC (differential scanning calorimetry) analysis as shown in FIG. 23. The DSC analysis of cocrystal Form XII shows a single endothermic event with an onset at 96° C. which might correspond to a melting event. Then, an endothermic peak with an onset at 96° C. might correspond to a melting event. Therefore, DSC confirms that cocrystal Form XII is not a hydrate.

The cocrystal Form XII of the present invention is in a molar ratio 1:1 (CBN:L-proline).

In a particular embodiment, the solid composition comprises a cocrystal wherein the cannabinoid is CBN and L-proline, also named Form XIII.

In an embodiment, the cocrystal Form XIII of the present invention is characterized by having an X-ray powder diffractogram that comprises characteristic peaks at 4.7, 10.9 and 12.5±0.3 degrees 2 theta at a Cu—K$_\alpha$ radiation, λ=1.5406 Å. Specifically, the cocrystal Form XIII of the present invention is characterized by exhibiting in the X-ray powder diffractogram a pattern of peaks, expressed in 2 theta units in degrees, 2θ (°), which is shown in Table 13.

TABLE 13

List of selected peaks (only peaks with relative intensity greater than or equal to 1% are indicated):

| Pos. [°2Th.] | d-spacing [Å] | Rel. Int. [%] |
|---|---|---|
| 4.7 | 18.88 | 100 |
| 8.1 | 10.91 | 25 |
| 10.9 | 8.12 | 24 |
| 12.5 | 7.11 | 13 |
| 13.6 | 6.51 | 7 |
| 14.1 | 6.27 | 4 |
| 15.9 | 5.57 | 15 |
| 16.3 | 5.43 | 18 |
| 17.0 | 5.21 | 35 |
| 17.3 | 5.13 | 24 |
| 18.9 | 4.69 | 33 |
| 19.7 | 4.50 | 26 |
| 20.6 | 4.31 | 17 |
| 21.4 | 4.16 | 14 |
| 21.7 | 4.09 | 17 |
| 22.9 | 3.89 | 7 |
| 23.4 | 3.80 | 8 |
| 23.9 | 3.72 | 5 |
| 25.7 | 3.46 | 5 |
| 26.3 | 3.38 | 2 |
| 27.1 | 3.30 | 4 |
| 28.5 | 3.13 | 1 |
| 37.5 | 2.40 | 2 |
| 38.1 | 2.36 | 2 |
| 38.1 | 2.36 | 2 |

Figure 24:
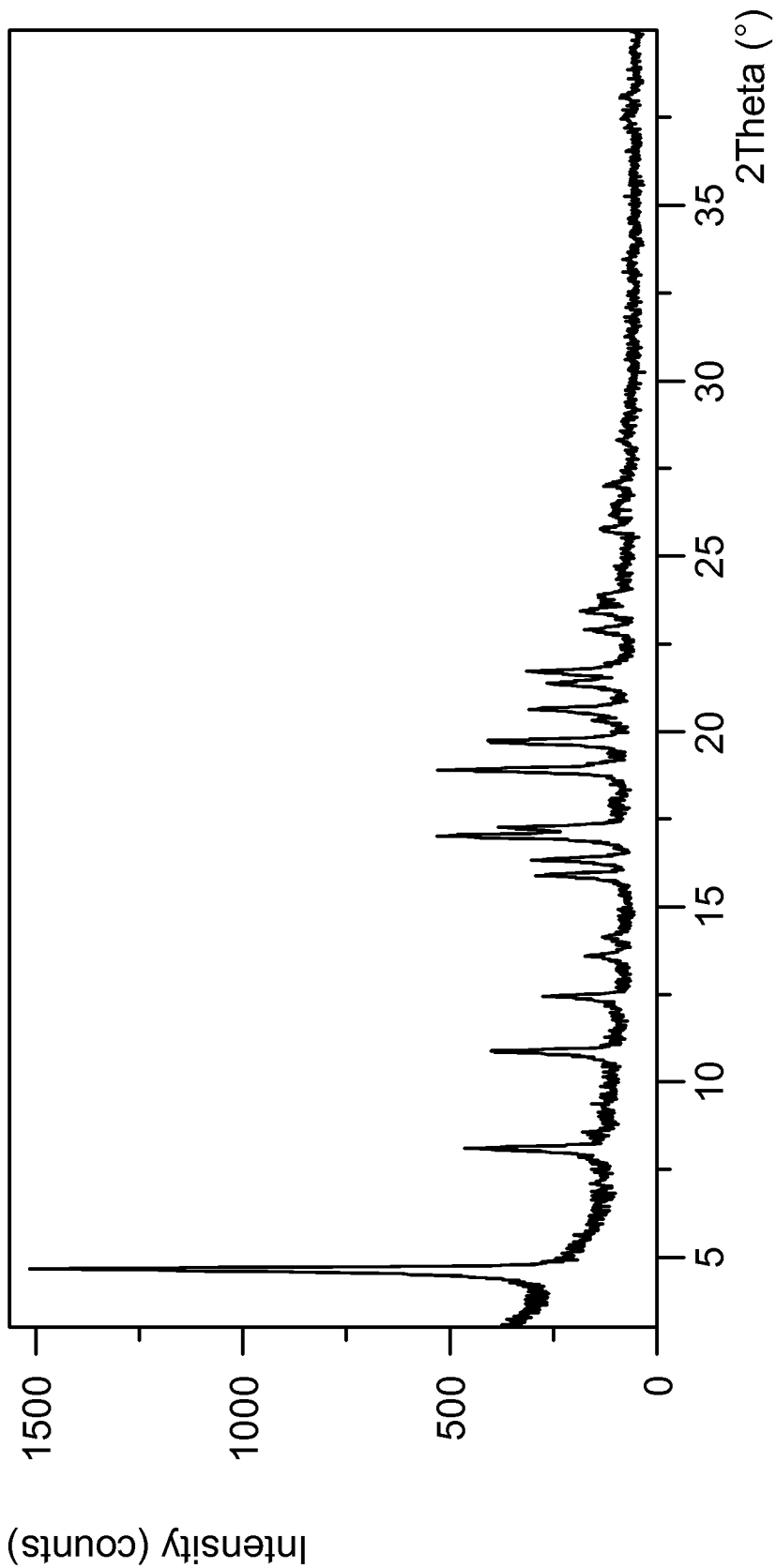
FIG. 24 shows the X-ray powder diffractogram (XRPD) of the cocrystal Form XIII. The spectrum expresses intensity (I; counts) versus degrees 2 theta (°).

The cocrystal Form XIII of the present invention may be further characterized by an X-ray diffractogram as in FIG. 24.

The cocrystal Form XIII of the present invention may also be further characterized by the following 1H NMR spectrum (DMSO-d6, 400 MHz, δ): 9.92 (s br, 1H); 8.29-8.25 (m, 1 H); 7.17 (d, J=7.8 Hz, 1H), 7.05-7.00 (dd, J=1.6, 7.8 Hz, 1H); 6.39 (d, J=1.6 Hz, 1H); 6.23 (d, J=1.6 Hz, 1H), 3.62 (dd, J=5.7, 8.6 Hz, 1H); 3.25-3.16 (m, 1H); 2.99 (dt, J=7.4, 11.3 Hz, 1H); 2.43 (t, J=7.8 Hz, 2 H); 2.30 (s, 3H); 2.06-1.88 (m, 2H); 1.84-1.61 (m, 2H); 1.59-1.49 (m, 2 H); 1.49 (s, 6H), 1.37-1.20 (m, 4H), 0.87 (t, J=7.0 HZ, 3 H).

Figure 25:
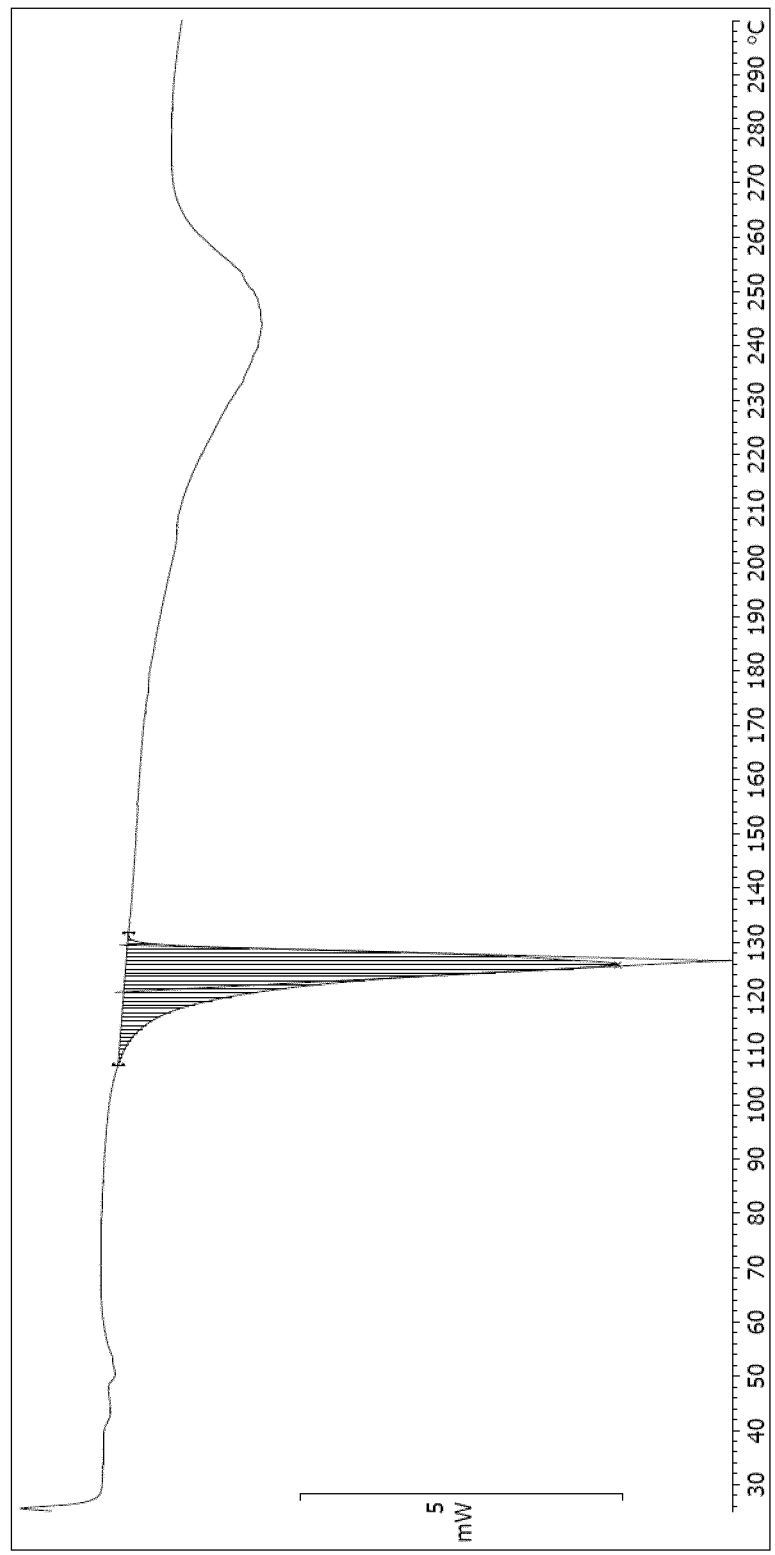
FIG. 25 shows the DSC of cocrystal Form XIII. The spectrum expresses the heat flow (mW/mg) versus temperature (° C.).

The cocrystal Form XIII of the present invention may also be further characterized by DSC (differential scanning calorimetry) analysis as shown in FIG. 25. The DSC analysis of cocrystal Form XIII shows a single endothermic event with an onset at 121° C. which might correspond to a melting event. Then, an endothermic peak with an onset at 121° C. might correspond to a melting event. Therefore, DSC confirms that cocrystal Form XIII is not an hydrate.

The cocrystal Form XIII of the present invention is in a molar ratio 1:1 (CBN:L-proline).

In an embodiment, the cocrystal of Form XIII of the present invention has a purity equal to or higher than 91.5% a/a measured by HPLC (method 2).

In a particular embodiment, the solid composition comprises a cocrystal wherein the cannabinoid is CBN and D-proline, also named Form XIV.

In an embodiment, the cocrystal Form XIV of the present invention is characterized by having an X-ray powder diffractogram that comprises characteristic peaks at 4.7, 10.9 and 12.5±0.3 degrees 2 theta at a Cu—K$_\alpha$ radiation, λ=1.5406 Å. Specifically, the cocrystal Form XIV of the present invention is characterized by exhibiting in the X-ray powder diffractogram a pattern of peaks, expressed in 2 theta units in degrees, 2θ (°), which is shown in Table 14.

TABLE 14

List of selected peaks (only peaks with relative intensity greater than or equal to 1% are indicated):

| Pos. [°2Th.] | d-spacing [Å] | Rel. Int. [%] |
|---|---|---|
| 4.7 | 18.96 | 100 |
| 8.1 | 10.92 | 28 |
| 10.9 | 8.13 | 19 |
| 12.5 | 7.11 | 10 |
| 13.6 | 6.50 | 5 |
| 15.9 | 5.57 | 9 |
| 16.3 | 5.42 | 10 |
| 17.0 | 5.21 | 24 |
| 17.3 | 5.14 | 15 |
| 18.9 | 4.70 | 20 |
| 19.7 | 4.51 | 15 |
| 20.6 | 4.31 | 10 |
| 21.4 | 4.16 | 9 |
| 21.7 | 4.10 | 11 |
| 22.9 | 3.88 | 4 |
| 23.4 | 3.80 | 4 |
| 25.8 | 3.46 | 3 |
| 28.3 | 3.15 | 2 |

Figure 26:
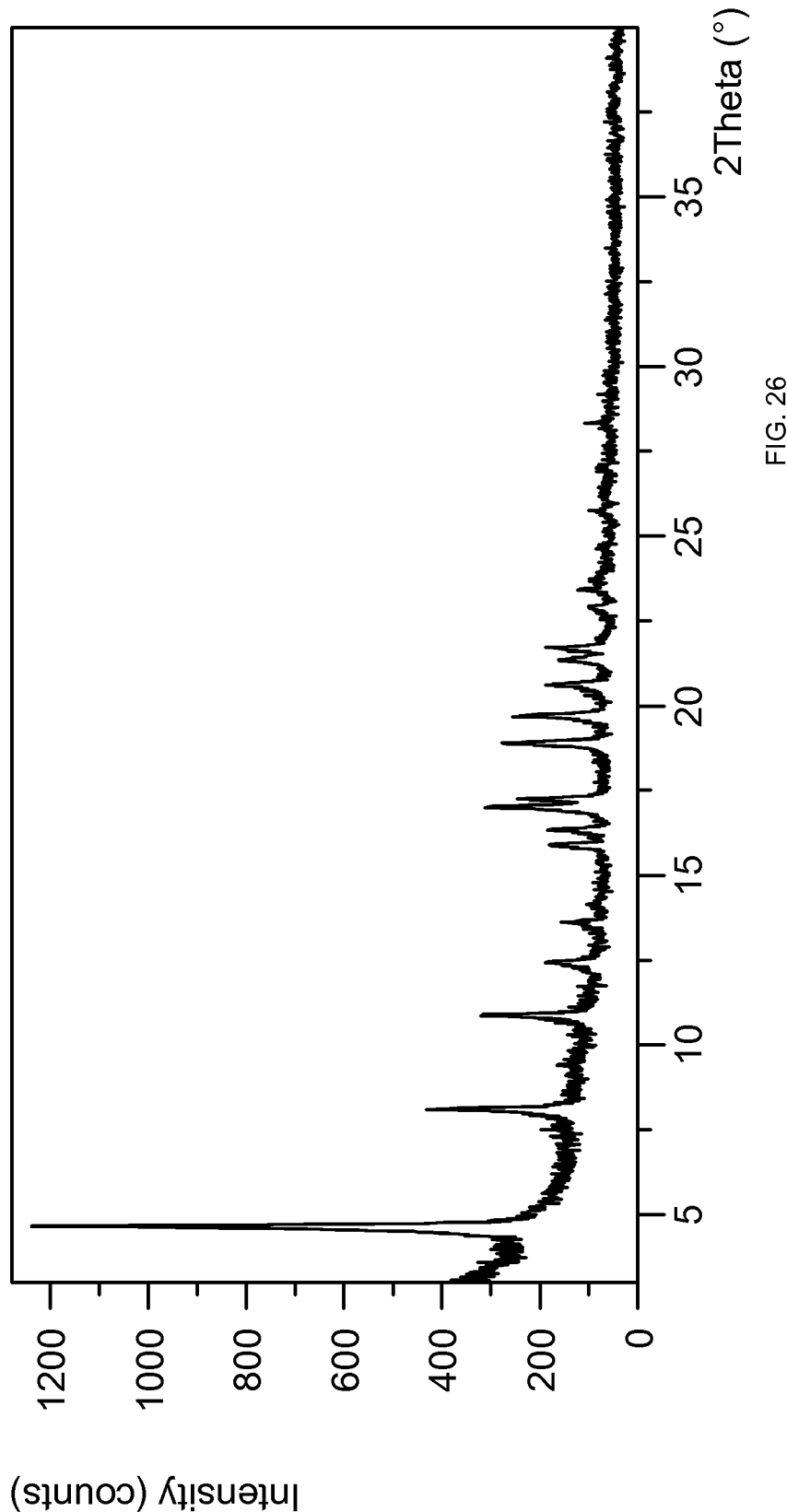
FIG. 26 shows the X-ray powder diffractogram (XRPD) of the cocrystal Form XIV. The spectrum expresses intensity (I; counts) versus degrees 2 theta (°).

The cocrystal Form XIV of the present invention may be further characterized by an X-ray diffractogram as in FIG. 26.

The cocrystal Form XIV of the present invention may also be further characterized by the following 1H NMR spectrum (CDCl$_3$, 400 MHz, δ): 11.42 (s br, 1H); 8.18-8.15 (m, 1 H); 7.14 (d, J=7.8 Hz, 1H), 7.08-7.04 (m, 1H); 6.43 (d, J=1.6 Hz, 1H); 6.30 (d, J=1.6 Hz, 1H); 4.04 (dd, J=5.5, 8.6 Hz, 1H); 3.47-3.22 (m, 2H); 2.50 (t, J=7.8 Hz, 2H); 2.38 (s, 3H); 2.40-2.31 (m, 1H); 2.19-2.08 (m, 1H); 2.19-2.08 (m, 1H); 2.08-1.96 (m, 1H); 1.92-1.76 (m, 1H); 1.59 (s, 6H), 1.38-1.28 (m, 4H), 0.89 (t, J=7.0 HZ, 3 H).

Figure 27:
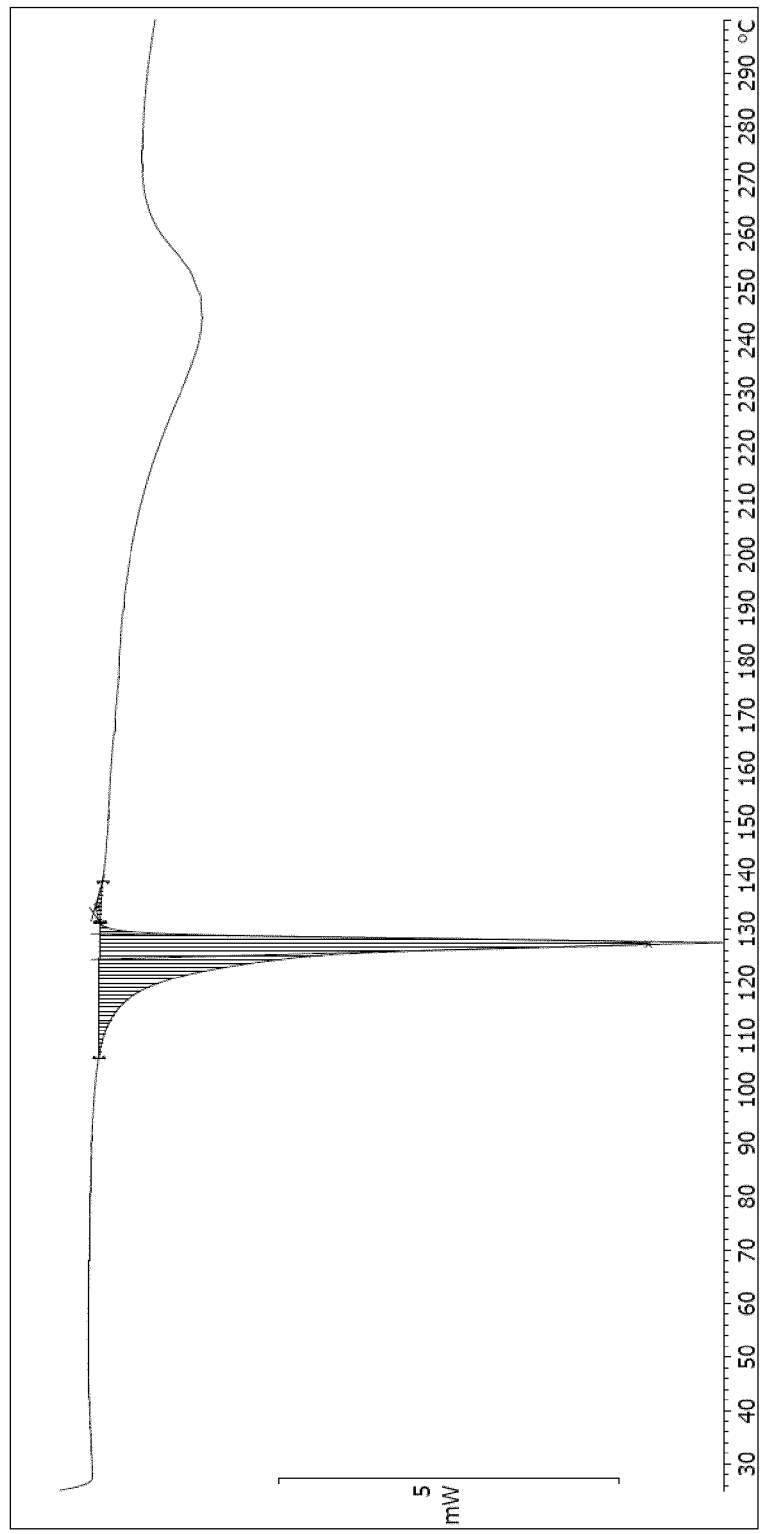
FIG. 27 shows the DSC of cocrystal Form XIV. The spectrum expresses the heat flow (mW/mg) versus temperature (° C.).

The cocrystal Form XIV of the present invention may also be further characterized by DSC (differential scanning calorimetry) analysis as shown in FIG. 27. The DSC analysis of cocrystal Form XIV shows a single endothermic event with an onset at 124° C. which might correspond to a melting event. Then, a small exothermic event partially overlapped with the first endothermic event is observed (131° C.) which nature is unknown.

The cocrystal Form XIV of the present invention is in a molar ratio 1:1 (CBN:D-proline).

In an embodiment, the cocrystal of Form XIV of the present invention has a purity equal to or higher than 90.5% a/a measured by HPLC (method 2).

In a particular embodiment, the solid composition comprises a cocrystal wherein the cannabinoid is CBN and D-proline, also named Form XV.

In an embodiment, the cocrystal Form XV of the present invention is characterized by having an X-ray powder diffractogram that comprises characteristic peaks at 5.1, 10.2 and 16.1±0.3 degrees 2 theta at a Cu—K$_\alpha$ radiation, λ=1.5406 Å. Specifically, the cocrystal Form XV of the present invention is characterized by exhibiting in the X-ray powder diffractogram a pattern of peaks, expressed in 2 theta units in degrees, 2θ (°), which is shown in Table 15.

TABLE 15

List of selected peaks (only peaks with relative intensity greater than or equal to 1% are indicated):

| Pos. [°2θ] | d-spacing [Å] | Rel. Int. [%] |
|---|---|---|
| 5.1 | 17.40 | 100 |
| 8.6 | 10.23 | 2 |
| 10.2 | 8.71 | 15 |
| 11.3 | 7.84 | 9 |
| 12.5 | 7.10 | 13 |
| 14.4 | 6.14 | 6 |
| 15.3 | 5.80 | 6 |
| 16.1 | 5.50 | 20 |
| 17.7 | 5.02 | 6 |
| 18.4 | 4.83 | 24 |
| 19.1 | 4.64 | 6 |
| 20.4 | 4.36 | 17 |
| 21.7 | 4.10 | 7 |
| 22.4 | 3.97 | 4 |
| 22.9 | 3.89 | 3 |
| 24.1 | 3.70 | 5 |
| 25.2 | 3.54 | 3 |
| 25.7 | 3.47 | 2 |
| 27.2 | 3.28 | 2 |
| 28.7 | 3.11 | 1 |
| 30.9 | 2.90 | 1 |

Figure 28:
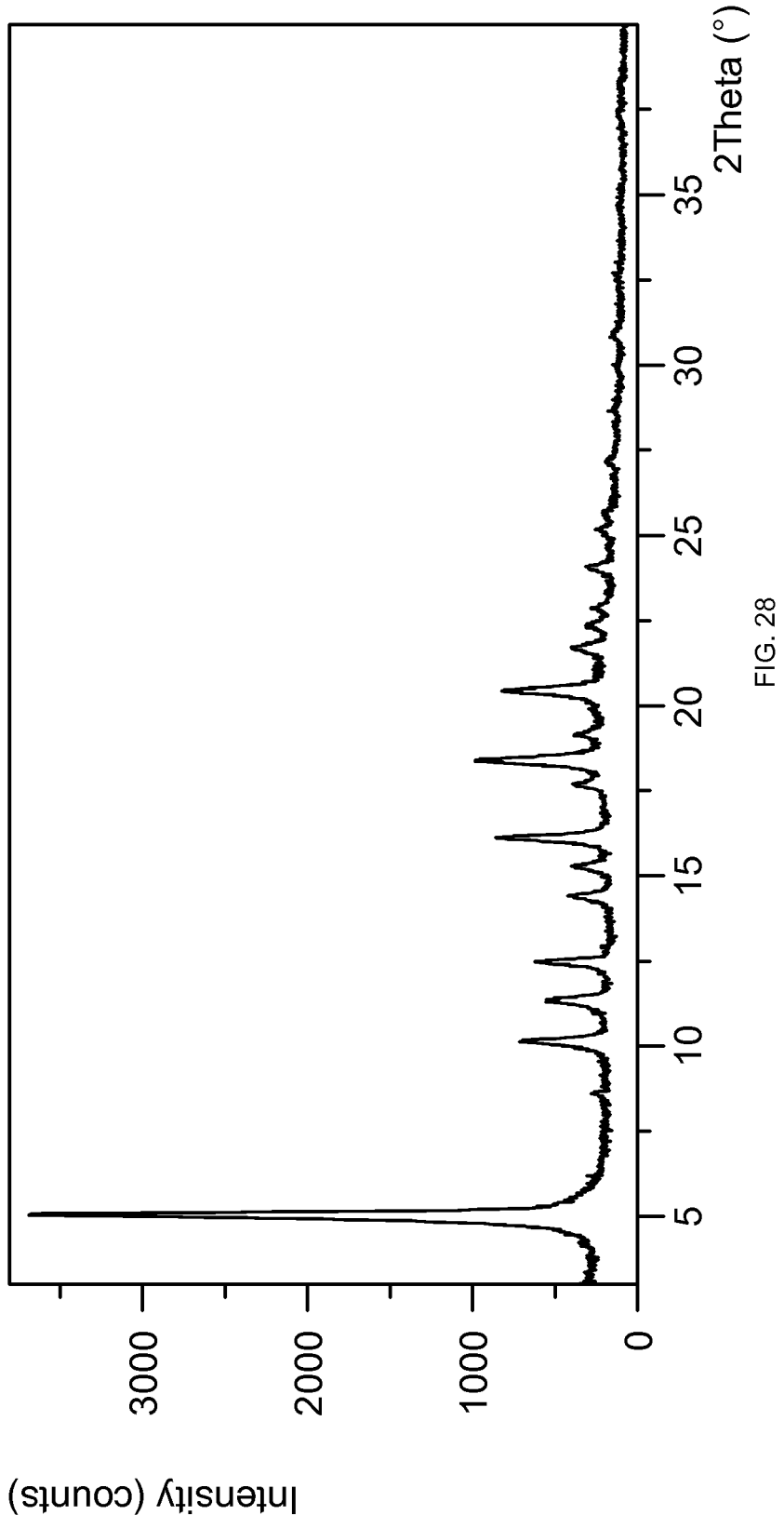
FIG. 28 shows the X-ray powder diffractogram (XRPD) of the cocrystal Form XV. The spectrum expresses intensity (I; counts) versus degrees 2 theta (°).

The cocrystal Form XV of the present invention may be further characterized by an X-ray diffractogram as in FIG. 28.

The cocrystal Form XV of the present invention may also be further characterized by the following 1H NMR spectrum (CDCl$_3$, 400 MHz, δ): 8.17 (2, 1 H); 7.15-7.13 (m, 1H), 7.07-7.05 (m, 1H); 6.43-6.42 (m, 1H); 6.31-6.30 (m, 1H); 4.09-4.02 (m, 1H); 3.45-3.27 (m, 2H); 2.50 (t, J=7.8 Hz, 2H); 2.41-2.32 (m, 4H); 2.19-2.11 (m, 1H); 2.08-1.97 (m, 1H); 1.89-1.80 (m, 1H); 1.34-1.23 (m, 9H), 0.91-0.85 (m, 3 H).

Figure 29:
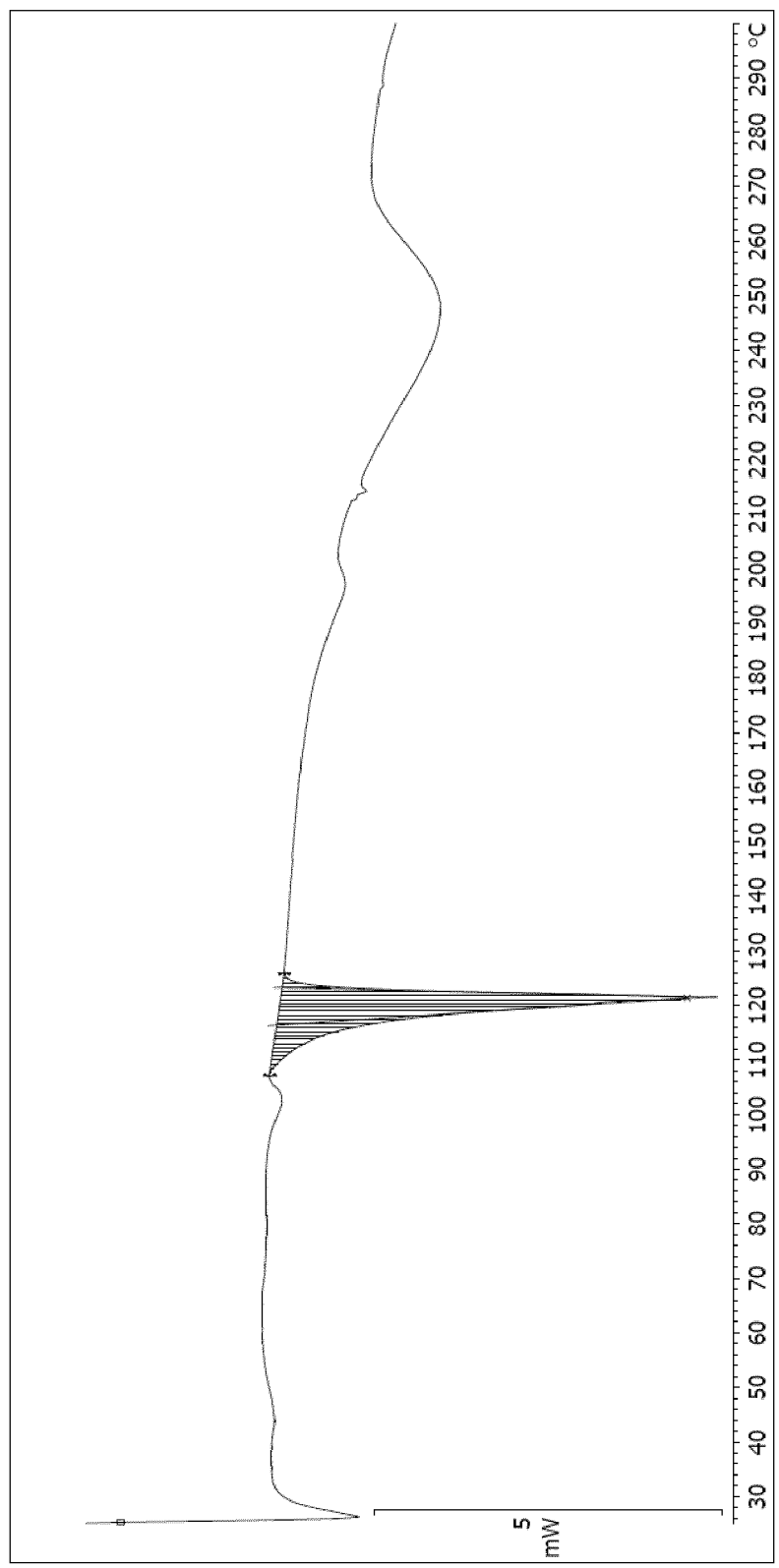
FIG. 29 shows the DSC of cocrystal Form XV. The spectrum expresses the heat flow (mW/mg) versus temperature (° C.).

The cocrystal Form XV of the present invention may also be further characterized by DSC (differential scanning calorimetry) analysis as shown in FIG. 29. The DSC analysis of cocrystal Form XV shows a single endothermic event at 116° C. which might correspond to the melting.

The cocrystal Form XV of the present invention is in a molar ratio 1:1 (CBN:D-proline).

In a particular embodiment, the solid composition comprises a cocrystal wherein the cannabinoid is CBG.

In a particular embodiment, the solid composition comprises a cocrystal wherein the cannabinoid is CBG and betaine, also named Form XVI.

In an embodiment, the cocrystal Form XVI of the present invention is characterized by having an X-ray powder diffractogram that comprises characteristic peaks at 7.8, 15.8 and 23.8±0.3 degrees 2 theta at a Cu—K$_\alpha$ radiation, λ=1.5406 Å. Specifically, the cocrystal Form XVI of the present invention is characterized by having an X-ray powder diffractogram that comprises further characteristic peaks at 18.0, 18.5 and 23.5±0.3 degrees 2 theta at a Cu—K$_\alpha$ radiation, λ=1.5406 Å. More specifically, the cocrystal Form XVI of the present invention is characterized by exhibiting in the X-ray powder diffractogram a pattern of peaks, expressed in 2 theta units in degrees, 2θ (°), which is shown in Table 16.

TABLE 16

List of selected peaks (only peaks with relative intensity greater than or equal to 1% are indicated):

| Pos. [°2θ] | d-spacing [Å] | Rel. Int. [%] |
| --- | --- | --- |
| 7.8 | 11.3 | 100 |
| 8.3 | 10.7 | 1 |
| 12.5 | 7.1 | 1 |
| 15.8 | 5.6 | 48 |
| 16.2 | 5.5 | 3 |
| 16.9 | 5.2 | 1 |
| 18.0 | 4.9 | 3 |
| 18.5 | 4.8 | 2 |
| 18.9 | 4.7 | 3 |
| 19.7 | 4.5 | 1 |
| 20.4 | 4.4 | 1 |
| 22.0 | 4.0 | 1 |
| 22.5 | 4.0 | 3 |
| 23.2 | 3.8 | 1 |
| 23.5 | 3.8 | 4 |
| 23.8 | 3.7 | 15 |
| 24.1 | 3.7 | 1 |
| 24.6 | 3.6 | 1 |
| 25.2 | 3.5 | 1 |
| 25.7 | 3.5 | 1 |
| 39.3 | 2.3 | 1 |

Figure 30:
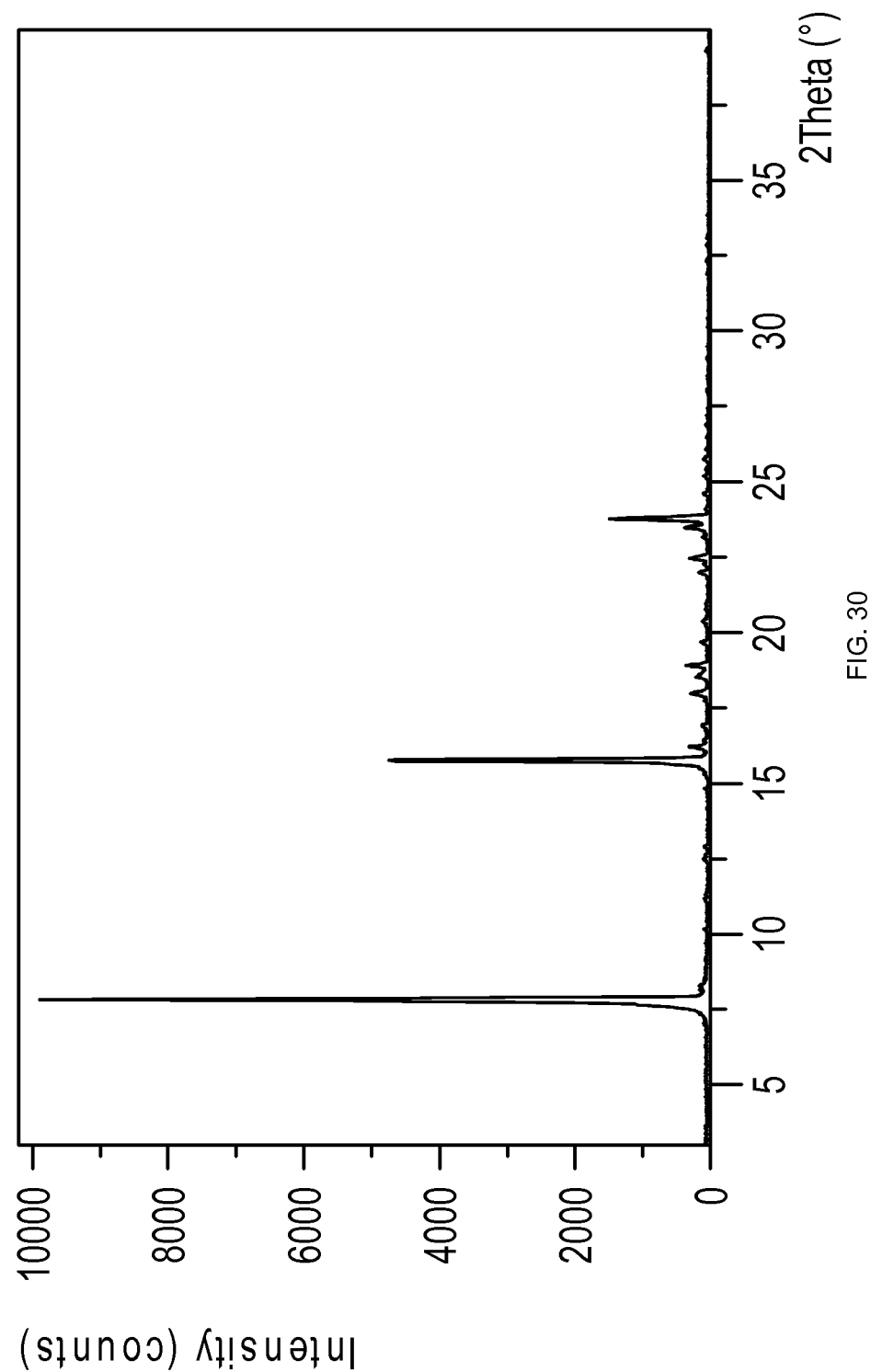
FIG. 30 shows the X-ray powder diffractogram (XRPD) of the cocrystal Form XVI. The spectrum expresses intensity (I; counts) versus degrees 2 theta (°).

The cocrystal Form XVI of the present invention may be further characterized by an X-ray diffractogram as in FIG. 30.

The cocrystal Form XVI of the present invention may also be further characterized by the following 1H NMR spectrum (CDCl$_3$, 400 MHz, δ): 6.14 (s, 2H); 5.30-5.18 (m, 1H); 5.14-5.01 (m, 1H); 3.83 (s, 2H); 3.29-3.18 (m, 11H); 2.40 (t, 2H, J=7.8 Hz); 2.11-2.00 (m, 2H); 1.98-1.88 (m, 2H); 1.75 (s, 3H); 1.66-1.48 (m, 8H); 1.40-1.23 (m, 4H); 0.90 (t, 3H, J=7.0 Hz).

Figure 31:
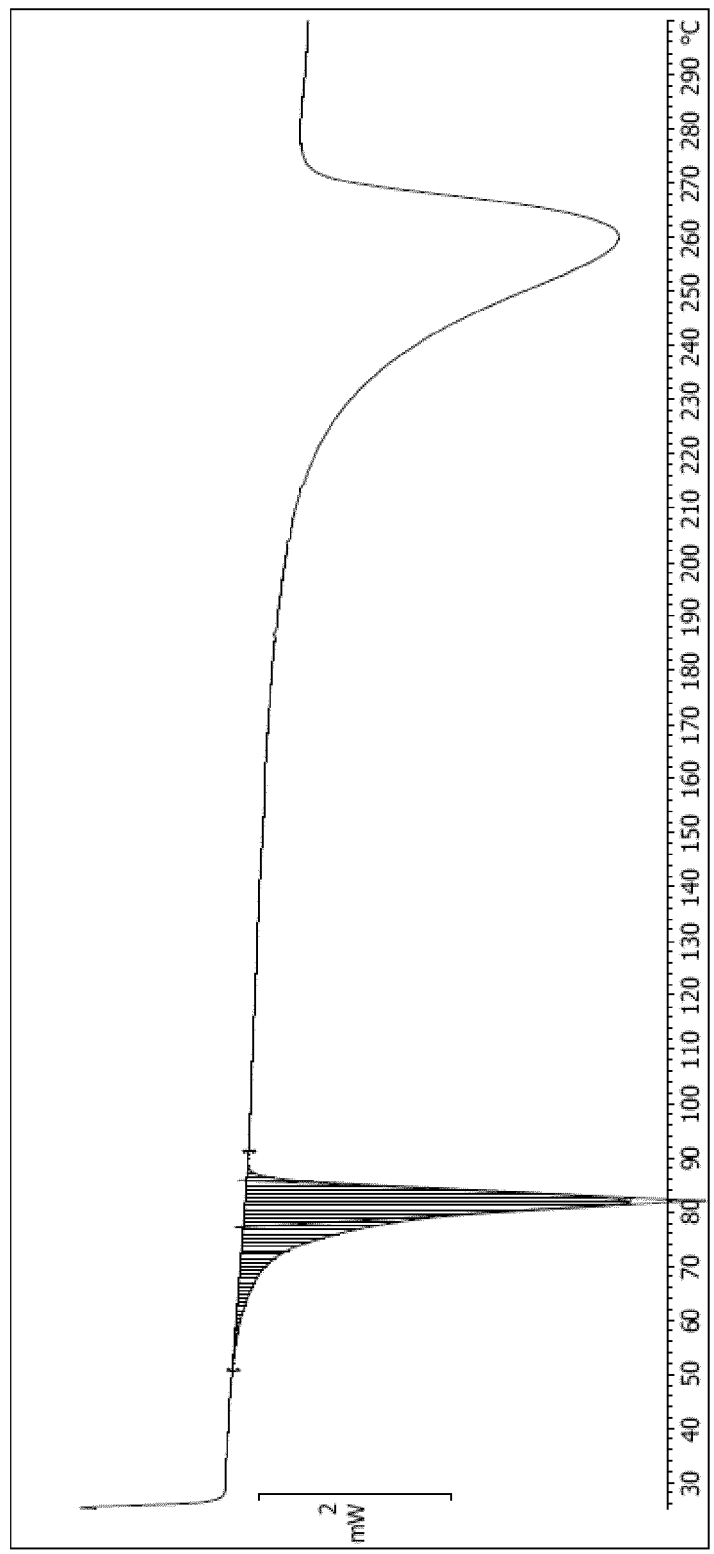
FIG. 31 shows the DSC of cocrystal Form XVI. The spectrum expresses the heat flow (mW/mg) versus temperature (° C.).

The cocrystal Form XVI of the present invention may also be further characterized by DSC (differential scanning calorimetry) analysis as shown in FIG. 31. The DSC analysis of cocrystal Form XVI shows an endothermic event with an onset at 77.2° C. that should correspond to the melting of the cocrystal. It is worth noting that melting onset of Form XVI is higher than that observed for CBG crystalline form (50.9° C.).

The cocrystal Form XVI of the present invention is in a molar ratio 1:1 (CBG:betaine).

In a particular embodiment, the solid composition comprises a cocrystal wherein the cannabinoid is CBG and L-carnitine, also named Form XVII.

In an embodiment, the cocrystal Form XVII of the present invention is characterized by having an X-ray powder diffractogram that comprises characteristic peaks at 7.0, 14.1 and 19.8±0.3 degrees 2 theta at a Cu—K$_\alpha$ radiation, λ=1.5406 Å. Specifically, the cocrystal Form XVII of the present invention is characterized by having an X-ray powder diffractogram that comprises further characteristic peaks at 17.6, 18.9 and 22.4±0.3 degrees 2 theta at a Cu—K$_\alpha$ radiation, λ=1.5406 Å. More specifically, the cocrystal Form XVII of the present invention is characterized by exhibiting in the X-ray powder diffractogram a pattern of peaks, expressed in 2 theta units in degrees, 2θ (°), which is shown in Table 17.

TABLE 17

List of selected peaks (only peaks with relative intensity greater than or equal to 1% are indicated):

| Pos. [°2θ] | d-spacing [Å] | Rel. Int. [%] |
| --- | --- | --- |
| 7.0 | 12.6 | 100 |
| 12.7 | 7.0 | 1 |
| 14.1 | 6.3 | 13 |
| 15.6 | 5.7 | 2 |
| 17.6 | 5.0 | 6 |
| 18.9 | 4.7 | 6 |
| 19.8 | 4.5 | 10 |
| 21.3 | 4.2 | 5 |
| 22.4 | 4.0 | 4 |

Figure 32:
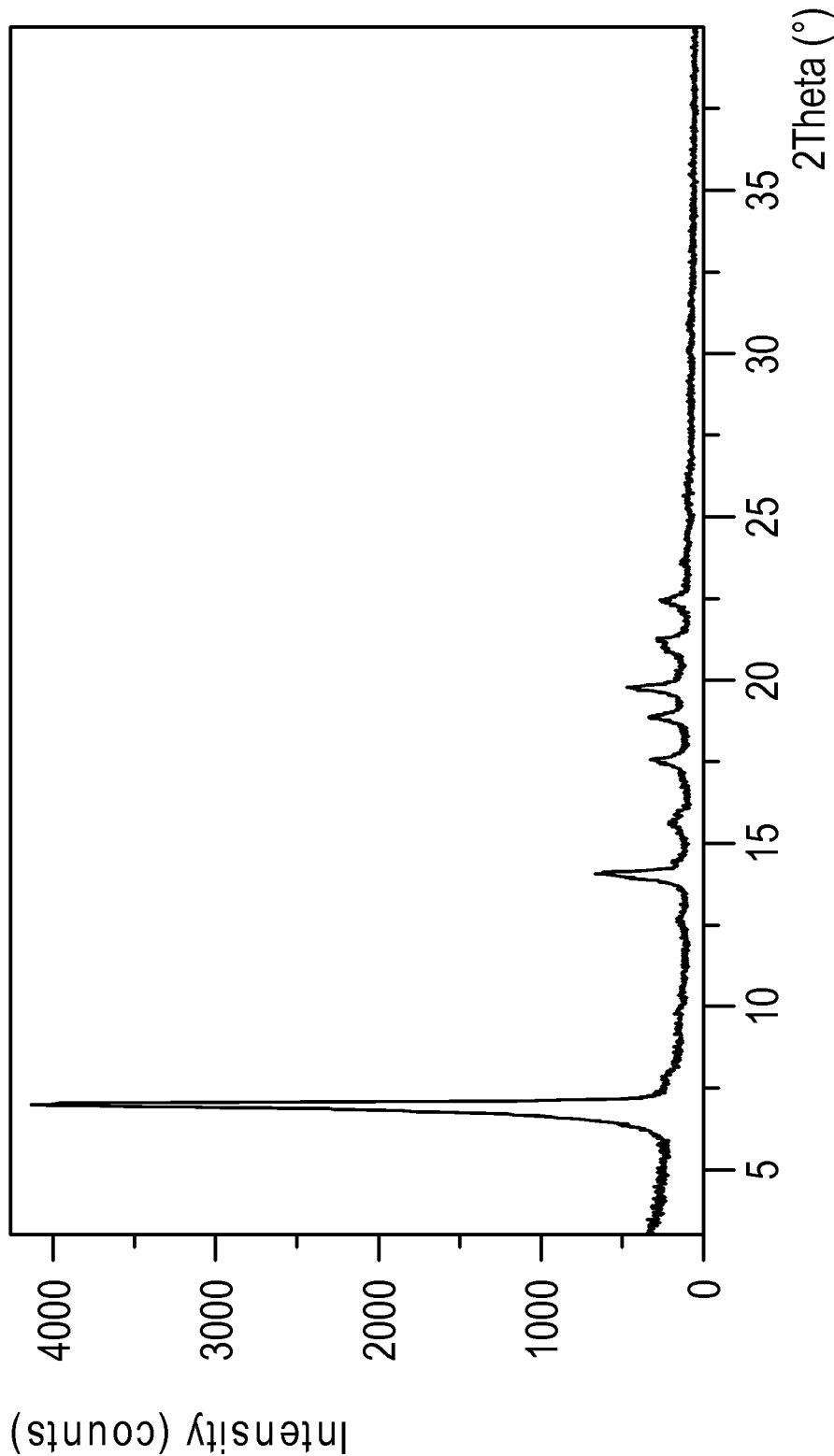
FIG. 32 shows the X-ray powder diffractogram (XRPD) of the cocrystal Form XVII. The spectrum expresses intensity (I; counts) versus degrees 2 theta (°).

The cocrystal Form XVII of the present invention may be further characterized by an X-ray diffractogram as in FIG. 32.

The cocrystal Form XVII of the present invention may also be further characterized by the following 1H NMR spectrum (CDCl$_3$, 400 MHz, δ): 6.14 (s, 2H); 5.29-5.18 (m, 1H); 5.12-5.02 (m, 1H); 4.51-4.39 (m, 1H); 3.44-3.07 (m, 13H); 2.48-2.26 (m, 4H); 2.12-1.99 (m, 2H); 1.98-1.87 (m, 2H); 1.75 (s, 3H); 1.70-1.49 (m, 8H); 1.43-1.23 (m, 4H); 0.90 (t, 3H, J=7.0 Hz).

Figure 33:
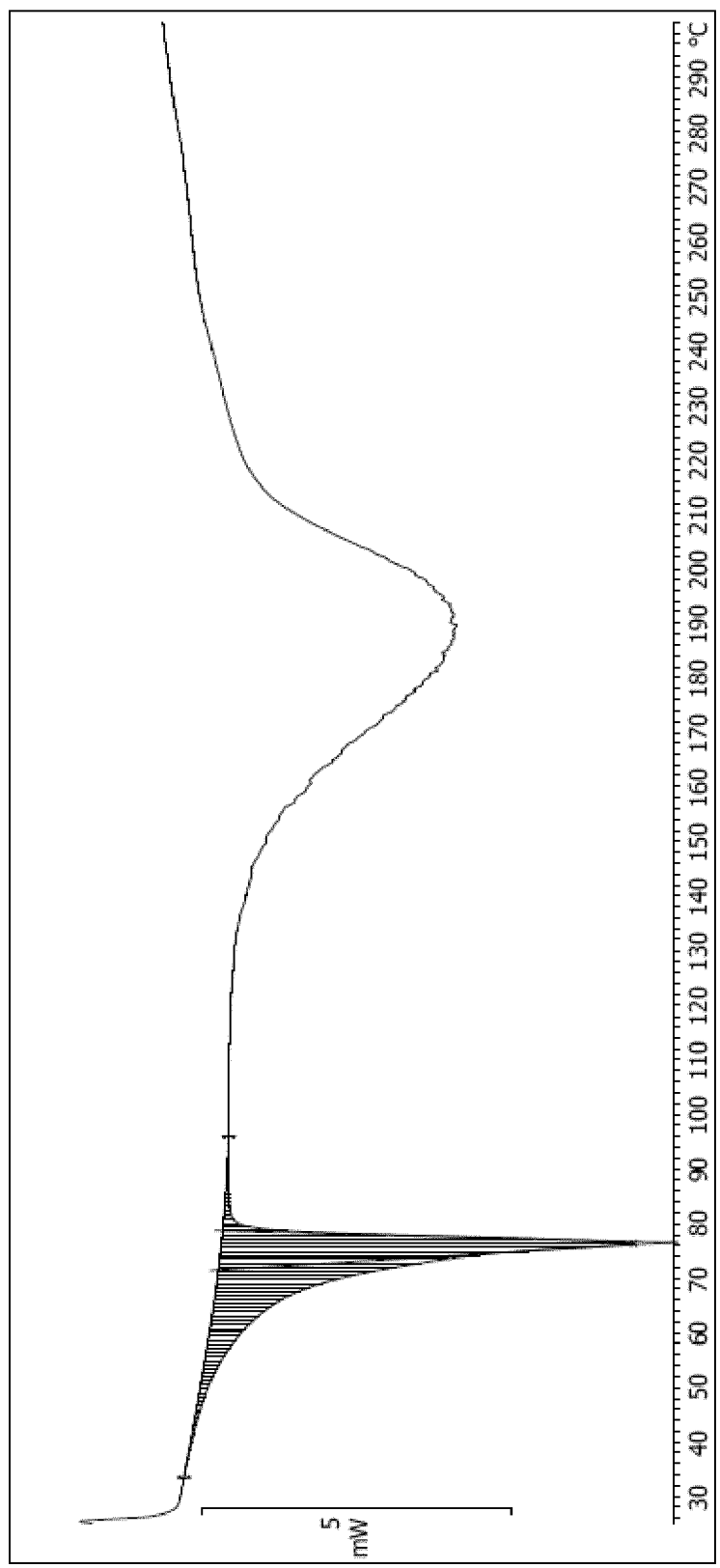
FIG. 33 shows the DSC of cocrystal Form XVII. The spectrum expresses the heat flow (mW/mg) versus temperature (° C.).

The cocrystal Form XVII of the present invention may also be further characterized by DSC (differential scanning calorimetry) analysis as shown in FIG. 33. The DSC analysis of cocrystal Form XVII shows an endothermic event with an onset at 71.4° C. that should correspond to the melting of the cocrystal. It is worth noting that melting onset of form XVI is higher than that observed for CBG crystalline form (50.9° C.).

The cocrystal Form XVII of the present invention is in a molar ratio 1:1 (CBG:L-carnitine).

In an embodiment, the cocrystal of Form XVII of the present invention has a purity equal to or higher than 96.5% a/a measured by HPLC (method 2).

In a particular embodiment, the solid composition comprises a cocrystal wherein the cannabinoid is CBDV and L-proline, also named Form XVIII.

In an embodiment, the cocrystal Form XVIII of the present invention is characterized by having an X-ray powder diffractogram that comprises characteristic peaks at 6.1, 9.8 and 12.0±0.3 degrees 2 theta at a Cu—K$_\alpha$ radiation, λ=1.5406 Å. Specifically, the cocrystal Form XVIII of the present invention is characterized by having an X-ray powder diffractogram that comprises further characteristic peaks at 15.8 and 22.0±0.3 degrees 2 theta at a Cu—K$_\alpha$ radiation, λ=1.5406 Å. More specifically, the cocrystal Form XVIII of the present invention is characterized by exhibiting in the X-ray powder diffractogram a pattern of peaks, expressed in 2 theta units in degrees, 2θ (°), which is shown in Table 18.

TABLE 18

List of selected peaks (only peaks with relative intensity greater than or equal to 1% are indicated):

| Pos. [°2θ] | d-spacing [Å] | Rel. Int. [%] |
| --- | --- | --- |
| 4.3 | 20.5 | 6 |
| 6.1 | 14.4 | 100 |
| 8.7 | 10.2 | 5 |
| 9.8 | 9.1 | 25 |
| 10.3 | 8.6 | 4 |
| 11.5 | 7.7 | 3 |
| 12.0 | 7.4 | 14 |
| 13.1 | 6.8 | 4 |

TABLE 18-continued

List of selected peaks (only peaks with relative intensity greater than or equal to 1% are indicated):

| Pos. [°2θ] | d-spacing [Å] | Rel. Int. [%] |
|---|---|---|
| 13.8 | 6.4 | 5 |
| 14.9 | 6.0 | 3 |
| 15.3 | 5.8 | 1 |
| 15.8 | 5.6 | 12 |
| 16.1 | 5.5 | 7 |
| 16.9 | 5.2 | 3 |
| 17.5 | 5.1 | 4 |
| 18.3 | 4.8 | 13 |
| 19.4 | 4.6 | 6 |
| 19.6 | 4.5 | 7 |
| 20.2 | 4.4 | 4 |
| 21.6 | 4.1 | 1 |
| 22.0 | 4.0 | 10 |
| 23.1 | 3.9 | 4 |
| 23.9 | 3.7 | 5 |
| 24.2 | 3.7 | 1 |
| 24.8 | 3.6 | 1 |
| 25.4 | 3.5 | 2 |
| 26.3 | 3.4 | 4 |
| 27.0 | 3.3 | 5 |
| 28.3 | 3.2 | 1 |
| 31.0 | 2.9 | 5 |

Figure 34:
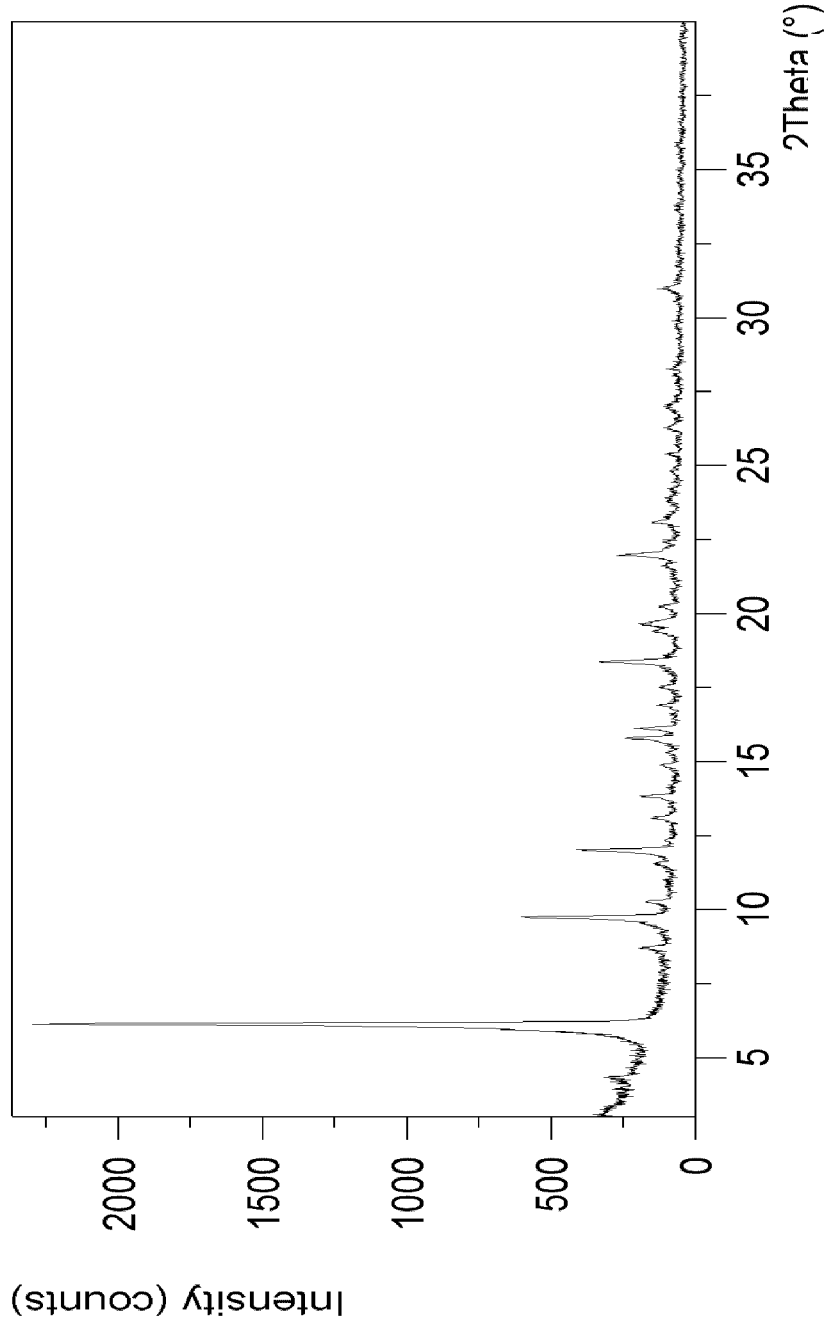
FIG. 34 shows the X-ray powder diffractogram (XRPD) of the cocrystal Form XVIII. The spectrum expresses intensity (I; counts) versus degrees 2 theta (°).

The cocrystal Form XVIII of the present invention may be further characterized by an X-ray diffractogram as in FIG. 34.

The cocrystal Form XVIII of the present invention may also be further characterized by the following 1H NMR spectrum (DMSO·d6, 400 MHz) δ): 8.72 (s, 2H), 6.10-5.93 (m, 2H, ArH), 5.08 (s, 1H), 4.57-4.32 (m, 2H), 3.88-3.77 (d, J=8.4 Hz, 1H), 3.70-3.56 (dd, J=8.7, 5.7 Hz, 2H), 3.25-3.12 (m, 2H), 3.09-2.93 (m, 4H), 2.31-2.24 (m, 2H), 2.17-1.87 (m, 6H), 1.84-1.36 (m, 16H), 0.95-0.59 (m, 4H).

Figure 35:
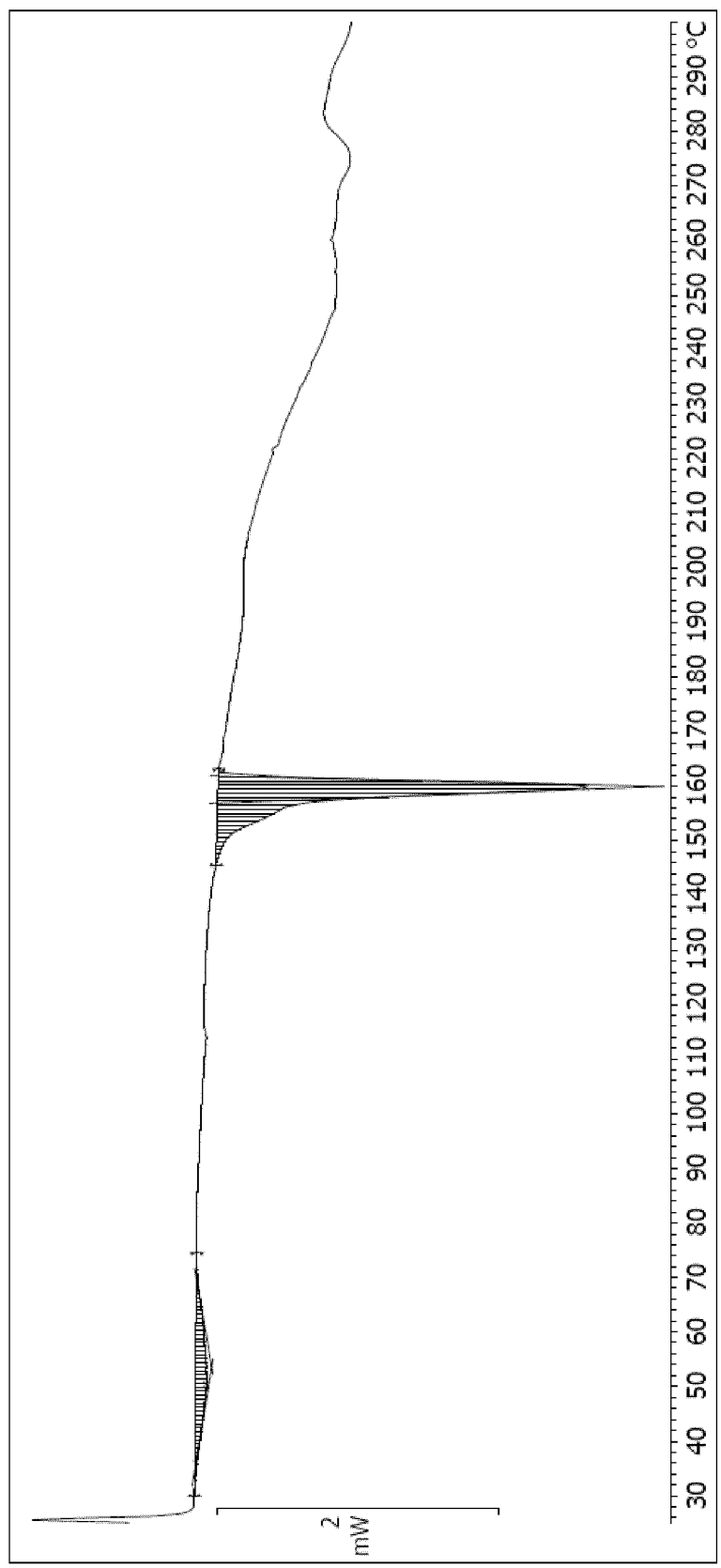
FIG. 35 shows the DSC of cocrystal Form XVIII. The spectrum expresses the heat flow (mW/mg) versus temperature (° C.).

The cocrystal Form XVIII of the present invention may also be further characterized by DSC (differential scanning calorimetry) analysis as shown in FIG. 35. The DSC analysis of cocrystal Form XVIII shows a first endothermic event with an onset at ca. 33° C. followed by a second endothermic event with an onset at ca. 157° C. that should correspond to the melting of the cocrystal Form XVIII. The first event should correspond to the evaporation of residual solvent because Cocrystal Form XVIII remained stable after a heating up to 90° C. and DSC experiments indicated that this event is not reversible.

The cocrystal Form XVIII of the present invention is in a molar ratio 1:1 (CBDV:L-proline).

In an embodiment, the cocrystal of Form XVIII of the present invention has a purity equal to or higher than 99.0% a/a measured by HPLC (method 2).

In a particular embodiment, the solid composition comprises a cocrystal wherein the cannabinoid is CBDV and L-carnitine, also named Form XIX.

In an embodiment, the cocrystal Form XIX of the present invention is characterized by having an X-ray powder diffractogram that comprises characteristic peaks at 6.9, 10.6 and 11.1±0.3 degrees 2 theta at a Cu—K$_\alpha$ radiation, λ=1.5406 Å. Specifically, the cocrystal Form XIX of the present invention is characterized by having an X-ray powder diffractogram that comprises further characteristic peaks at 13.7 and 14.5±0.3 degrees 2 theta at a Cu—K$_\alpha$ radiation, λ=1.5406 Å. More specifically, the cocrystal Form XIX of the present invention is characterized by exhibiting in the X-ray powder diffractogram a pattern of peaks, expressed in 2 theta units in degrees, 2θ (°), which is shown in Table 19.

TABLE 19

List of selected peaks (only peaks with relative intensity greater than or equal to 1% are indicated):

| Pos. [°2θ] | d-spacing [Å] | Rel. Int. [%] |
|---|---|---|
| 6.9 | 12.9 | 100 |
| 9.3 | 9.5 | 12 |
| 10.1 | 8.8 | 4 |
| 10.6 | 8.4 | 37 |
| 11.1 | 7.9 | 55 |
| 12.0 | 7.4 | 12 |
| 13.1 | 6.8 | 3 |
| 13.7 | 6.4 | 29 |
| 14.5 | 6.1 | 23 |
| 14.9 | 6.0 | 9 |
| 15.0 | 5.9 | 2 |
| 15.4 | 5.8 | 5 |
| 15.8 | 5.6 | 35 |
| 15.9 | 5.6 | 84 |
| 17.7 | 5.0 | 9 |
| 17.9 | 5.0 | 7 |
| 18.6 | 4.8 | 17 |
| 18.9 | 4.7 | 4 |
| 19.5 | 4.6 | 50 |
| 20.3 | 4.4 | 22 |
| 20.6 | 4.3 | 49 |
| 21.1 | 4.2 | 36 |
| 21.3 | 4.2 | 2 |
| 21.8 | 4.1 | 4 |
| 22.4 | 4.0 | 6 |
| 22.9 | 3.9 | 17 |
| 23.6 | 3.8 | 2 |
| 23.9 | 3.7 | 5 |
| 24.2 | 3.7 | 1 |
| 24.6 | 3.6 | 3 |
| 24.8 | 3.6 | 1 |
| 25.1 | 3.6 | 15 |
| 25.5 | 3.5 | 1 |
| 26.0 | 3.4 | 1 |
| 26.5 | 3.4 | 3 |
| 26.7 | 3.3 | 1 |
| 27.2 | 3.3 | 4 |
| 27.6 | 3.2 | 2 |
| 27.9 | 3.2 | 6 |
| 28.7 | 3.1 | 3 |
| 29.2 | 3.1 | 1 |
| 29.4 | 3.0 | 2 |
| 30.0 | 3.0 | 9 |
| 30.2 | 3.0 | 3 |
| 30.7 | 2.9 | 3 |
| 31.1 | 2.9 | 2 |
| 32.1 | 2.8 | 2 |
| 33.3 | 2.7 | 2 |
| 34.1 | 2.6 | 2 |
| 35.5 | 2.5 | 2 |
| 36.4 | 2.5 | 2 |
| 37.1 | 2.4 | 1 |
| 38.3 | 2.4 | 2 |
| 38.7 | 2.3 | 1 |
| 39.0 | 2.3 | 1 |
| 39.5 | 2.3 | 1 |

Figure 36:
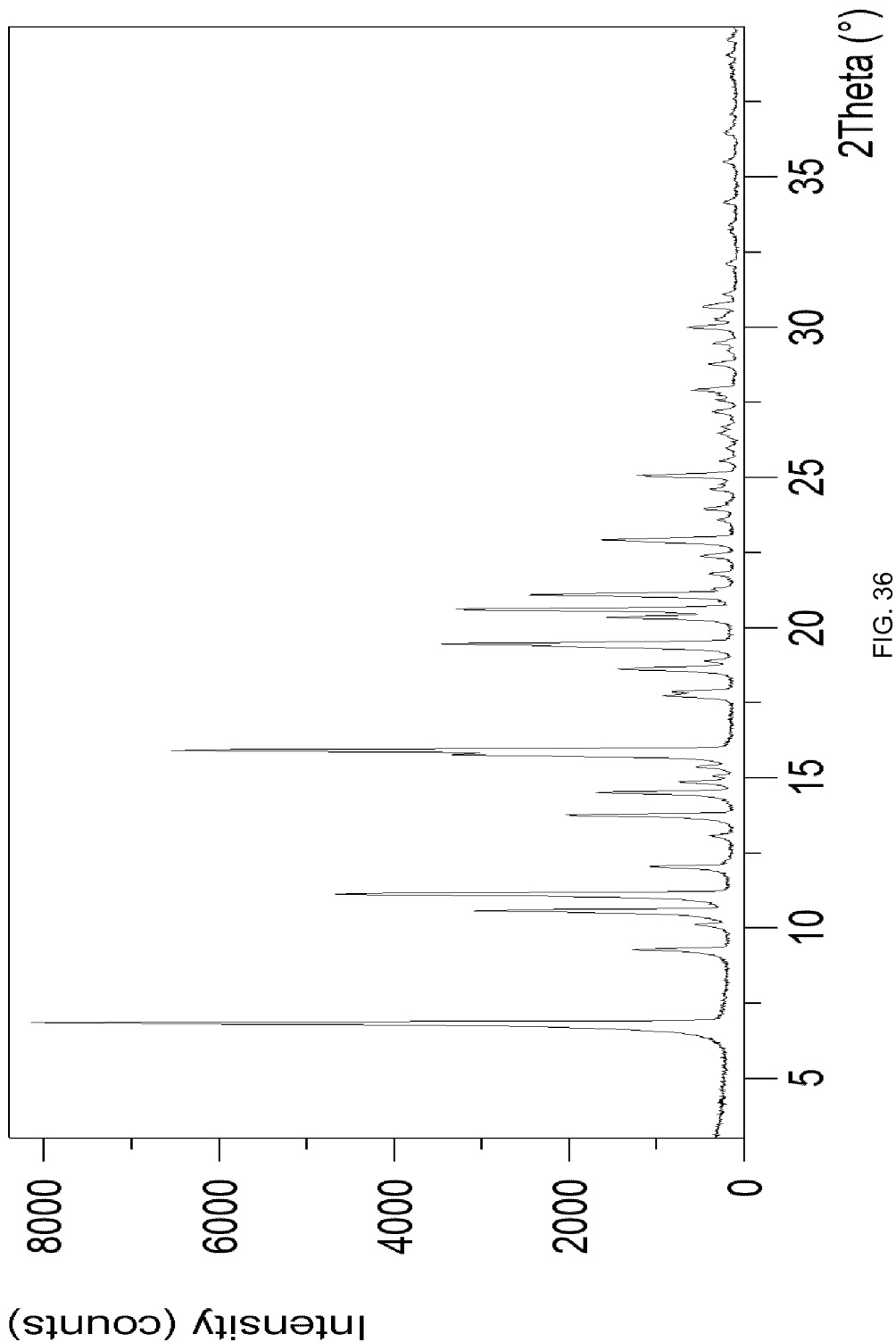
FIG. 36 shows the X-ray powder diffractogram (XRPD) of the cocrystal Form XIX. The spectrum expresses intensity (I; counts) versus degrees 2 theta (°).

The cocrystal Form XIX of the present invention may be further characterized by an X-ray diffractogram as in FIG. 36.

The cocrystal Form XIX of the present invention may also be further characterized by the following 1H NMR spectrum (DMSO·d6, 400 MHz, δ): 8.74 (s, 2H), 6.16-5.90 (m, 2H, ArH), 5.08 (s, 1H), 4.62-4.32 (m, 2H), 4.25-4.09 (m, 1H), 3.87-3.73 (d, J=8.7 Hz, 1H), 3.25-2.95 (m, 12H), 2.32-2.24 (m, 2H), 2.10 (s, 1H), 2.02-1.87 (m, 2H), 1.86-1.73 (m, 1H), 1.72-1.31 (m, 10H), 0.87 (t, J=7.3 Hz, 3H).

Figure 37:
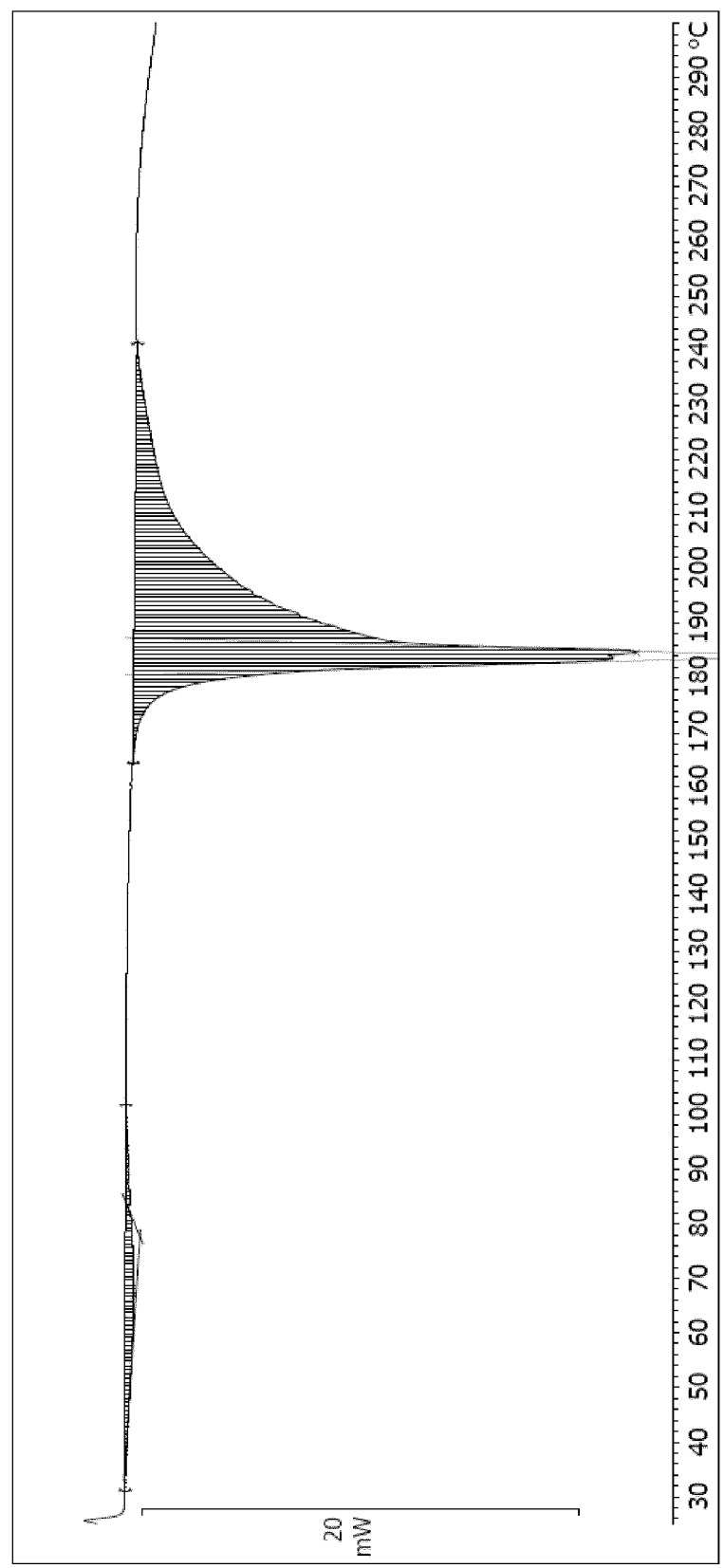
FIG. 37 shows the DSC of cocrystal Form XIX. The spectrum expresses the heat flow (mW/mg) versus temperature (° C.).

The cocrystal Form XIX of the present invention may also be further characterized by DSC (differential scanning calorimetry) analysis as shown in FIG. 37. The DSC analysis of cocrystal Form XIX shows a first endothermic event with an onset at ca. 34° C. followed by two overlapped endothermic events with an onset at ca. 180.2° C. that should correspond to the melting and degradation of the cocrystal Form XIX. The first event should correspond to the evaporation of residual solvents because cocrystal Form XIX remained stable after a heating up to 110° C. and DSC experiments indicated that this event is not reversible.

The cocrystal Form XIX of the present invention is in a molar ratio 1:1 (CBDV:L-carnitine).

In an embodiment, the cocrystal of Form XIX of the present invention has a purity equal to or higher than 99.0% a/a measured by HPLC (method 2).

In an embodiment, the solid composition of the present invention comprises a cocrystal of CBD and a coformer selected from the group consisting of L-proline, D-proline, DL-proline; particularly Forms I, II, III, IV, V; more particularly cocrystals Forms I, IV and V; more particularly cocrystal Form I.

In an embodiment, the solid composition of the present invention comprises a cocrystal of THC and a coformer selected from the group consisting of L-proline and D-proline; particularly cocrystals Forms VII and VIII; more particularly cocrystal Form VII.

In an embodiment, the cocrystal of the present invention is a cocrystal of THC and a coformer selected from the group consisting of L-proline and D-proline; particularly cocrystals Forms VII and VIII; more particularly cocrystal Form VII.

In an embodiment, the solid composition of the present invention comprises a cocrystal of delta8-THC and a coformer selected from the group consisting of L-proline and D-proline; particularly cocrystals Forms IX and X; more particularly cocrystal Form IX.

In an embodiment, the cocrystal of the present invention is a cocrystal of delta8-THC and a coformer selected from the group consisting of L-proline and D-proline; particularly cocrystals Forms IX and X; more particularly cocrystal Form IX.

In an embodiment, the solid composition of the present invention comprises a cocrystal of CBN and a coformer selected from the group consisting of L-proline, D-proline and betaine; particularly cocrystals Forms XI, XII, XIII, XIV and XV; more particularly cocrystal Forms XI, XII and XIII.

In an embodiment, the cocrystal of the present invention is a cocrystal of a cocrystal of CBN and a coformer selected from the group consisting of L-proline, D-proline and betaine; particularly cocrystals Forms XI, XII, XIII, XIV and XV; more particularly cocrystal Forms XI, XII and XIII.

In an embodiment, the solid composition of the present invention comprises a cocrystal of CBG and a coformer selected from the group consisting of betaine and L-carnitine; particularly cocrystals Forms XVI and XVII.

In an embodiment, the cocrystal of the present invention is a cocrystal of CBG and a coformer selected from the group consisting of betaine and L-carnitine; particularly cocrystals Forms XVI and XVII.

In an embodiment, the solid composition of the present invention comprises a cocrystal of CBDV and a coformer selected from the group consisting of betaine and L-carnitine; particularly cocrystals Forms XVIII and XIX.

In an embodiment, the cocrystal of the present invention is a cocrystal of a cocrystal of CBDV and a coformer selected from the group consisting of betaine and L-carnitine; particularly cocrystals Forms XVIII and XIX.

The third aspect of the invention is the provision of processes for the preparation of the cocrystal as defined above, which means cocrystals Form I, II, III, IV, V, VI, VII, VIII, IX, X, XI, XII, XIII, XIV, XV, XVI, XVII, XVIII and XIX. The cocrystals of the present invention may be prepared as a pure form or as a mixture. Any process disclosed in the state of the art for the preparation of cocrystals can be used for the cocrystals of the present invention, for instance wet grinding or slurring.

The terms "wet grinding" and "liquid assisted grinding" are equivalent and refer to a technique which consists of milling or grinding the product or mixture with some drops of solvent added. Neat and liquid-assisted grinding are techniques that can be employed in order to produce cocrystals. In neat (dry) grinding, cocrystal formers are ground together manually using a mortar and pestle, using a ball mill, or using a vibratory mill. In liquid-assisted grinding, or kneading, a small or substoichiometric amount of liquid (solvent) is added to the grinding mixture.

The term "slurring" as disclosed herein refers to any process which employs a solvent to wash or disperse by stirring a suspension of a compound.

Thus, a process for the preparation of the cocrystal of the present invention comprises: (a) wet grinding a mixture of the cannabinoid and the co-former in a solvent; and (b) drying the cocrystal thus obtained.

In an embodiment, step (a) is carried out in the presence of a solvent selected from the group consisting of water; an organic solvent selected from $(C_5-C_9)$alkane, $(C_1-C_4)$alcohol, $(C_1-C_4)$alkyl-CO—$(C_1-C_4)$alkyl, halogen-$(C_1-C_4)$alkane, $(C_1-C_4)$alkyl-CO—O—$(C_1-C_4)$alkyl, cyclo$(C_5-C_7)$ alkane, phenyl-$(C_1-C_4)$alkyl, $(C_1-C_4)$—CN, H—CO—N$((C_1-C_4)$alkyl$)_2$; and mixtures thereof. The term "alcohol" refers to an "alkane" wherein at least one hydrogen atom is substituted by a hydroxyl group and which contains the number of carbon atoms specified in the description or claims. The term "alkane" refers to a saturated, branched or linear hydrocarbon which contains the number of carbon atoms specified in the description or claims. Examples include methanol, ethanol, n-propanol, iso-propanol, butanol, iso-butanol, and sec-butanol. The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl. The term "halogen-alkane" refers to an alkane in which at least one hydrogen atom is substituted by an halogen atom and which contains the number of carbon atoms specified in the description or claims. Examples of halogen-alkane include chloroform, trichloroethane and dichloroethane. The term cycloalkane refers to a "cyclic" alkane which contains the number of carbon atoms specified in the description or claims. The term cycloalkane includes carbocyclic alkanes or heterocyclic alkanes. The term "carbocyclic" alkane refers to a cyclic alkane being each member of the cycle a carbon atom. Examples of carbocyclic alkanes include cyclopentane and cyclohexane. The term "heterocyclic" alkane refers to a "carbocyclic" compound in which at least one carbon atom is substituted by a N, NH, O, or S atom. Examples of heterocyclic alkane include tetrahydrofuran and 1,4-dioxane. In an embodiment, step (a) is carried out in the presence of an organic solvent selected from the group consisting of $(C_5-C_8)$alkane, $(C_1-C_4)$alcohol, $(C_1-C_4)$alkyl-CO—$(C_1-C_4)$alkyl, halogen-$(C_1-C_4)$alkane, $((C_1-C_4)$alkyl-CO—O—$(C_1-C_4)$alkyl, cyclo$(C_5-C_7)$ alkane, phenyl-$(C_1-C_4)$alkyl, $(C_1-C_4)$—CN, H—CO—N$((C_1-C_4)$alkyl$)_2$ and mixtures thereof. This process is particularly advantageous because allows for obtaining the cocrystal in pure form.

In an embodiment, step (a) is carried out in the presence of heptane, water, acetonitrile, methanol, IPA, isobutanol, ethylacetate, isobutylacetate, methylisobutylketone, dimethylformamide, 1,4-dioxane, dichloromethane, xylene, cyclohexane, heptane and mixtures thereof.

In an embodiment, when the cocrystal is cocrystal Form I, then step (a) is performed in a solvent selected from the group consisting of water, acetonitrile, methanol, isobutylacetate, methylisobutylketone, dimethylformamide, 1,4-dioxane, dichloromethane, xylene, and mixtures thereof.

In an embodiment, when the cocrystal is cocrystal Form II, then step (a) is performed in a solvent selected from the group consisting of $(C_1-C_4)$alkyl-CO—$(C_1-C_4)$alkyl, $(C_1-C_4)$alkyl-CO—O—$(C_1-C_4)$alkyl, cyclo$(C_5-C_7)$ alkane, phenyl-$(C_1-C_4)$alkyl, H—CO—N$((C_1-C_4)$alkyl$)_2$ and mixtures thereof.

In an embodiment, when the cocrystal is cocrystal Form III, then the solvent of step (a) is cyclo$(C_5-C_7)$ alkane and mixtures thereof. In an embodiment, step (a) is cyclohexane and mixtures thereof.

In an embodiment, when the cocrystal is cocrystal Form IV, then the solvent of step (a) is $(C_5-C_{12})$ alkane and mixtures thereof. In an embodiment, step (a) is heptane and mixtures thereof.

In an embodiment, when the cocrystal is cocrystal Form V, then the solvent of step (a) is $(C_5-C_{12})$ alkane and mixtures thereof. In an embodiment, step (a) is heptane and mixtures thereof.

In an embodiment, when the cocrystal is cocrystal Form VI, then the solvent of step (a) is $(C_5-C_{12})$ alkane and mixtures thereof. In an embodiment, step (a) is heptane and mixtures thereof.

In an embodiment, when the cocrystal is cocrystal Form XIX, then the solvent of step (a) is $(C_1-C_4)$alcohol, $(C_1-C_4)$alkyl-CO$_2(C_1-C_4)$alkyl or mixtures thereof. In an embodiment, step (a) is isopropanol, ethyl acetate and mixtures thereof.

In an embodiment, when the cocrystal is a cocrystal selected from Forms I, II, III, IV, V and VI then the molar ratio between the CBD and the coformer in step a) is from 2:1 to 1:2; preferably 1:1 for Forms I, II, IV, V and VI, and preferably 1:2 for Form VI.

In an embodiment, when the cocrystal is a cocrystal selected from XVIII and XIX then the molar ratio between the CBDV and the coformer in step a) is from 2:1 to 1:2; preferably 1:1.

The term "molar ratio" has been used to express the stoichiometric amount in mols of a compound in relation to another compound. For example, the stoichiometric amount in mols of one of the coformers of the cocrystal in relation to the other coformer. The molar ratio can be determined by $^1$H NMR.

In an embodiment, step (a) is carried out at room temperature. In another embodiment, step (a) is carried out under vibrational milling, particularly at a power comprised from 15 Hz to 60 Hz.; preferably comprised from 20 and 50 Hz; more preferably comprised from 25 and 35 Hz, particularly 30 Hz. The term "room temperature" refers to a temperature of the environment, without heating or cooling, and is generally comprised from 20° C. to 25° C.

In an embodiment, step (b) is carried out by drying the cocrystal thus obtained at room temperature, preferably under vacuum conditions. Generally, the vacuum involves a pressure comprised from 0.5 mbar to 3 mbar; preferably comprised from 1 to 2 mbar.

An alternative process for the preparation of the cocrystal of the present invention comprises: (c) slurring the cannabinoid with a coformer and an organic solvent; and (d) isolating the cocrystal thus obtained.

In an embodiment, step (c) is carried out in the presence of a solvent selected from the group consisting of $(C_1-C_4)$ alcohol, $(C_1-C_4)$alkyl-CO—$(C_1-C_4)$alkyl, halogen-$(C_1-C_4)$ alkane, $(C_1-C_4)$alkyl-CO—O—$(C_1-C_4)$alkyl, cyclo$(C_5-C_7)$ alkane, phenyl-$(C_1-C_4)$alkyl, $(C_1-C_4)$alkyl-O—$(C_1-C_4)$alkyl, $(C_5-C_8)$alkane, and mixture thereof. In an embodiment, step (c) is carried out in the presence of a solvent selected from the group consisting of cyclohexane, ethanol, isopropylalcohol, ethylacetate, acetone, methyl isobutyl ketone, tetrahydrofuran, methyl tert-butyl ether, dichloromethane, heptane, and toluene.

In an embodiment, when the cocrystal is cocrystal Form I, then step (c) is performed in a solvent selected from the group consisting of $(C_1-C_4)$alcohol, cyclo$(C_5-C_7)$ alkane, $(C_5-C_9)$alkane, aromatic alkane and mixtures thereof. In an embodiment, step c) is performed in a solvent selected form the group consisting of cyclo$(C_5-C_7)$ alkane, $(C_5-C_9)$alkane, $(C_1-C_4)$alcohol and a mixture thereof. In an embodiment, step (c) is carried out in the presence of a solvent selected from the group consisting of EtOH and heptane and mixtures thereof; preferably heptane.

In an embodiment, when the cocrystal is cocrystal Form II, then step (c) is performed in a solvent selected from the group consisting of cyclo$(C_5-C_7)$ alkane, $(C_5-C_9)$alkane, and mixtures thereof; particularly cyclo$(C_5-C_7)$ alkane, $(C_5-C_9)$ alkane and a mixture thereof; preferably cyclohexane and heptane.

In an embodiment, when the cocrystal is cocrystal Form III, then step (c) is performed in a solvent selected from the group consisting of cyclo$(C_5-C_7)$ alkane, $(C_5-C_9)$alkane and mixtures thereof; particularly cyclo$(C_5-C_7)$ alkane, $(C_5-C_9)$ alkane and a mixture thereof; preferably cyclohexane and heptane.

In an embodiment, when the cocrystal is cocrystal Form IV, then step (c) is performed in a solvent selected from the group consisting of $(C_1-C_4)$alcohol, cyclo$(C_5-C_7)$ alkane, $(C_5-C_9)$alkane and mixtures thereof. In an embodiment, step c) is performed in a solvent selected form the group consisting of cyclo$(C_5-C_7)$ alkane, $(C_5-C_9)$alkane, $(C_1-C_4)$alcohol and a mixture thereof. In an embodiment, step (c) is carried out in the presence of a solvent selected from the group consisting of EtOH and heptane and mixtures thereof; preferably heptane.

In an embodiment, when the cocrystal is cocrystal Form V, then step (c) is performed in a solvent selected from the group consisting of $(C_1-C_4)$alcohol, cyclo$(C_5-C_7)$ alkane, $(C_5-C_9)$alkane and mixtures thereof. In an embodiment, step c) is performed in a solvent selected form the group consisting of cyclo$(C_5-C_7)$ alkane, $(C_5-C_9)$alkane, $(C_1-C_4)$alcohol and a mixture thereof. In an embodiment, step (c) is carried out in the presence of a solvent selected from the group consisting of EtOH and heptane and mixtures thereof; preferably heptane.

In an embodiment, when the cocrystal is cocrystal Form VI, then step (c) is performed in a solvent selected from the group consisting of cyclo$(C_5-C_7)$ alkane, $(C_5-C_9)$alkane and mixtures thereof; In an embodiment, step c) is performed in a solvent which is a $(C_5-C_9)$alkane, preferably heptane.

In an embodiment, when the cocrystals are cocrystal Forms VII and VIII, then step c) is performed in an $(C_1-C_4)$alkylCO$(C_1-C_4)$alkyl, I, $(C_5-C_9)$alkane, $(C_1-C_4)$alkyl-COO$(C_1-C_4)$alkyl, acetonitrile and mixtures thereof. In an embodiment, step c) is performed in a solvent which is a $(C_5-C_9)$alkane, particularly heptane and mixtures thereof.

In an embodiment, when the cocrystals are cocrystal Forms IX and X, then step c) is performed in an ($C_1$-$C_4$) alkylCO($C_1$-$C_4$)alkyl, ($C_1$-$C_4$)alcohol, ($C_5$-$C_9$)alkane, ($C_1$-$C_4$)alkylCOO($C_1$-$C_4$)alkyl, acetonitrile and mixtures thereof. In an embodiment, step c) is performed in a solvent which is a ($C_5$-$C_9$)alkane, particularly heptane and mixtures thereof.

In an embodiment, when the cocrystals are cocrystals Forms XI-XV, then step c) is performed in a solvent selected from the group consisting of cyclo($C_5$-$C_7$) alkane, ($C_5$-$C_9$) alkane and mixtures thereof. In an embodiment, step c) is performed in a solvent which is a ($C_5$-$C_9$)alkane, preferably heptane.

In an embodiment, when the cocrystals are cocrystals Forms XVI-XVII, then step c) is performed in a solvent selected from the group consisting of phenyl-($C_1$-$C_4$)alkyl, cyclo($C_5$-$C_7$) alkane, ($C_5$-$C_9$)alkane, ($C_1$-$C_4$)alcohol and mixtures thereof; preferably ethanol, toluene and heptane. In an embodiment, step c) is performed in a solvent which is a ($C_5$-$C_9$)alkane, more preferably heptane.

In an embodiment, when the cocrystals are cocrystals Forms XVIII-XIX, then step c) is performed in a solvent selected from the group consisting of alcohol ($C_3$-$C_5$), ($C_1$-$C_4$)alkyl-$CO_2$($C_1$-$C_4$)alkyl and mixtures thereof; preferably isopropanol, isobutanol and ethyl acetate.

In an embodiment, the organic solvent of step (c) the process for the preparation of the cocrystal of the present invention is selected from the group consisting of cyclo($C_5$-$C_7$) alkane, ($C_5$-$C_9$)alkane and mixtures thereof; with the proviso that when the cannabinoid is 2-((1R,6R)-3-methyl-6-(prop-1-en-2-yl) cyclohex-2-enyl)-5-propylbenzene-1,3-diol, then the organic solvent of step (c) is selected from the group consisting of alcohol ($C_3$-$C_5$), ($C_1$-$C_4$)alkyl-$CO_2$($C_1$-$C_4$)alkyl and mixture thereof. In an embodiment, the organic solvent of step (c) the process for the preparation of the cocrystal of the present invention is heptane; with the proviso that when the cannabinoid is 2-((1R,6R)-3-methyl-6-(prop-1-en-2-yl) cyclohex-2-enyl)-5-propylbenzene-1,3-diol, then the organic solvent of step (c) is isopropanol, isobutanol and ethyl acetate.

In an embodiment, when the cannabinoid is CBD, THC, CBN, CBG and delta8-THC, then the step c) is performed in cyclo($C_5$-$C_7$) alkane, ($C_5$-$C_9$)alkane and mixtures thereof; particularly heptane. In an embodiment, when the cocrystals are cocrystals Forms I-XVII then step c) is performed in cyclo($C_5$-$C_7$) alkane, ($C_5$-$C_9$)alkane and mixtures thereof; particularly heptane. In an embodiment, when the cannabinoid is CBDV, then the step c) is performed in alcohol ($C_3$-$C_5$), ($C_1$-$C_4$)alkyl-$CO_2$($C_1$-$C_4$)alkyl and mixtures thereof; particularly, isopropanol, isobutanol and ethyl acetate. In an embodiment, when the cocrystals are cocrystals Forms XVIII-XIX, then step c) is performed in ($C_3$-$C_5$) alcohol, ($C_1$-$C_4$)alkyl-$CO_2$($C_1$-$C_4$)alkyl and mixtures thereof; particularly in isopropanol, isobutanol and ethyl acetate. In an embodiment, when the cocrystal is the cocrystal Form XVIII, then step c) is performed in isobutanol. In an embodiment, when the cocrystal is cocrystal Form XIX, then step c) is performed in isopropanol and ethyl acetate.

In an embodiment, the molar ratio between the CBD and the coformer in step (c) is from 2:1 to 1:3; particularly 2:1 to 1:2; preferably from 2:1 to 1:1. In a particular embodiment, when the cocrystal is cocrystal Form I, then the molar ratio between the CBD and the coformer is 1:1; particularly 1:0.6. In a particular embodiment, when the cocrystal is cocrystal Form II, then the molar ratio between the CBD and the coformer is from 2:1 to 1:1; preferably 2:1. In a particular embodiment, when the cocrystal is cocrystal Form III, then the molar ratio between the CBD and the coformer is from 3:1 to 1:2; preferably 3:1. In a particular embodiment, when the cocrystal is cocrystal Form IV or Form V, then the molar ratio between the CBD and the coformer is from 2:1 to 1:3; preferably from 2:1 to 1:1. In a particular embodiment, when the cocrystal is cocrystal Form IV, then the molar ratio between the CBD and the coformer is 1:0.5. In a particular embodiment, when the cocrystal is cocrystal Form VI, then the molar ratio between the CBD and the coformer is from 3:1 to 1:2; preferably 3:1.

In an embodiment, the molar ratio between the THC and the coformer in step (c) is from 1:1 to 1:0.6; preferably from 1:1 to 1:0.6. In a particular embodiment, when the cocrystal is cocrystal Form VII, then the molar ratio between the THC and the coformer is 1:0.6. In a particular embodiment, when the cocrystal is cocrystal Form VIII, then the molar ratio between the THC and the coformer is 1:0.6.

In an embodiment, the molar ratio between the delta8-THC and the coformer in step (c) is from 1:1 to 1:0.4; particularly from 1:1 to 1:0.6. In a particular embodiment, when the cocrystal is cocrystal Form IX, then the molar ratio between the delta 8-THC and the coformer is 1:0.6. In a particular embodiment, when the cocrystal is cocrystal Form X, then the molar ratio between the delta8-THC and the coformer is 1:0.6.

In an embodiment, when the cocrystal is a cocrystal selected from Form XI, XII, XIII, XIV and XV, then the molar ratio between the CBN and the coformer in step (c) is from 4:1 to 1:2; particularly 2:1.

In an embodiment, when the cocrystal is a cocrystal selected from Form XVI, XVII and XVIII, then the molar ratio between the CBG and the coformer in step (c) is from 2:1 to 1:2; particularly 1:1.

In an embodiment, step (c) is carried out at room temperature. In another embodiment, step (c) is maintained under stirring overnight. The term "overnight" refers to a time interval comprised from 10 h to 48 h, more preferably 20 h In an embodiment, step (c) is carried out under an inert atmosphere. The term "inert atmosphere" refers to an atmosphere having an oxygen content of no greater than 500 ppm. In an embodiment, inert atmosphere comprises one or more inert gas selected form the group consisting of nitrogen, helium and argon; preferably nitrogen. This process is particularly advantageous because allows for obtaining the cocrystal in pure form avoiding the risk of degradation of the cannabinoid by oxidation or heating; particularly THC.

In an embodiment, the isolation step (d) may include removing the solvent, for example, by one or more of the following operations: filtration, filtration under vacuum, decantation, and centrifuge, or other suitable techniques as known to a person skilled in the art. In an embodiment, step (d) is carried out by filtration of the solid followed by a washing step. In an embodiment, when the cocrystal is cocrystal Form I, II, III, IV, V and VI, then the washing step is performed with an ($C_5$-$C_8$)alkane; particularly heptane. In an embodiment, step (d) is carried out by filtration of the solid followed by a washing step. In an embodiment, when the cocrystal is cocrystal Form VII and VIII, then the washing step is performed with an ($C_5$-$C_8$)alkane; particularly heptane. In an embodiment, when the cocrystal is cocrystal Form IX and X, then the washing step is performed with an ($C_5$-$C_8$)alkane; particularly heptane. In an embodiment, step (d) further comprises drying the isolated cocrystal; preferably the cocrystal is dried at room temperature, preferably under vacuum conditions. Generally, the vacuum involves a pressure comprised from 0.5 mbar to 3 mbar. In an embodiment, when the cocrystal is cocrystal Form XI-XIX, then the washing step is performed with alcohol ($C_3$-$C_5$) or ($C_1$-$C_4$)alkyl-$CO_2$($C_1$-$C_4$)alkyl, preferably isopropanol, isobutanol and ethyl acetate In a particular embodiment, the mixture of step (a), or alternatively step (c) is seeded to start the crystallization. In an embodiment, step (a), or alternatively step (c) is seeded with the cocrystal of the invention, particularly cocrystal Form I, cocrystal Form II, cocrystal Form III, cocrystal Form IV, cocrystal Form V, cocrystal Form VI, cocrystal Form VII and cocrystal Form VIII. When the cocrystal is cocrystal Form I, II and III, the seeding cocrystal form may be obtained by wet grinding process as shown in the examples. When the cocrystal is cocrystal Form IV, V, VI, VII and VIII, the seeding cocrystal form may be obtained by slurring method, for instance following the process as disclosed in the examples. When the cocrystal is cocrystal Form IX and X, the seeding cocrystal form may be obtained by slurring method, for instance following the process as disclosed in the examples. When the cocrystal is cocrystal Form XI, XII, XIII, XIV, XV, XVI, XVII and XVIII, the seeding cocrystal form may be obtained by slurring method, for instance following the process as disclosed in the examples. When the cocrystal is cocrystal Form XIX, the seeding cocrystal form may be obtained by grinding method, for instance following the process as disclosed in the example.

It is also part of the invention, a process for the purification of a cannabinoid which comprises: (e) dissociating a cocrystal as defined above under such reaction conditions to obtain the cannabinoid; and (f) isolating the cannabinoid thus obtained.

In an embodiment, the purification process further comprises previous steps of preparing the cocrystal by the process as defined above in the second aspect of the invention comprising performing steps (c) and (d); or alternatively performing steps (a) and (b). All embodiments disclosed above for steps (a), (b), (c) and (d) also apply in the process for the purification of cannabinoid of the present invention, particularly for the purification of CBD, THC, delta8-THC, CBN, CBG and CBDV; more particularly for the purification of THC, CBD, CBN, and CBDV.

In an embodiment, step (e) is carried out by dissociating the cocrystal of the cannabinoid as defined above in an organic solvent; or alternatively in a mixture of water and one or more water-immiscible organic solvent and subsequent separation of the phases of the biphasic mixture. Examples of organic solvents suitable for performing step (e) include, among others, ($C_1$-$C_4$)alkyl-CO—O—($C_1$-$C_4$)alkyl, ($C_1$-$C_4$)alkyl-O—($C_1$-$C_4$)alkyl, ($C_1$-$C_4$)alkyl-CO—($C_1$-$C_4$)alkyl and ($C_1$-$C_9$)alkane. The term "immiscible organic solvent" refers to an organic solvent that, when combined, forms two phases, which means that the mixture thus obtained is "biphasic" under specified conditions of component concentrations and temperature among others. Further, the term "water-immiscible organic solvent" refers to an organic solvent that can form a biphasic phase with water at the temperature at which the reaction is carried out. As used herein, the term "biphasic" refers to a reaction medium that includes two immiscible liquid phases, for example, an aqueous phase and a water-immiscible organic solvent phase. The term "biphasic" can also be used to describe a method employing such a reaction medium. In an embodiment, in step (e) the water-immiscible organic solvent is selected from the group consisting of ($C_5$-$C_9$)alkane, ($C_1$-$C_4$)alkyl-O—($C_1$-$C_4$)alkyl and mixtures thereof; preferably ($C_1$-$C_9$)alkane. Examples of ($C_1$-$C_9$)alkane include, among others, heptane, cyclohexane, pentane and mixtures thereof.

In an embodiment, in step (e) when the cocrystal is a cocrystal Form VII or VIII, then the volume ratio between water and the water-immiscible organic solvent is from 1:2 to 1:3; preferably from 1:2 to 1:2.3. In a particular embodiment, when the cocrystal is cocrystal Form VII, then the volume ratio water and the water-immiscible organic solvent is from 1:2 to 1:3; preferably from 1:2 to 1:2.3. The term "volume ratio" has been used to express the stoichiometric amount in volume of a compound in relation to another compound.

In an embodiment, in step (e) when the cocrystal is a cocrystal Form XI-XIX, then the volume ratio between water and the water-immiscible organic solvent is from 2:1 to 1:3; preferably from 1:1 to 2:1. In a particular embodiment, when the cocrystal is cocrystal Form XI, then the volume ratio water and the water-immiscible organic solvent is 1:2. In a particular embodiment, when the cocrystal is cocrystal Form XIX, then the volume ratio water and the water-immiscible organic solvent is 1:1. The term "volume ratio" has been used to express the stoichiometric amount in volume of a compound in relation to another compound.

Isolation step (f) may include removing the solvent by evaporation to dryness or isolating the cannabinoid, CBD, THC, delta 8-THC, CBN, CBG and CBDV; more particularly THC or CDB, CBDV or CBN after crystallization, for example, by one or more of the following operations: filtration, filtration under vacuum, decantation, and centrifuge, or other suitable techniques as known to a person skilled in the art. In an embodiment, step (f) further comprises drying the isolated cannabinoid; preferably the cocrystal is dried at room temperature, preferably under vacuum conditions. Generally, the vacuum involves a pressure comprised from 0.5 mbar to 3 mbar.

In an embodiment, the process for the purification of a cannabinoid, CBD, THC, delta8-THC, CBN, CBG and CBDV; more particularly CBD, THC, CBN or CBDV, which comprises performing steps (e) and (f), further comprises performing steps (c) and (d) before step (e) as defined above in the present invention. Thus, the process for the purification of a cannabinoid, CBD THC, delta8-THC, CBN, CBG and CBDV; more particularly CBD, THC, CBN or CBDV, comprises performing steps (c), (d), (e) and (f) as defined above.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Proton nuclear magnetic resonance analysis were recorded in deuterated solvents in a Varian Mercury 400

MHz spectrometer, equipped with a broadband probe ATB 1H/19F/X of 5 mm. Spectra were acquired dissolving the sample in 0.7 mL of deuterated solvent.

X-ray power Diffraction (XRPD) measurements were performed at ambient conditions on a PANalytical X'Pert PRO θ-θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during the data collection. The measurement angular range was 3.0-40.0° (2θ) with a step size of 0.013° and a scanning speed 0.328°/s (10.20 s/step) for the cocrystals of cannabinoids and the THC used as starting material; and 3.0-30.0° (2θ) with a step size of 0.013° and a scanning speed 0.082°/s (40.80 s/step) for commercial CBD used as starting material and purified CBD obtained after dissociating the cocrystal of the present invention.

DSC analyses were recorded with a Mettler Toledo DSC2. For cocrystals Forms I-VIII, and XI-XIX, the sample was weighed into a 40 μL aluminium crucible with a pinhole lid and was heated from 25 to 300° C. at a rate of 10° C./min, under nitrogen (50 mL/min). For cocrystals Form VII and VIII, the sample was weighed into a 40 μL aluminium crucible with a pinhole lid and was heated from 25 to 150° C. at a rate of 10° C./min, under nitrogen (50 mL/min).

HPLC analyses were recorded Agilent 1100 HPLC system equipped with a vacuum degasser (G1322A), a quaternary pump (G1311A), an autosampler (G1313A) and a UV detector (G1314A) using different conditions depending on the experiments:

Method 1: Column Zorbax Eclipse XDB-C18 150×4.6 mm, 5 μm was used. The sample (5 mg) was dissolved in methanol (5 mL) and injected (1 μL) for HPLC measurement in isocratic conditions (ACN:water 80:20) with the detector measuring at 225 nm.

Method 2: Column Kinetex EVO C18; 2.6 μm; 50×4.6 mm was used. The sample (5 mg) was dissolved in methanol (5 mL) and injected (1 μL). HPLC measurement was performed at 40° C. with the detector measuring at 210 nm and a mobile phase A:ACN and B:water (Flow 1.2 mL/min) with the following gradient:

| t(min) | A (%) | B (%) |
|---|---|---|
| 0 | 45 | 55 |
| 12 | 45 | 55 |
| 17 | 0 | 100 |
| 25 | 0 | 100 |

Thermogravimetric analysis (TGA) was recorded in a thermogravimetric analyzer Mettler Toledo TGA/SDTA851. The sample was weighed into a 100 μL alumina crucible and sealed with a lid. The lid was automatically punched by the robot just before the analysis. Samples were heated at 10° C./min from 25 to 300° C., under nitrogen (50 mL/min).

Karl Fischer (KF) analyses were recorded with a Metrohm 870 KF Titrino Plus. The samples were analyzed in duplicate using the following reactants: Aquametric Composite 5 (Panreac Ref. 285812.1610), Methanol dry (Panreac Ref. 481091.1611) and Karl Fischer Water Standard 1.0 mg/g (Panreac Ref. 395459.2527; used to calculate the factor).

GC (gas chromatography) analyses were recorded in an Agilent 6890N system equipped with autosampler injector (G2613A) and a Flame Ionization Detector (G1530N). Column HP-5, 30m, 0.2 mm ID, 0.33 μm was used. The sample (5 mg of THC equivalent) was dissolved in methanol (5 mL) and injected (2 μL) for GC measurement (injector temperature 220° C., detector temperature 300° C., split ratio 50:1, flow 3 mL/min, carrier He, initial temperature 200° C. for 1 min, first ramp (rate 10°/min, final temperature 220° C. for 5 min), second ramp (25° C./min, final temperature 300° C. for 5 min)).

CBD used as a starting material obtained by an extractive process was commercially available (CBDepot s.r.o.). Cannabis sativa fraction containing about 50% w/w of CBD used as starting material was also commercially available (CBDepot s.r.o.). L-proline (TCI), L-proline hydrate (obtained by exposition of L-Proline to humidity), betaine (Sigma), L-carnitine (TCI), D-proline (TCI), DL-proline (TCI) and (2S,3aS,7aS)-octahydro-1H-indole-2-carboxylic acid (TCI) used as starting material were also commercially available.

Tablet hardness was recorded in a Heberlein-Schleuniger 5Yi durometer, 5 tablets comprising cocrystal Form I of the present invention were tested following the process disclosed in section 2.9.8. of the 9$^{th}$ edition European Farmacopoeia (Ph. Eur, 2019).

Tablet disintegration test was performed in a disintegration apparatus type A according to the European Pharmacopoeia following the process disclosed in section 2.9.1. of the 9$^{th}$ edition European Farmacopoeia (Ph. Eur, 2019). 6 tablets comprising cocrystal Form I of the present invention were tested using deionized water at 37° C. as a disintegration medium.

1. Solid Oral Compositions 1.1. Capsules 1.1.1. Hard Capsules of CBD 1.1.1.1. Composition The qualitative and quantitative composition of a hard gelatine capsule containing the cocrystal Form I of the present invention obtained in Example 2.1 is as follow:

| Ingredients | (%) | Amount (mg) |
|---|---|---|
| Cocrystal Form I of the present invention | 10 | 20 |
| Vivapu ® 101[1] | 88 | 176 |
| Magnesium stearate | 2 | 4 |
| Total weight per capsule | | 200 |

Green/green hard gelatin capsule. Size 1.

[1]Vivapur ® 101 is Microcrystalline Cellulose commercially available from JRS Pharma 1.1.1.2. Process for the Preparation A) Preparation of the Powdered Mixture The amounts of cocrystal Form I of the present invention, microcrystalline cellulose and magnesium stearate defined in previous Table were manually mixed.

B) Filling of Capsules

Green/green hard gelatine capsules of size 1 were manually filled with 200 mg of the powdered mixture obtained in section a) each capsule.

1.1.2. Hard Capsules of THC
1.1.2.1. Composition

The qualitative and quantitative composition of a hard gelatine capsule containing the cocrystal Form VII of the present invention obtained in Example 2.7 is as follow:

| Ingredients | (%) | Amount (mg) |
|---|---|---|
| Cocrystal Form VII of the present invention | 9.5 | 19 |
| Vivapu ® 101[1] | 88.5 | 177 |
| Magnesium stearate | 2 | 4 |
| Total weight per capsule | | 200 |

Green/green hard gelatin capsule. Size 1.
[1]Vivapur ® 101 is Microcrystalline Cellulose commercially available from JRS Pharma

1.1.2.2. Process for the Preparation
A) Preparation of the Powdered Mixture The amounts of cocrystal Form VII of the present invention, microcrystalline cellulose and magnesium stearate defined in previous Table were manually mixed.

B) Filling of Capsules

Green/green hard gelatine capsules of size 1 were manually filled with 200 mg of the powdered mixture obtained in section a) each capsule.

1.2. Tablets
1.2.1. Tablets of CBD
1.2.1.1. Composition

The qualitative and quantitative composition of a tablet containing the cocrystal Form I of the present invention obtained in Example 2.1 is as follow:

| Ingredients | (%) | Amount (mg) |
|---|---|---|
| Cocrystal Form I of the present invention | 36.4 | 200 |
| Vivapu ® 101[1] | 54.5 | 300 |
| Vivasol ® [2] | 3.6 | 20 |
| Talc | 3.6 | 20 |
| Magnesium stearate | 1.8 | 10 |
| Total weight per tablet | | 550 |

[1]Vivapur ® 101 is Microcrystalline Cellulose commercially available from JRS Pharma.
[2] Vivasol ® is croscarmellose sodium commercially available from JRS Pharma.

1.2.1.2. Process for Preparation
A) Preparation of the Powdered Mixture

The amounts of cocrystal Form I of the present invention, microcrystalline cellulose and magnesium stearate defined in previous Table were manually mixed.

To the resultant blend the croscarmellose and the talc was added; and the resultant mixture was blended for 10 min under 20 rpm in a biconic mixer (e.g. biconic mixer Glatt SG17).

B) Compaction

The resultant blend obtained in step (a) was compacted into preforms (i.e. slugs) on an eccentric press (e.g. eccentric press machine Bonals CO5) using a 19×10 mm capsular shape punch.

C) Compression of Tablets

The resultant preforms obtained in step b) were sieved through a sieve of 0.8 mm to obtain granules, which are compressed into tablets on an eccentric press (e.g. eccentric press machine Bonals CO5) using a 17×8.5 mm oblong biconvex punch. Tablets thus obtained have the following parameters:

| | |
|---|---|
| Tablet weight | 550 mg |
| Limits of Tablet Weight variation | From 522.5 mg to 577.5 mg |
| Hardness | From 70N to 100N |
| Table Disgregation Time in water at 37° C. | Less than 15 min |
| Number of tablets | 44 |

The X-ray powder diffractogram (XRPD) of the tablet of CBD thus obtained shows that the cocrystal of CBD Form I disclosed in FIG. 1 maintained its integrity after its formulation.

1.2.2. Tablets of THC
1.2.2.1. Composition

The qualitative and quantitative composition of a tablet containing the cocrystal Form VII of the present invention obtained in Example 2.7 is as follow:

| Ingredients | (%) | Amount (mg) |
|---|---|---|
| Cocrystal Form VII of the present invention | 10 | 20 |
| Vivapu ® 101[1] | 88 | 176 |
| Magnesium stearate | 2 | 4 |
| Total weight per tablet | | 200 |

[1]Vivapur ® 101 is Microcrystalline Cellulose commercially available from JRS Pharma

1.2.2.2. Process for the Preparation
A) Preparation of the Powdered Mixture The amounts of cocrystal Form VII of the present invention, microcrystalline cellulose and magnesium stearate defined in previous Table were manually mixed.

B) Compression of Tablets

The resultant blend obtained in step (a) was compressed into tablets on an eccentric press (e.g. eccentric press machine Bonals CO5) with a 9 mm biconvex tablet punch. The tablets thus obtained have hardness from 72N to 98N.

The X-ray powder diffractogram (XRPD) of the tablet of THC thus obtained shows that the cocrystal of THC Form VII disclosed in FIG. 14 maintained its integrity after its formulation.

1.2.3. Tablets of CBN
1.2.3.1. Compositions

The qualitative and quantitative compositions of tablets containing the cocrystal Form XI of the present invention obtained in Example 2.11 are as follow:

| | Tablet 1 | | Tablet 2 | | Tablet 3 | | Tablet 4 | |
|---|---|---|---|---|---|---|---|---|
| Ingredients | (%) | Amount (mg) | (%) | Amount (mg) | (%) | Amount (mg) | (%) | Amount (mg) |
| Cocrystal Form XI of the present invention | 10 | 20 | 10 | 20 | 36.4 | 200 | 36.4 | 200 |
| Vivapu ® 101[1] | 88 | 176 | — | — | 54.54 | 300 | — | — |
| Magnesium stearate | 2 | 4 | 2 | 4 | 1.8 | 10 | 1.8 | 10 |

|  | Tablet 1 | | Tablet 2 | | Tablet 3 | | Tablet 4 | |
|---|---|---|---|---|---|---|---|---|
| Ingredients | (%) | Amount (mg) | (%) | Amount (mg) | (%) | Amount (mg) | (%) | Amount (mg) |
| Monohydrate lactose | — | — | 88 | 176 | — | — | 54.54 | 300 |
| Vivasol ® [2] | — | — | — | — | 3.63 | 20 | 3.63 | 20 |
| Talc | — | — | — | — | 3.63 | 20 | 3.63 | 20 |
| Total weight per tablet (mg) | | 200 | | 200 | | 550 | | 550 |

[1] Vivapur ® 101 is Microcrystalline Cellulose commercially available from JRS Pharma
[2] Vivasol ® is croscarmellose sodium commercially available from JRS Pharma.

1.2.3.2. Process for the Preparation

Tablets 1 and 2 by Direct compression

A) Preparation of the Powdered Mixture

The amounts of cocrystal Form XI of the present invention, microcrystalline cellulose and magnesium stearate defined in previous Table were manually mixed.

B) Compression of Tablets

The resultant blend obtained in step (a) was compressed into tablets on an eccentric press (e.g. eccentric press machine Bonals) with a 9 mm cylindric biconvex tablet punch.

Tablet 3 by Dry Granulation Method

A) Preparation of the Powdered Mixture

The amounts of cocrystal Form XI of the present invention, microcrystalline cellulose and croscarmellose defined in previous Table were manually mixed.

B) Compaction

The resultant blend obtained in step (a) was compacted into preforms (i.e. slugs) on an eccentric press (e.g. eccentric press machine Bonals) using a 19×10 mm capsular biconvex shape punch.

C) Compression of Tablets

The resultant preforms obtained in step b) were sieved through a sieve of 0.8 mm to obtain granules. To the resultant granules, talc and magnesium stearate were added and manually mixed. Then, the resultant mixture was compressed into tablets on an eccentric press (e.g. eccentric press machine Bonals) using a 17×8.5 mm oblong biconvex punch.

Tablet 4 by Dry Granulation Method

A) Preparation of the Powdered Mixture

The amounts of cocrystal Form XI of the present invention, monohydrate lactose and croscarmellose defined in previous Table were manually mixed.

B) Compaction

The resultant blend obtained in step (a) was compacted into preforms (i.e. slugs) on an eccentric press (e.g. eccentric press machine Bonals) using a 19×10 mm capsular biconvex shape punch.

C) Compression of Tablets

The resultant preforms obtained in step b) were sieved through a sieve of 0.8 mm to obtain granules. To the resultant granules, talc and magnesium stearate were added and manually mixed. Then, the resultant mixture was compressed into tablets on an eccentric press (e.g. eccentric press machine Bonals) using a 17×8.5 mm oblong biconvex punch.

1.2.4. Tablets of CBG 1.2.4.1. Compositions

The qualitative and quantitative compositions of tablets containing the cocrystal Form XVI of the present invention obtained in Example 2.16 are as follow:

|  | Tablet 1 | | Tablet 2 | |
|---|---|---|---|---|
| Ingredients | (%) | Amount (mg) | (%) | Amount (mg) |
| Cocrystal Form XVI of the present invention | 10 | 20 | 33 | 178 |
| Vivapu ® 101[1] | 88 | 176 | 59 | 322 |
| Magnesium stearate | 2 | 4 | 2 | 10 |
| Vivasol ® [2] | — | — | 3 | 20 |
| Talc | — | — | 3 | 20 |
| Total weight per tablet (mg) | | 200 | | 550 |

(3) Vivapur ® 101 is Microcrystalline Cellulose commercially available from JRS Pharma
(4) Vivasol ® is croscarmellose sodium commercially available from JRS Pharma.

1.2.4.2. Process for the Preparation

Tablets 1 by Direct Compression

A) Preparation of the Powdered Mixture

The amounts of cocrystal Form XVI of the present invention, microcrystalline cellulose and magnesium stearate defined in previous Table were manually mixed.

B) Compression of Tablets

The resultant blend obtained in step (a) was compressed into tablets on an eccentric press (e.g. eccentric press machine Bonals) with a 9 mm cylindric biconvex tablet punch.

Tablets 2 by Dry Granulation Method

A) Preparation of the Powdered Mixture

The amounts of cocrystal Form XVI of the present invention, microcrystalline cellulose and croscarmellose defined in previous Table were manually mixed.

B) Compaction

The resultant blend obtained in step (a) was compacted into preforms (i.e. slugs) on an eccentric press (e.g. eccentric press machine Bonals) using a 19×10 mm capsular biconvex shape punch.

C) Compression of Tablets

The resultant preforms obtained in step b) were sieved through a sieve of 0.8 mm to obtain granules. To the resultant granules, talc and magnesium stearate were added and manually mixed. Then, the resultant mixture was compressed into tablets on an eccentric press (e.g. eccentric press machine Bonals) using a 17×8.5 mm oblong biconvex punch.

1.2.5. Tablets of CBDV 1.2.5.1. Compositions

The qualitative and quantitative compositions of tablets containing the cocrystal Form XIX of the present invention obtained in Example 2.19 are as follow:

|  | Tablet 1 | | Tablet 2 | | Tablet 3 | | Tablet 4 | |
|---|---|---|---|---|---|---|---|---|
| Ingredients | (%) | Amount (mg) | (%) | Amount (mg) | (%) | Amount (mg) | (%) | Amount (mg) |
| Cocrystal Form XIX of the present invention | 10 | 20 | 10 | 20 | 36.4 | 200 | 36.4 | 200 |
| Vivapur ® 101[(1)] | 88 | 176 | — | — | 54.54 | 300 | — | — |
| Magnesium stearate | 2 | 4 | 2 | 4 | 1.8 | 10 | 1.8 | 10 |
| Monohydrate lactose | — | — | 88 | 176 | — | — | 54.54 | 300 |
| Vivasol ® [(2)] | — | — | — | — | 3.63 | 20 | 3.63 | 20 |
| Talc | — | — | — | — | 3.63 | 20 | 3.63 | 20 |
| Total weight per tablet (mg) | | 200 | | 200 | | 550 | | 550 |

(5) Vivapur ® 101 is Microcrystalline Cellulose commercially available from JRS Pharma
(6) Vivasol ® is croscarmellose sodium commercially available from JRS Pharma.

1.2.5.2. Process for the Preparation

Tablets 1 and 2 by Direct compression

A) Preparation of the Powdered Mixture

The amounts of cocrystal Form XIX of the present invention and the other excipients defined in previous Table were manually mixed.

B) Compression of Tablets

The resultant blend obtained in step (a) was compressed into tablets on an eccentric press (e.g. eccentric press machine Bonals) with a 9 mm cylindric biconvex tablet punch.

Tablets 3 by Dry Granulation Method

A) Preparation of the Powdered Mixture

The amounts of cocrystal Form XIX of the present invention, microcrystalline cellulose and croscarmellose defined in previous Table were manually mixed.

B) Compaction

The resultant blend obtained in step (a) was compacted into preforms (i.e. slugs) on an eccentric press (e.g. eccentric press machine Bonals) using a 19×10 mm capsular biconvex shape punch.

C) Compression of Tablets

The resultant preforms obtained in step b) were sieved through a sieve of 0.8 mm to obtain granules. To the resultant granules, talc and magnesium stearate were added and manually mixed. Then, the resultant mixture was compressed into tablets on an eccentric press (e.g. eccentric press machine Bonals) using a 17×8.5 mm oblong biconvex punch.

Tablets 4 by Dry Granulation Method

A) Preparation of the Powdered Mixture

The amounts of cocrystal Form XIX of the present invention, monohydrate lactose and croscarmellose defined in previous Table were manually mixed.

B) Compaction

The resultant blend obtained in step (a) was compacted into preforms (i.e. slugs) on an eccentric press (e.g. eccentric press machine Bonals) using a 19×10 mm capsular biconvex shape punch.

C) Compression of Tablets

The resultant preforms obtained in step b) were sieved through a sieve of 0.8 mm to obtain granules. To the resultant granules, talc and magnesium stearate were added and manually mixed. Then, the resultant mixture was compressed into tablets on an eccentric press (e.g. eccentric press machine Bonals) using a 17×8.5 mm oblong biconvex punch.

2. Cocrystals of Cannabinoids

2.1. Cocrystal Form I

Preparation Process Using L-Proline

A. Preparation by Wet Grinding

To a 2 mL Eppendorf tube containing CBD (20 mg, 0.064 mmol, 98.8% a/a HPLC—method 1), L-Proline (7.3 mg, 0.064 mmol, 1 eq.), 2 drops of acetonitrile and three stainless steel grinding balls were added before milling for 45 minutes at a rate of 30 Hz (3 cycles of 15 minutes) with a Retsch Ball Mill MM 400. After drying under vacuum (approx. 1-2 mbar) at room temperature cocrystal Form I of the present invention was obtained as a white solid.

B. Preparation by Slurrying

B.1. Preparation of Cocrystal Form I by Slurrying from High Purity CBD

To a round-bottomed flask equipped with magnetic stirring and $N_2$ atmosphere, containing a mixture of CBD (1.00 g, 3.18 mmol, 1.5 eq., 98.8% a/a HPLC—method 1) and L-proline (244 mg, 2.120 mmol), was added heptane (20 mL). The resulting mixture was seeded with CBD·L-Proline Form I and stirred at room temperature for 15 hours. Then, the reaction was monitored by XRPD analysis and an additional amount of CBD (584 mg, 1.85 mmol, 0.87 eq.) was added until complete conversion of L-proline was observed. The suspension was filtered through a sinter funnel (porosity n°3) and washed with 3×3.0 mL of heptane. After drying under vacuum at room temperature, cocrystal Form I of the present invention was obtained as a white solid (662 mg, 31%).

Figure 2:
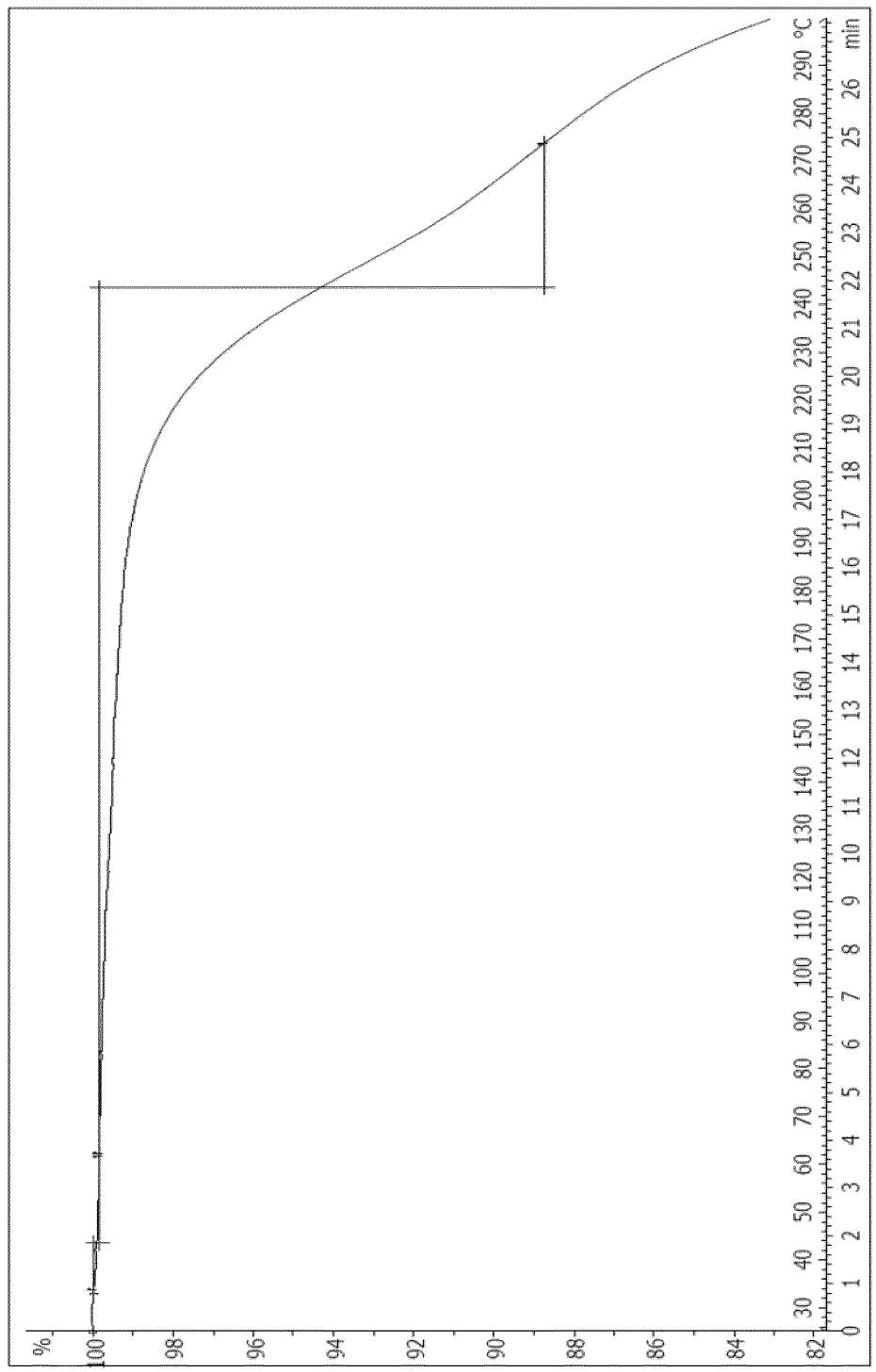
FIG. 2 shows the TGA of cocrystal Form I. The thermogram expresses weight loss (% w/w) versus temperature (° C.).

The cocrystal Form I thus obtained shows an X-ray powder diffractogram (XRPD) as in FIG. 1, a TGA as in FIG. 2. The cocrystal Form I thus obtained also shows the $^1$H NMR and the DSC spectra disclosed above. The TGA shows that it is not a stoichiometric hydrate.

Figure 5:
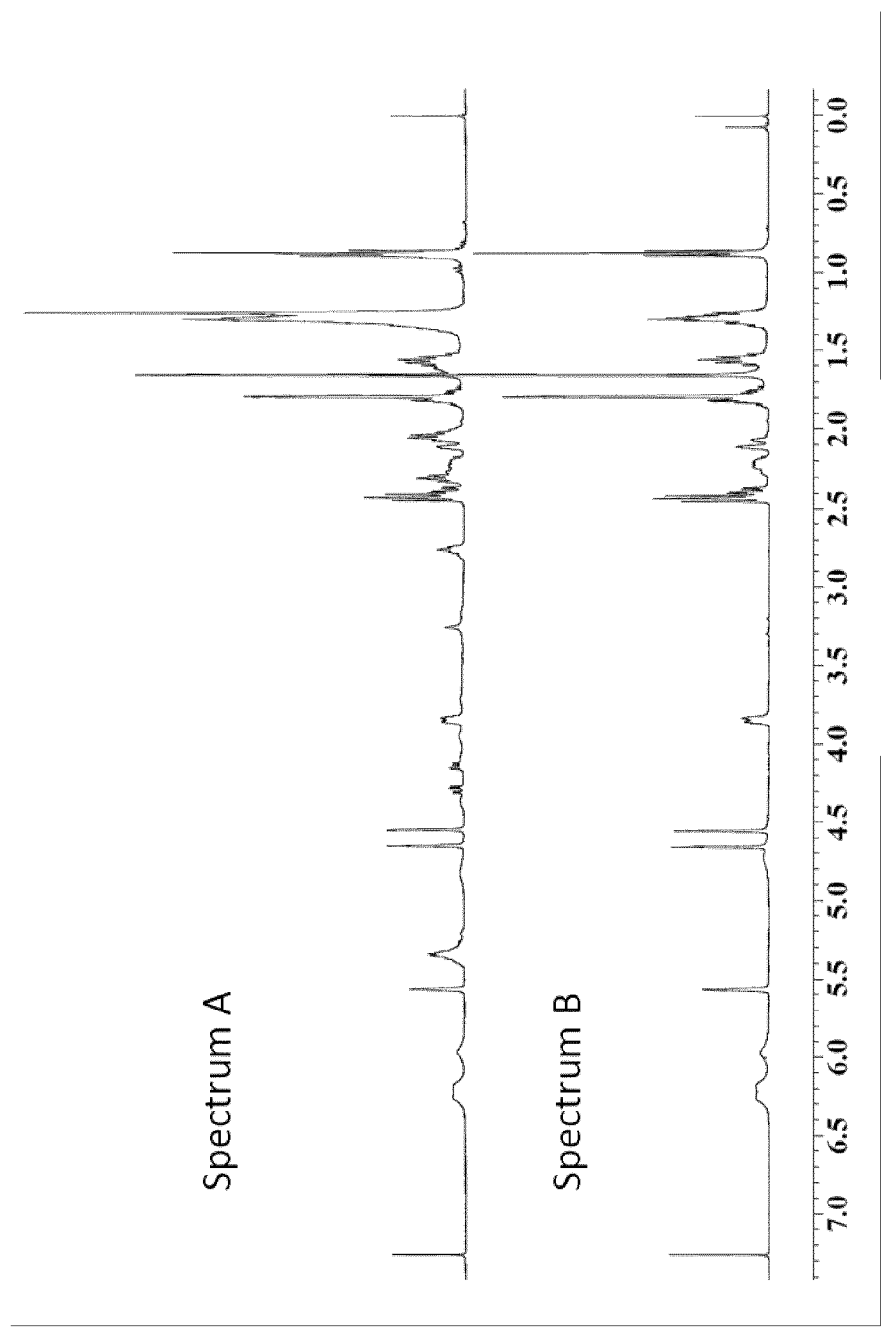
FIG. 5 shows the 1H NMR spectrum of the *Cannabis sativa* flower extract containing 50% w/w of CBD (sample 1) used as starting material in Example B.2 (Spectrum A) and the 1H NMR spectrum of the CBD recovered after dissociation of the cocrystal Form I obtained in Example B.2 (Spectrum B).

B.2. Purification Process of CBD from *Cannabis sativa* Flower Extract by Cocrystallization of Form I Preparation of Cocrystal Form I To a round-bottomed flask equipped with magnetic stirring and $N_2$ atmosphere, containing a mixture of *Cannabis sativa flower fraction about* 50% w/w CBD (100 mg, 0.159 theoretical mmol; 1H NMR of FIG. 5 spectrum A) and L-proline (18.3 mg, 0.159 mmol), was added heptane (1 mL). The resulting mixture was seeded with the cocrystal Form I of the present invention and stirred at room temperature for 15 h. The suspension was filtered through a sinter funnel (porosity n°3) and washed with 3×0.2 mL of heptane. After drying under vacuum at room temperature, cocrystal Form I containing traces of L-proline was obtained as a white solid (51 mg).

Dissociation of CBD from Cocrystal Form I

The cocrystal Form I thus obtained was dissolved in 5 mL of a mixture of heptane:water (1:1), the heptane phase was washed with water (2×1 mL) and dried with anhydrous Na$_2$SO$_4$ before eliminating the solvent under reduced pressure and vacuum. Thus, CBD was recovered as a white pasty solid (35 mg, 35% overall yield from a maximum of 50% yield, 99.4% a/a HPLC—method 1; 1H NMR of FIG. 5 spectrum B).

Figure 6:
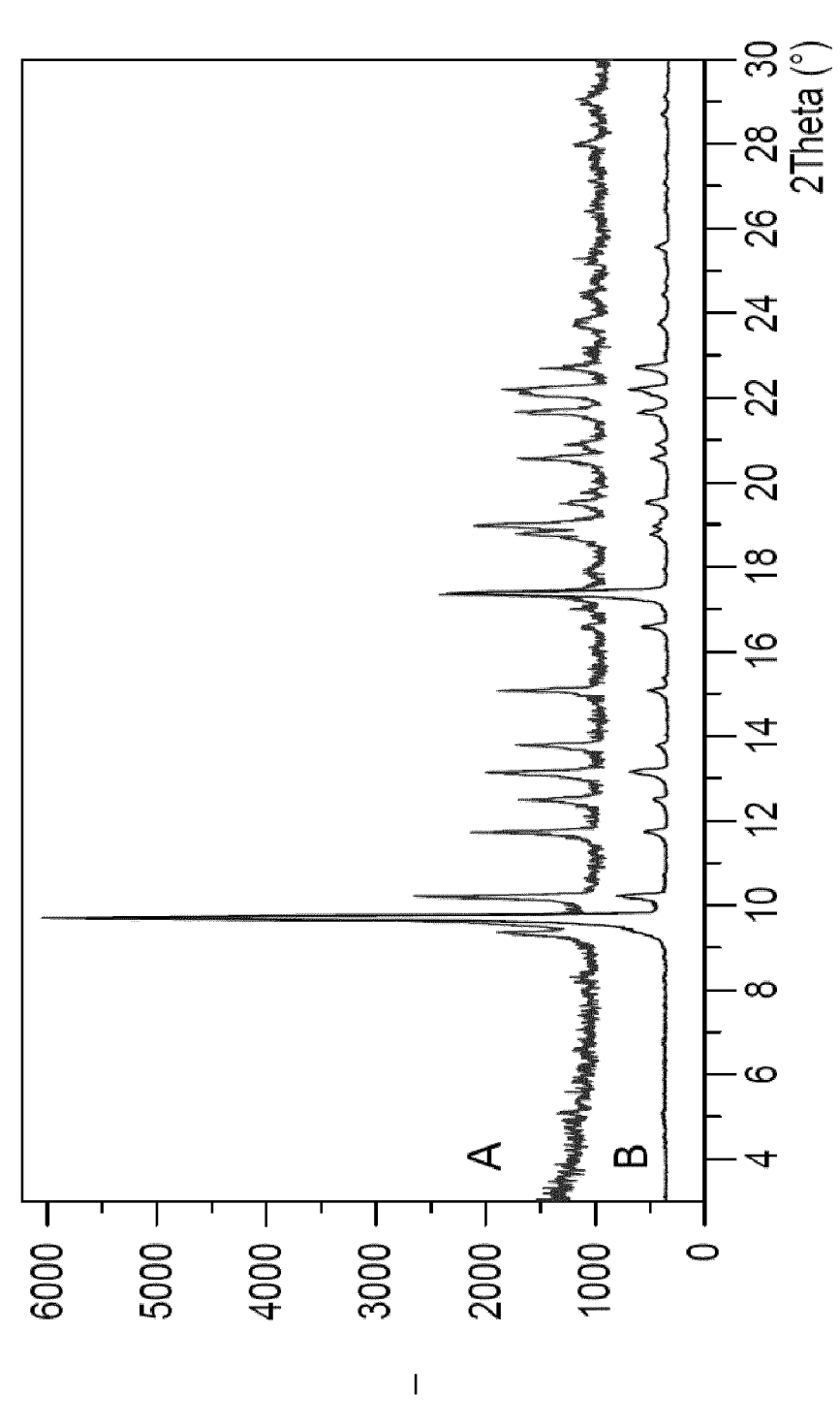
FIG. 6 shows the X-ray powder diffractogram (XRPD) of pure commercially available CBD (diffractogram B) and the X-ray powder diffractogram (XRPD) of CBD isolated from the cocrystal Form I obtained in Example B.2. (diffractogram A). The spectrum expresses intensity (I; counts) versus degrees 2 theta (°).

CBD thus obtained shows an X-ray powder diffractogram (XRPD) (cf. FIG. 6 diffractogram B) identical to pure commercial CBD in FIG. 6 diffractogram spectrum A. Comparison of the $^1$H NMR spectra and HPLC analyses between *Cannabis sativa* flower extract containing about 50% w/w of CBD used as starting material and CBD recovered from the cocrystallization of Form I (Example B.2.) purification process indicates an excellent purification (see also purification study in section 4 below).

B.3. Purification Process of CBD Synthetically Obtained by Cocrystallization of Form I Preparation of CBD A crude of CBD having a purity of 62% a/a measured by GC was obtained following the synthetic process disclosed in Example 3 page 80 of the PCT patent application WO20061313941 and in Example 8 page 45 of the PCT patent application WO2006053766.

Preparation of Cocrystal Form I

To a round flask equipped with magnetic stirring and N$_2$ atmosphere, containing a mixture of crude CBD disclosed in previous step (100 mg, 0.318 mmol; 62% a/a GC) and L-Proline (36.6 mg, 0.318 mmol, 1 eq.) was added heptane (15 mL). The resulting mixture was seeded with cocrystal Form I of the present invention and stirred at room temperature for 15 hours. To the suspension thus obtained 0.5 mL of heptane was added and then, the suspension was filtered through a sinter funnel (porosity n°3) and washed with 3×0.2 mL of heptane. After drying under vacuum at room temperature, a white solid (84 mg) corresponding to cocrystal Form I of the present invention was obtained as a mixture with traces of L-Proline (according to XRPD analysis).

Dissociation of CBD from Cocrystal Form I

The cocrystal Form I thus obtained (69 mg) was dissolved in 120 V of a mixture of heptane:water (2:1). After decanting, the aqueous phase was washed with heptane (3×20 V). Then organic extracts were reunified and washed with aqueous NaCl saturated solution and dried over anhydrous Na$_2$SO$_4$, before eliminating the solvent under reduced pressure and vacuum. Thus, CBD was recovered as a yellow oil (33 mg, 62% purity of crude material, 93.13% a/a GC) shows an X-ray powder diffractogram (XRPD) identical to pure commercial CBD in FIG. 6 diffractogram spectrum A.

Impurity Profile of CBD

A comparative study of the impurity profile of CBD used as a starting material having a purity of 62% a/a measured by GC and obtained by the synthetic processes disclosed in PCT patent applications WO20061313941 and WO2006053766, and the CBD obtained after dissociation of the cocrystal Form I of the present invention was performed.

The following Table shows the impurity profile measured by GC and expressed in % a/a of both CBDs:

| CBD | CBD | Regio-CBD[1] | Iso-THC[2] | THC | Dimer 1 | Dimer 2 |
|---|---|---|---|---|---|---|
| CBD starting material | 62.39% | 0.48% | 2.05% | 1.48% | 25.15% | 1.81% |
| CBD after dissociation from cocrystal | 93.13% | 0.39% | 0.62% | 0.33% | 3.36% | 0.25% |

[1]Regio-CBD is the common name of the compound 4-[(1R,6R)-3-methyl-6-(1-methylethenyl)-2-cyclohexen-1-yl]-5-pentyl-1,3-benzenediol, also known as abnormal CBD
[2]Iso-THC is the common name of the compound iso-tetrahydrocannabinol As it is shown in the above Table, according to GC analysis, all the main impurities of the crude CBD decreased after the purification by cocrystallization. Further purification steps by cocrystallization could lead to higher purity.

2.2. Cocrystal Form II

Preparation Process

A. Preparation by Wet Grinding

To a 2 mL Eppendorf tube containing CBD (20 mg, 0.064 mmol, 98.8% a/a HPLC—method 1), betaine (9.3 mg, 0.064 mmol, 1 eq.), 2 drops of isobutylacetate and three stainless steel grinding balls were added before milling for 45 minutes at a rate of 30 Hz (3 cycles of 15 minutes) with a Retsch Ball Mill MM 400. After a drying under vacuum (approx. 1-2 mbar) at room temperature, cocrystal Form II of the present invention was obtained as a white solid (quantitative yield).

B. Preparation by Slurrying

To a closed tube equipped with magnetic stirring and N$_2$ atmosphere, containing a mixture of CBD (50 mg, 0.159 mmol, 2 eq., 98.8% a/a HPLC—method 1) and betaine (9.3 mg, 0.080 mmol), was added heptane (0.5 mL). The resulting mixture was seeded with cocrystal Form II and stirred at room temperature for 15 hours. The suspension was filtered through a sinter funnel (porosity n°3) and washed with 2×0.1 mL of heptane. After drying under vacuum at room temperature, cocrystal Form II was obtained as a white solid (34 mg, 50%).

The cocrystal Form II thus obtained shows an X-ray powder diffractogram (XRPD) as in FIG. 3; and it also shows the $^1$H NMR and the DSC spectra disclosed above.

2.3. Cocrystal Form III

Preparation Process

A. Preparation by Wet Grinding

To a 2 mL Eppendorf tube containing CBD (20 mg, 0.064 mmol), L-carnitine (10.3 mg, 0.064 mmol, 1 eq.), 2 drops of cyclohexane and three stainless steel grinding balls were added before milling for 45 minutes at a rate of 30 Hz (3 cycles of 15 minutes) with a Retsch Ball Mill MM 400. After a drying under vacuum (approx. 1-2 mbar) at room temperature, pure cocrystal Form III was obtained as a white solid.

B. Preparation by Slurrying

To a round-bottomed flask equipped with magnetic stirring containing a mixture of CBD (300 mg, 0.954 mmol, 98.8% a/a HPLC—method 1) and L-carnitine (307 mg, 1.908 mmol, 2 eq.), was added heptane (3 mL). The resulting mixture was seeded with cocrystal Form III and stirred at room temperature for 15 hours. The suspension was filtered through a sinter funnel (porosity n°3) and washed with 2×1.0 mL of heptane. After drying under vacuum at room temperature, cocrystal Form III was obtained as a white solid (483 mg, 80%).

The cocrystal Form III thus obtained shows an X-ray powder diffractogram (XRPD) as in FIG. 4; and it also shows the $^1$H NMR and DSC spectra disclosed above.

2.4. Cocrystal Form IV
Preparation Process by Slurring from High Purity CBD

To a cylindrical vial equipped with magnetic stirring and N$_2$ atmosphere, containing a mixture of CBD (399 mg, 1.269 mmol, 2 eq.) and D-proline (74 mg, 0.643 mmol), was added heptane (4 mL). The resulting mixture was stirred at room temperature overnight. Then, additional heptane was added (4 mL) because solvent had almost completely evaporated. The suspension was filtered through a sinter funnel (porosity n°3) and washed with 3×0.4 mL of heptane. After drying under vacuum at room temperature, cocrystal Form IV of the present invention was obtained as a white solid (264 mg, 48%).

The cocrystal Form IV thus obtained shows an X-ray powder diffractogram (XRPD) as in FIG. 7; and it also shows the $^1$H NMR and DSC spectra disclosed above.

2.5. Cocrystal Form V
Preparation Process by Slurring from High Purity CBD

To a cylindrical vial equipped with magnetic stirring and N$_2$ atmosphere, containing a mixture of CBD (399 mg, 1.269 mmol, 2 eq.) and DL-proline (74 mg, 0.643 mmol), was added heptane (4 mL). The resulting mixture was stirred at room temperature overnight. Then, additional heptane was added (3 mL) because solvent had partially evaporated. The suspension was filtered through a sinter funnel (porosity n°2) and washed with 3×0.4 mL of heptane. After drying under vacuum at room temperature, cocrystal Form V of the present invention was obtained as a white solid (252 mg, 46%).

The cocrystal Form V thus obtained shows an X-ray powder diffractogram (XRPD) as in FIG. 9; and it also shows the $^1$H NMR and DSC spectra disclosed above.

2.6. Cocrystal Form VI
Preparation Process by Slurrying from High Purity CBD

To a test tube equipped with magnetic stirring, containing a mixture of CBD (79 mg, 0.251 mmol, 3 eq.) and (2S,3aS,7aS)-octahydro-1H-indole-2-carboxylic acid (14 mg, 0.084 mmol), was added heptane (0.55 mL). The resulting mixture was stirred at room temperature overnight. The suspension was filtered through a sinter funnel (porosity n°3) and washed with 3×0.08 mL of heptane. After drying under vacuum at room temperature, cocrystal Form VI (possibly contaminated with (2S,3aS,7aS)-octahydro-1H-indole-2-carboxylic acid) of the present invention was obtained as a white solid (25.2 mg, 48%).

The cocrystal Form VI thus obtained shows an X-ray powder diffractogram (XRPD) as in FIG. 12, a DSC as in FIG. 13. The cocrystal Form VI thus obtained also shows the $^1$H NMR disclosed below.

2.7. Cocrystal Form VII
Preparation Process A

In a test tube equipped with magnetic stirrer THC (23.7 mg, 0.08 mmol, 94% a/a measured by GC obtained in Comparative Example 4.2a below), L-proline (9.3 mg, 0.08 mmol, 1 equivalent) and heptane (0.25 mL, 10 V) were added. The suspension was stirred at room temperature overnight to obtain a dense suspension. Heptane (0.25 mL, 10 V) was added and stirred for 4 h. The suspension was centrifuged, decanted and dried under vacuum (approx. 1 mbar, room temperature) overnight to obtain cocrystal Form VII of the present invention mixed with L-proline as a white solid.

Preparation Process B

In a 25 mL round-bottomed flask equipped with magnetic stirrer and N$_2$ atmosphere THC (1.00 g, 3.18 mmol, 95% a/a measured by GC obtained in Example 4.2b below), L-proline (219.7 mg, 1.91 mmol, 0.6 equivalents) and heptane (10 mL, 10 V) were added. The suspension was stirred at room temperature for 2 days and a dense suspension was obtained. Heptane (2 mL, 2 V) was added and it was stirred for 1 h. The suspension was filtered through a sintered funnel (porosity 3), washed with heptane (2×2 mL, 2×2 V) and dried under vacuum (approx. 1 mbar, room temperature) overnight to obtain cocrystal Form VIII of the present invention as a white solid (704 mg, 86% yield).

The cocrystal Form VII thus obtained shows an X-ray powder diffractogram (XRPD) as in FIG. 14, a DSC as in FIG. 15. The cocrystal Form VII thus obtained also shows the $^1$H NMR spectra disclosed above.

2.8. Cocrystal Form VIII
Preparation Process A

In a test tube equipped with magnetic stirrer THC (24.3 mg, 0.08 mmol, 94% a/a measured by GC obtained in Comparative Example 4.2a below), D-proline (9.7 mg, 0.08 mmol, 1 equivalents) and heptane (0.38 mL, 15 V) were added. The suspension was stirred at room temperature for 3 h to obtain a dense suspension. Heptane (0.12 mL, 5 V) was added and it was stirred at room temperature overnight. The suspension was filtered through a sintered funnel (porosity 3), washed with heptane (0.12 mL, 5 V) and dried under vacuum (approx. 1 mbar, room temperature) overnight to obtain cocrystal Form VIII of the present invention mixed with D-proline as a white solid.

Preparation Process B

In a 25 mL round-bottomed flask equipped with magnetic stirrer and N$_2$ atmosphere THC (1.00 g, 3.18 mmol, 95% a/a measured by GC obtained in Example 4.2b below), D-proline (219.7 mg, 1.91 mmol, 0.6 equivalents) and heptane (10 mL, 10 V) were added. The suspension was stirred at room temperature for 2 days and was filtered through a sintered funnel (porosity 3), washed with heptane (2×2 mL, 2×2 V) and dried under vacuum (approx. 1 mbar, room temperature) overnight to obtain cocrystal Form VIII of the present invention as a white solid (782 mg, 96% yield).

The cocrystal Form VIII thus obtained shows an X-ray powder diffractogram (XRPD) as in FIG. 16, a DSC as in FIG. 17. The cocrystal Form VIII thus obtained also shows the $^1$H NMR spectra disclosed above.

2.9. Cocrystal Form IX
Preparation of Delta 8-Tetrahydrocannabinol delta8-tetrahydrocannabinol (delta8-THC) having a purity of about 97.2% a/a measured by HPLC (method 1) was obtained after column chromatography purification of the crude obtained from the CBD.

Preparation Process of the Cocrystal

In a test tube equipped with magnetic stirrer delta8-THC (24.7 mg, 0.08 mmol), L-proline (5.5 mg, 0.05 mmol, 0.6 equivalents) and heptane (0.25 mL, 10 V) were added. The suspension was stirred at room temperature for 3 h to obtain a dense suspension. Heptane (0.25 mL, 10 V) was added and stirred overnight. The suspension was filtered and dried under vacuum (about 1 mbar at room temperature) for 4 h. Cocrystal Form IX of the present invention was obtained as a white solid.

The cocrystal Form IX thus obtained shows an X-ray powder diffractogram (XRPD) as in FIG. 18. HPLC analysis indicated a significant purification of $\Delta^8$-THC (ca. 99.4% a/a HPLC—method 1).

2.10. Cocrystal Form X

Preparation of Delta8-THC

A crude of delta 8-tetrahydrocannabinol (delta8-THC) having a purity of about 97.2% a/a measured by HPLC (method 1) was obtained after column chromatography purification of the crude obtained from the CBD.

Preparation Process of the Cocrystal

In a test tube equipped with magnetic stirrer delta8-THC (26.2 mg, 0.08 mmol), D-proline (6.2 mg, 0.08 mmol, 0.6 equivalents) and heptane (0.25 mL, 10 V) were added. The suspension was stirred at room temperature overnight. The white suspension was filtered through a sintered funnel (porosity 4), washed with heptane (0.1 mL, 4 V) and dried under vacuum (about 1 mbar at room temperature) for 3 h. Cocrystal Form X of the present invention was obtained as a white solid.

The cocrystal Form X thus obtained shows an X-ray powder diffractogram (XRPD) as in FIG. 19.

2.11. Cocrystal Form XI

Preparation of CBN

CBN used for the cocrystal screening was prepared directly from CBD by reaction with iodine in toluene at 110° C. (following the process disclosed in *J. Nat. Prod.* 2018, vol. 81(3), pp. 630-633). Crude CBN (ca. 81% a/a HPLC) and CBN purified by chromatographic column (ca. 95-97% a/a HPLC) were used as starting material.

Preparation Process of the Cocrystal

Method 1: In an Eppendorf tube equipped with a magnetic stirrer bar, CBN (30 mg, 0.097 mmol—95% a/a HPLC), betaine hydrate (11.3 mg, 0.083 mmol, 0.85 eq.) and heptane (0.6 mL, 20V) were added. The resulting solution was stirred at RT overnight. The precipitated solid was centrifuged, the supernatant solution decanted and the solid dried under vacuum (approx. 1-2 mbar, RT) overnight. Form XI of the present invention was obtained as a mixture with betaine hydrate according to XRPD.

Method 2: In a flask equipped with a magnetic stirrer bar, CBN (130 mg, 0.418 mmol—81% a/a HPLC), betaine hydrate (28.2 mg, 0.195 mmol, 0.5 eq.) and heptane (2.3 mL, 17 V) were added. The resulting suspension was stirred at RT overnight. The solid was filtered through a sintered funnel (porosity 3), washed with heptane (2×0.2 mL) and dried under vacuum (approx. 1 mbar, RT) overnight. Form XI of the present invention was obtained as an off-white solid (70.3 mg, 40% yield) with 1:1 molar ratio (CBN:betaine).

The cocrystal Form XI thus obtained shows an X-ray powder diffractogram (XRPD) as in FIG. 20.

2.12. Cocrystal Form XII

Preparation of CBN was Performed Following the Process as Disclosed Above for Cocrystal Form XI.

Preparation Process of the Cocrystal

Method 1: In an Eppendorf tube equipped with a magnetic stirrer bar, CBN (30 mg, 0.097 mmol—95% a/a HPLC), L-Proline (11.1 mg, 0.097 mmol, 1 eq.) and heptane (0.6 mL, 20V) were added. The resulting solution was stirred at RT overnight. The precipitated solid was centrifuged, the supernatant solution decanted and the solid dried under vacuum (approx. 1-2 mbar, RD overnight. Form XII of the present invention was obtained as an off-white solid as a mixture with L-Proline according to XRPD.

Method 2: In a flask equipped with a magnetic stirrer bar, CBN (200 mg, 0.644 mmol—97% a/a HPLC), L-Proline (18.5 mg, 0.161 mmol, 0.25 eq.) and heptane (2 mL, 10 V) were added. The resulting suspension was stirred at RT overnight. The solid was filtered through a sintered funnel (porosity 3), washed with heptane (3×0.2 mL) and dried under vacuum (approx. 1 mbar, RD overnight. Form XII of the present invention was obtained as an off-white solid (44 mg, 16% yield) with 1:1 molar ratio (CBN:L-Proline).

The cocrystal Form XII thus obtained shows an X-ray powder diffractogram (XRPD) as in FIG. 22.

2.13. Cocrystal Form XIII

Preparation of CBN was Performed Following the Process as Disclosed Above for Cocrystal Form XI.

Preparation Process of the Cocrystal

In a flask equipped with a magnetic stirrer bar, CBN (150 mg, 0.483 mmol—81% a/a HPLC), L-Proline (28 mg, 0.242 mmol, 0.5 eq.) and heptane (2.5 mL, 17 V) were added. The resulting suspension was stirred at RT overnight. The solid was filtered through a sintered funnel (porosity 3), washed with heptane (2×0.3 mL) and dried under vacuum (approx. 1 mbar, RT) overnight. Form XIII of the present invention was obtained as an off-white solid (87 mg, 40% yield) with 1:1 molar ratio (CBN:L-Proline).

The cocrystal Form XIII thus obtained shows an X-ray powder diffractogram (XRPD) as in FIG. 24.

2.14. Cocrystal Form XIV

Preparation of CBN was Performed Following the Process as Disclosed Above for Cocrystal Form XI.

Preparation Process of the Cocrystal

In a flask equipped with a magnetic stirrer bar, CBN (180 mg, 0.580 mmol—81% a/a HPLC), D-Proline (26 mg, 0.230 mmol, 0.4 eq.) and heptane (1.5 mL, 10 V) were added. The resulting suspension was stirred at RT overnight. The solid was filtered through a sintered funnel (porosity 3), washed with heptane (2×0.3 mL) and dried under vacuum (approx. 1 mbar, RT) overnight. Form XIV of the present invention was obtained as an off-white solid (85 mg, 40% yield) with 1:1 molar ratio (CBN:D-Proline).

The cocrystal Form XIV thus obtained shows an X-ray powder diffractogram (XRPD) as in FIG. 26.

2.15. Cocrystal Form XV

Preparation of CBN was Performed Following the Process as Disclosed Above for Cocrystal Form XI.

Preparation Process of the Cocrystal

Method 1: In a flask equipped with a magnetic stirrer bar, CBN (100 mg, 0.322 mmol—97% a/a HPLC), D-Proline (18 mg, 0.161 mmol, 0.5 eq.) and heptane (2 mL, 20 V) were added. The resulting suspension was stirred at RT overnight. The solid was filtered through a sintered funnel (porosity 3), washed with heptane (2×0.2 mL) and dried under vacuum (approx. 1 mbar, RD overnight. Form XV of the present invention was obtained as an off-white solid (41 mg, 30% yield) with 1:1 molar ratio (CBN:D-Proline).

The cocrystal Form XV thus obtained shows an X-ray powder diffractogram (XRPD) as in FIG. 28.

2.16. Cocrystal Form XVI

Preparation of CBG

CBG used was prepared directly by reaction between geraniol (1) and olivetol (2) in chloroform at RT in presence of PTSA (0.04 eq.) as disclosed in the state of the art (US2017283837, WO2014134281, WO2016/30828, US2017/298399, US2017362195, Tet. Lett. 1969, 5349, *Proceedings of Chemical Society* 1964, 82, *The Journal of Biological Chemistry* 1996, 271(21), 17411). After 18 h, CBG was recovered as a mixture with ca. 20% regio and ca. 5-15% disubstitued:

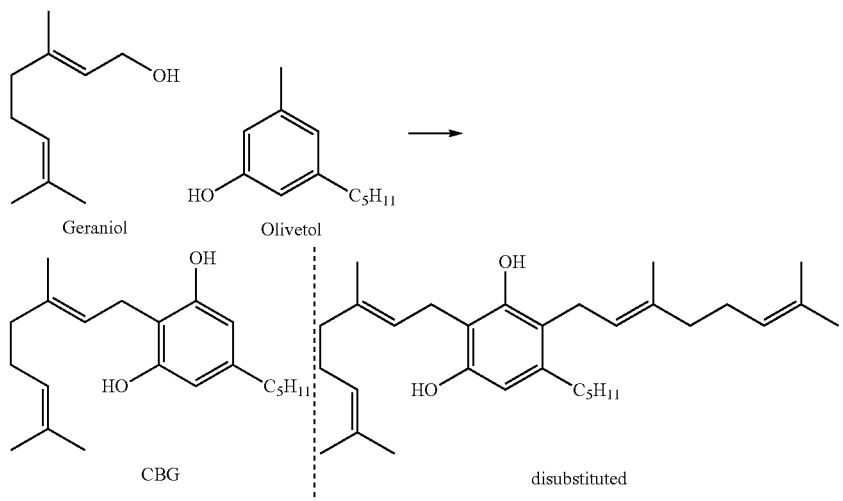

Purification by column chromatography (x2) afforded pure CBG (99.7% a/a HPLC—ca. 19% yield).

Preparation Process of the Cocrystal

Cocrystal Form XVI was obtained as a pure form by evaporation from a mixture in heptane with 5% v/v of EtOH (10 V, 1:1 molar ratio, CBG:betaine)

Cocrystal Form XVI was obtained contaminated with other crystalline forms by:
  Evaporation from a mixture in heptane (10 V, 1:1 molar ratio, CBG:betaine) (contaminated with other crystalline forms and betaine)
  Slurrying in cyclohexane or toluene (10 V, 1:1 molar ratio, CBG:betaine) (contaminated with betaine)
  Slurrying in heptane with 5% of EtOH at 0-5° C. (10 V, 1:1 molar ratio, CBG:betaine) (contaminated with betaine)
  Method 1: In a test tube equipped with magnetic stirrer, CBG (20 mg, 0.063 mmol), betaine (7.8 mg, 0.067 mmol, 1 equivalent) and heptane with 5% v/v of EtOH (0.2 mL, 10 V) were added. The suspension was stirred at RT but rapidly became a paste. The mixture was concentrated to dryness and dried under vacuum (approx. 1 mbar, RT) overnight. Cocrystal Form XVI of the present invention was obtained as a white solid.

The cocrystal Form XVI thus obtained shows an X-ray powder diffractogram (XRPD) as in FIG. 30.

2.17 Cocrystal Form XVII

Preparation of CBG was Performed Following the Process as Disclosed Above for Cocrystal Form XVI.

Preparation Process of the Cocrystal

Cocrystal Form XVII was obtained:
  as a mixture with other crystalline forms by slurrying in heptane (10 V, 1:1 molar ratio, CBG:L-carnitine). However, pure Form XVII was recovered after exposition of the recovered solid to ambient conditions.
  as a pure form by:
    Slurrying in toluene (10 V, 1:1 molar ratio, CBG:L-carnitine) (obtained as a gel)
    Slurrying in heptane with 5% of EtOH (10 V, 1:1 molar ratio, CBG:L-carnitine) (obtained as a paste)
  Method 1: In a test tube equipped with magnetic stirrer, CBG (50 mg, 0.16 mmol), L-carnitine (26 mg, 0.16 mmol, 1 equivalent) and heptane (0.5 mL, 10 V) were added. The resulting suspension was stirred at RT overnight. The solid was filtered through a sintered funnel (porosity 3) under N2, washed with heptane (0.1 mL, 2 V) and dried under vacuum (approx. 1 mbar, RT) overnight. A mixture of cocrystal Form XVII with other cocrystal forms (57 mg) was obtained which was transformed into cocrystal Form XVII of the present invention after exposition to ambient conditions overnight (1:1 molar ratio, CBG:L-carnitine according to 1H-NMR).

The cocrystal Form XVII thus obtained shows an X-ray powder diffractogram (XRPD) as in FIG. 32.

2.18 Cocrystal Form XVIII

Preparation of CBDV

CBDV used as starting material in the present invention was performed with a process similar to that used to prepare synthetic CBD (5-propylresorcinol was used as starting material instead of olivetol). After crystallization from the crude, CBDV was obtained with a purity of ca. 96% a/a according to HPLC.

Preparation Process of the Cocrystal

Cocrystal Form XVIII was obtained as a pure form by slurrying in iBuOH (4 V, 3:2 molar ratio, CBDV:L-proline.

Method 1: In a test tube equipped with a magnetic stirrer bar, CBDV (50 mg, 0.175 mmol), L-proline (10 mg, 0.087 mmol, 2 eq.) and isobutanol (0.25 mL, 5 V) were added. The resulting solution was stirred at RT for 1 week. The solid precipitated was centrifuged, the supernatant solution decanted and the solid dried under vacuum (approx. 1-2 mbar, RT) overnight. Cocrystal Form XVIII of the present invention was obtained as an off-white solid.

Method 2: In a test tube equipped with a magnetic stirrer bar, CBDV (100 mg, 0.349 mmol), L-proline (27 mg, 0.233 mmol, 1.5 eq.) and isobutanol (0.4 mL, 4 V) were added. The resulting suspension was stirred at RT overnight. The solid was filtered through a sintered funnel (porosity 3), washed with isobutanol (2×0.15 mL, 2×1.5 V) and dried under vacuum (approx. 1 mbar, RD overnight. Cocrystal Form XVIII of the present invention was obtained as an off-white solid (51 mg, 27% yield) with 1:1 molar ratio (CBDV:L-proline).

The cocrystal Form XVIII thus obtained shows an X-ray powder diffractogram (XRPD) as in FIG. 34.

2.19 Cocrystal Form XIX

Preparation of CBDV was Performed Following the Process as Disclosed Above for Cocrystal Form XIX.

Preparation Process of the Cocrystal

Cocrystal Form XIX was obtained as a pure form by slurrying in IPA (2 V, 2:3 molar ratio, CBDV:L-carnitine).

Method 1: To a 2 mL Eppendorf tube containing CBDV (20 mg, 0.070 mmol), L-carnitine (11 mg, 0.070 mmol, 1 eq.) and three stainless steel grinding balls, 2 drops of IPA were added. The products were milled for 45 minutes at a rate of 30 Hz (3 cycles of 15 minutes) with a Retsch Ball Mill MM 400. After drying under vacuum (approx. 1-2 mbar, RT) overnight cocrystal Form XIX of the present invention contaminated with CBDV was obtained as a white solid.

Method 2: In a test tube equipped with a magnetic stirrer bar, CBDV (100 mg, 0.349 mmol), L-carnitine (84 mg, 0.524 mmol, 1.5 eq.) and IPA (0.2 mL, 2 V) were added. The resulting suspension was stirred at RT overnight. The mixture was filtered through a sintered funnel (porosity 3), washed with IPA (2×0.1 mL, 2×1 V) and dried under vacuum (approx. 1 mbar, RT) overnight. Form XIX of the present invention was obtained as an off-white solid (104 mg, 66% yield) with 1:1 molar ratio (CBDV:L-carnitine).

The cocrystal Form XIX thus obtained shows an X-ray powder diffractogram (XRPD) as in FIG. 36.

3. Stability Study 3.1. CBD

The aim of the study is to evaluate the stability of cocrystal Form I of the present invention.

Sample

Cocrystal Form I of the present invention obtained by the process disclosed in section 2.1.B.1.

Method

Cocrystal Form I (55 mg) is stored in an open vial and exposed to accelerated stability conditions (40° C. and 75±5% relative humidity) according to ICH guidelines (Guidance for Industry Q1A(R2) Stability Testing of New Drug Substances and Products—available on the website http://www.ich.org/products/guidelines/quality/quality-single/article/stability-testing-of-new-drug-substances-and-products.html on Aug. 4, 2017).

Results

Under the above mentioned conditions, cocrystal Form I of the present invention remained stable for at least three weeks according to XRPD.

3.2. THC

The aim of the study is to evaluate the stability of cocrystal Form VIII

Sample

Cocrystal Form VIII of the present invention obtained by the process disclosed in section 2.8.

Method

Cocrystal Form VIII and oily THC are exposed to two different stability conditions:

Condition 1: Cocrystal Form VIII (700 mg—96.5% a/a HPLC—method 2) and THC (700 mg—94.8% HPLC—method 2): Open vial under ambient conditions (21±4° C. and 43±13% relative humidity, exposed to laboratory light)

Condition 2: Cocrystal Form VIII (100 mg—95.9% a/a HPLC—method 2) and THC (100 mg—95.6% HPLC—method 2): Close vial stored at 40±2° C.

Results

According to HPLC (method 2), it was observed that cocrystal Form VIII remained chemically more stable than oily THC:

Chemical purity after 14 weeks under conditions 1:
    88.9% a/a Cocrystal Form VIII and 83.7% a/a oily THC Chemical purity after 10 weeks under conditions 2:
    89.1% a/a Cocrystal Form VIII and 76.6% a/a oily THC Furthermore, cocrystal Form VIII of the present invention remained stable according to XRPD.

4. Purification Study 4.1. CBD

The aim of this study is the measurement of the purity of the cocrystals of CBD of the present invention and the comparison with the purity of the CBD samples used as starting material and the CBD purified by cocrystallization of the cocrystal Form I.

Samples

Sample 1: Commercial *Cannabis sativa* flower extract containing 50% by weight of CBD in relation to the total weight of the extract.

Sample 2: Pure commercial CBD used as starting material in the CBD cocrystal preparation.

Sample 3: Pure CBD obtained from *Cannabis sativa* flower extract after purification by cocrystallization of Form I and the subsequent cocrystal dissociation step.

Method

Each sample (5 mg) was dissolved in methanol (5 mL) and injected (1 μL) for HPLC measurement in isocratic conditions (acetonitrile:water 80:20) with the detector measuring at 225 nm (HPLC method 1).

Results

The purity and the impurity profile of the CBD used as a starting material (Sample 1 and Sample 2) and that obtained after purification of Sample 1 (Sample 3) are disclosed in Table 11A. The purity and the impurity profile of the cocrystals Form I and Form II of the present invention prepared from Sample 1 are disclosed in Table 11B.

The purity of the starting materials, the cocrystals of the present invention, and the CBD obtained after dissociation of the cocrystals of the present invention as well as the amount of the impurities are expressed in area %.

TABLE 11A

| | | Impurity profile (Area %) | | |
|---|---|---|---|---|
| CBD sample | Purity (Area %) | Cannabidivarin | CBD C4 analogue[1] | THC[3] |
| Sample 1 | 98.00[1] | 0.88 | 0.28 | ND[4] |
| Sample 2 | 98.83 | 0.66 | 0.22 | 0.03 |
| Sample 3 | 99.66 | ND[4] | 0.16 | ND[4] |

[1]Most of the impurities are not detected by HPLC.
[2]CBD C4 analogue corresponds to 2-[(1R,6R)-6-isopropenyl-3-methylcyclohex-2-en-1-yl]-5-butylbenzene-1,3-diol.
[3]THC corresponds to tetrahydrocannabinol.
[4]ND stands for not detected.

TABLE 11B

| | | | Impurity profile (Area %) | | |
|---|---|---|---|---|---|
| Cocrystal of the invention | Starting compound | Purity (Area %) | Cannabidivarin | CBD C4 analogue[1] | THC[2] |
| Cocrystal Form I | Sample 1 | 99.26 | ND[5] | 0.19 | ND[5] |
| Cocrystal Form I | Sample 2 | 99.03[3] | 0.41 | 0.15 | 0.01 |

TABLE 11B-continued

| Cocrystal of the invention | Starting compound | Purity (Area %) | Impurity profile (Area %) | | |
|---|---|---|---|---|---|
| | | | Cannabidivarin | CBD C4 analogue[1] | THC[2] |
| Cocrystal Form II | Sample 2 | 99.03[4] | 0.50 | 0.28 | 0.02 |

[1] CBD C4 analogue corresponds to 2-[(1R,6R)-6-isopropenyl-3-methylcyclohex-2-en-1-yl]-5-butyllbenzene-1,3-diol.
[2] THC corresponds to tetrahydrocannabinol.
[3] Under the HPLC conditions, L-proline of cocrystal Form I is not detected.
[4] Under the HPLC conditions, betaine of cocrystal Form II is not detected.
[5] ND stands for not detected.

As shown in the Table above, the preparation of the cocrystals of the present invention allows for purifying the CBD, and especially crude CBD, with a less laborious, less expensive and more readily scalable process compared to the state of the art. The preparation of the cocrystals of the present invention allows for purifying the CBD when the CBD used as starting material has a purity about 50% w/w and even when the starting CBD already has high purity (about 98 area %), particularly cocrystals Form I, Form II and Form IV.

Dissociation of Form I obtained from Sample 1 in a biphasic heptane/water mixture led to CBD (Sample 3) with a slightly higher purity (99.66% a/a) than Form I (99.26% a/a), a significantly higher purity than Sample 1 (50% purity by weight, 98.00 a/a) and an overall yield of 35% (comprising cocrystallization and cocrystal dissociation steps from a maximum of 50% yield). Furthermore, the 1H NMR analysis shows that the coformers and impurities not detectable by UV are removed (see FIG. 5), the HPLC analysis shows that the impurities detectable by UV are also reduced. In fact, cannabidivarin is reduced from 0.88% a/a to a non-detectable amount and the CBD C4 analogue is reduced from 0.28% to 0.16% a/a, and XRPD analysis indicates the same crystalline form as commercial pure CBD (FIG. 6).

Furthermore, the preparation of the cocrystals from Sample 2 of the present invention also allows for reducing the amount of all the identified impurities. Particularly, the amount of THC is reduced by half.

4.2. THC

The aim of this study is to compare the purity improvement of the THC obtained by cocrystallization followed by dissociation of the cocrystal of the present invention in comparison with that obtained by chromatographic purification. It is worth noting that as THC is not crystalline, direct crystallization is not possible.

Comparative Example 4.2a

A crude THC having a purity of 77% a/a measured by GC was obtained following the process disclosed in Example II page 9 of the PCT patent application WO02070506.

From this crude, a chromatographic purification was performed to obtain THC with a purity of 94% a/a measured by GC with a yield of 49%. The chromatographic purification of the crude is performed using 40 g SiO$_2$-GOLD column and eluting the crude with a mixture of cyclohexane/20% Et$_2$O-cyclohexane.

Example 4.2b

Step 1. Cocrystal Formation

A crude THC having a purity of 77% a/a measured by GC was obtained following the process disclosed in Example II page 9 of the PCT patent application WO02070506.

In a 100 mL round-bottomed flask equipped with magnetic stirrer the THC crude (4.60 g, 14.6 mmol), L-proline (1.68 g, 14.6 mmol, 1 equivalent) and heptane (46 mL, 10 V) were added. The suspension was stirred at room temperature for 2 days and was filtered through a sintered funnel (porosity 3), washed with heptane (2×9 mL, 2×2 V) and dried under vacuum (approx. 1 mbar, room temperature) overnight to obtain cocrystal Form VII of the present invention mixed with L-proline as a white solid (4.66 g).

As it is shown in Examples 4.2a and 4.2b, the purification process of the present invention which involves the cocrystalization of THC allows obtaining THC in a high purity (equal to or higher than 95% a/a measured by GC) in a high yield (equal to or higher than 65%).

Step 2. Dissociation Process

In a 1 L round-bottomed flask equipped with magnetic stirrer cocrystal Form VII and L-proline mixture coming from step 1 (4.50 g) was dissolved in H$_2$O (180 mL, 40 V) and heptane (360 mL, 80 V). The suspension was stirred at room temperature for 10 minutes and decanted. Aqueous phase was extracted with heptane (3×90 mL, 3×15 V). The organic phase (optionally dried with Na$_2$SO$_4$) was concentrated to dryness obtaining THC as a pale brownish oil (2.80 g, 63% overall yield—2 steps) with a purity of 95% a/a measured by GC.

As shown above, the preparation of the cocrystals of the present invention allows for purifying THC, and especially crude THC, with a less laborious, less expensive and more readily scalable process compared to the state of the art.

4.3. CBN

The aim of this study is to observe the purity improvement of the CBN obtained by cocrystallization followed by dissociation of the cocrystal of the present invention in comparison with the purity of the CBN resulting from chromatographic purification. Although a crystalline form of CBN was described in the literature, it was not obtained during this study even from very pure CBN material. Therefore, it was not possible to compare the cocrystallization with a direct crystallization of CBN.

Step 1. Cocrystal Formation

CBN (1 g, 80.8%) was dissolved in 20 V heptane and betaine hydrate (377 mg, 2.79 mmol, 0.85 eq.) was added over the solution in order to obtain a suspension. Seeding with Form XI (obtained in method 2 of Example 2.11) was performed. The resulting mixture was stirred at RT overnight. The solids were isolated by filtration and washed with heptane (2×2 V) before drying under vacuum at RT overnight.

Cocrystal Form XI with residual betaine was obtained as a white solid (700 mg, 99.6% a/a measured by HPLC (method 2).

Step 2. Dissociation Process

Cocrystal Form XI with residual betaine (700 mg) obtained in previous step was dissolved in 120 V of a mixture heptane:water (2:1) and 4 V of HCl 1 M. After separation of the organic phase, the aqueous phase was extracted with heptane (3×20 V). Then the combined organic phase was washed with water (3 times) until reach neutral pH. Subsequently the organic phase was dried over anhydrous MgSO$_4$ and evaporated to dryness under reduced pressure and vacuum. CBN was obtained as a colorless oil (344 mg, 99.6% a/a measured by HPLC (method 2) 43% overall yield (two steps)).

4.4. CBDV

The aim of this study is the measurement of the purity of the CBDV obtained by cocrystallization followed by dissociation of the cocrystal of the present invention in comparison with the purity of the CBDV resulting from direct crystallization.

Step 1. Cocrystal Formation

Preparation of Cocrystal Form XIX by slurrying from CBDV crude coming from the synthesis (with purification step).

In a test tube equipped with a magnetic stirrer bar, CBDV (300 mg, 1.047 mmol), L-carnitine (338 mg, 2.095 mmol, 2 eq.) and IPA (0.6 mL, 2 V) were added. A thick suspension was obtained and IPA (0.3 mL, 1 V) was added. The resulting suspension was stirred at RT overnight. The mixture was filtered through a sintered funnel (porosity 3), washed with IPA (2×0.3 mL, 2×1 V) and dried under vacuum (approx. 1 mbar, RT) overnight. Cocrystal Form XIX of the present invention was obtained as an off-white solid (424 mg, 91% yield) with 1:1 molar ratio (CBDV:L-carnitine).

Step 2. Dissociation Process: Preparation of CBDV from Cocrystal Form XIX

In a 50 mL round-bottomed flask equipped with magnetic stirrer cocrystal Form XIX coming from step 1 (300 mg) was suspended in $H_2O$ (12 mL, 40 V) and toluene (12 mL, 40 V). The suspension was stirred at RT for 10 minutes and decanted. The aqueous phase was extracted with toluene (3×12 mL, 3×40 V). The organic extracts were combined (optionally dried with $Na_2SO_4$) and concentrated to dryness obtaining an off-white solid (125 mg, 59% overall yield—2 steps) with a purity of 98.8% a/a measured by HPLC (method 2).

Good purification results were also observed by direct crystallization of CBDV in heptane. The main impurity detected in CBDV obtained (ca. 3% a/a measured by HPLC method 2) is the compound derived from the isopropyl impurity formed in the preparation of 1,3-dimethoxy-5-propylbenzene according to the 1H NMR spectrum. However, it was checked that this impurity was not removed from further recrystallizations in heptane, while it can be easily removed by cocrystallization leading to higher purity.

As shown above, the preparation of the cocrystals of the present invention allows for purifying CBN, and especially crude CBN, with a less laborious, less expensive and more readily scalable process compared to the state of the art.

CITATION LIST

1. T. Petrzilka et al. "synthese and chiralität des (–)-cannabidiols vorläufige mitteilung". *Helvetica Chimica Acta.* 1967, vol. 50(2), pp. 719-23
2. T. Petrzilka et al. "synthese von haschisch-inhaltsstoffen. 4. Mitteilung". *Helvetica Chimica Acta.* 1969, vol. 52(4), pp. 1102-34
3. WO2009018389
4. *Tetrahedron Letters* 1985, vol. 26(8), pp. 1083
5. WO2006133941
6. WO2007041167
7. WO2015032519
8. *Biochemical Medicine,* 1973, vol. 8(3), pp. 341-344
9. WO2004026857A2-GW
10. *Preparative Biochemistry,* 1973, vol. 3(3), pp. 209-220
11. Poster ACS, Philadelphia, 2016, Biotage
12. US2017008870A1
13. US4381399A
14. US2018325861
15. *Indian J. Pharm. Sci.* 2017, vol. 79(6), pp. 858-871
16. US2017283837
17. WO2014134281
18. WO2016/30828
19. US2017/298399
20. US2017362195
21. *Tet. Lett.* 1969, 5349,
22. *Proceedings of Chemical Society* 1964, 82,
23. *The Journal of Biological Chemistry* 1996, 271(21), 17411
24. *British Journal of Pharmacology,* 2018, 175 100-112
25. *Sci Rep,* 2016, 6:29789, 1-1526. *Chem Commun,* 1969, 7, 343-344
27. *Tetrahedron* 2017, 73, 5297-5301
28. *J. Nat. Prod.* 2018, 81 (3), 630-633
29. *Tet. Lett.* 1985, 26 (8), 1083-1086

For reasons of completeness, various aspects of the invention are set out in the following numbered clauses:

Clause 1. A solid composition comprising:
an effective amount of one or more cocrystals of a cannabinoid and a zwitterion coformer; and
one or more acceptable excipients or carriers;
wherein the effective amount of the cocrystal is from 1% to 80% by weight of the solid composition.

Clause 2. The solid composition according to clause 1, wherein effective amount of the cocrystal is from 10% to 40% by weight of the solid composition.

Clause 3. The solid composition according to any of the clauses 1 or 2, wherein the particle size of the cocrystal is from 50 μm to 250 μm.

Clause 4. The solid composition according to any of the clauses 1-3, wherein the solid composition is a hard capsule, a direct-compressed tablet and a dry granulation tablet.

Clause 5. The solid composition according to clause 4, wherein the solid composition is:
a hard capsule comprising:
from 1% to 80% by weight of one or more of the cocrystal of the cannabinoid;
from 20% to 99% by weight of one or more fillers; and
from 0.25% to 10% by weight of one or more glidants;
being the sum of components of the composition of 100% by weight;
or alternatively,
a dry-granulation tablet comprising:
from 1% to 80% by weight of one or more of the cocrystal of the cannabinoid;
from 20% to 99% by weight of one or more fillers;
from 1% to 15% by weight of one or more disintegrants;
from 0.25% to 10% by weight of one or more glidants; and
from 0.25% to 10% by weight of one or more lubricant;
being the sum of components of the composition of 100% by weight;
or alternatively,
direct-compressed tablet comprising:
from 1% to 80% by weight of one or more of the cocrystal of the cannabinoid;
from 20% to 99% by weight of one or more fillers; and
from 0.25% to 10% by weight of one or more glidants;
being the sum of components of the composition of 100% by weight.

Clause 6. The solid composition according to any of the clauses 1-5, wherein the cannabinoid is selected from the group consisting of Tetrahydrocannabinol, Cannabidiol, Cannabinol, Cannabigerol, Cannabichromene, Cannabicyclol, Cannabivarin, Tetrahydrocannabivarin, Cannabidivarin, Cannabichromevarin, Cannabigerovarin, Cannabigerol Monomethyl Ether, delta8-tetrahydrocannabinol and a mixture thereof.

Clause 7. The solid composition according to any of the clauses 1-6, wherein the coformer comprises a positively charged nitrogen atom and a negatively charged group distal to the positively charged nitrogen group on the zwitterion such that there is a separation by at least one carbon atom.

Clause 8. The solid composition according to any of the clauses 1-7, wherein the coformer is selected from the group consisting of L-proline, betaine, L-carnitine, D-proline and DL-proline.

Clause 9. The solid composition according to clause 8, wherein the cocrystal of the solid composition is selected from the group consisting of 2-[(1R,6R)-6-isopropenyl-3-methylcyclohex-2-en-1-yl]-5-pentylbenzene-1,3-diol and L-proline characterized by having an X-ray diffractogram that comprises characteristic peaks at 5.8, 11.1 and 15.8±0.3 degrees 2 theta at a Cu—K$_\alpha$ radiation, λ=1.5406 Å;

2-[(1R,6R)-6-isopropenyl-3-methylcyclohex-2-en-1-yl]-5-pentylbenzene-1,3-diol and betaine characterized by having an X-ray diffractogram that comprises characteristic peaks at 9.1, 10.7 and 18.4±0.3 degrees 2 theta at a Cu—K$_\alpha$ radiation, λ=1.5406 Å;

2-[(1R,6R)-6-isopropenyl-3-methylcyclohex-2-en-1-yl]-5-pentylbenzene-1,3-diol and L-carnitine characterized by having an X-ray diffractogram that comprises characteristic peaks at 6.8, 11.3 and 20.0±0.3 degrees 2 theta at a Cu—K$_\alpha$ radiation, λ=1.5406 Å;

2-[(1R,6R)-6-isopropenyl-3-methylcyclohex-2-en-1-yl]-5-pentylbenzene-1,3-diol and D-proline characterized by having an X-ray diffractogram that comprises characteristic peaks at 5.7, 11.2 and 15.7±0.3 degrees 2 theta at a Cu—K$_\alpha$ radiation, λ=1.5406 Å;

2-[(1R,6R)-6-isopropenyl-3-methylcyclohex-2-en-1-yl]-5-pentylbenzene-1,3-diol and DL-proline characterized by having an X-ray diffractogram that comprises characteristic peaks at 5.7, 11.1 and 15.7±0.3 degrees 2 theta at a Cu—K$_\alpha$ radiation, λ=1.5406 Å;

(−)-(6aR,10aR)-6,6,9-trimethyl-3-pentyl-6a,7,8,10a-tetrahydro-6H-benzo[c]chromen-1-ol and L-proline characterized by having an X-ray diffractogram that comprises characteristic peaks at 5.1, 11.5 and 20.5±0.3 degrees 2 theta at a Cu—K$_\alpha$ radiation, λ=1.5406 Å;

(−)-(6aR,10aR)-6,6,9-trimethyl-3-pentyl-6a,7,8,10a-tetrahydro-6H-benzo[c]chromen-1-ol and D-proline characterized by having an X-ray diffractogram that comprises characteristic peaks at 5.1, 11.4 and 20.6±0.3 degrees 2 theta at a Cu—K$_\alpha$ radiation, λ=1.5406 Å;

(6aR,10aR)-6,6,9-trimethyl-3-pentyl-6a,7,10,10a-tetrahydro-6H-benzo[c]chromen-1-ol and L-proline characterized by having an X-ray diffractogram that comprises characteristic peaks at 5.1, 18.7 and 20.5±0.3 degrees 2 theta at a Cu—K$_\alpha$ radiation, λ=1.5406 Å; and (6aR,10aR)-6,6,9-trimethyl-3-pentyl-6a,7,10,10a-tetrahydro-6H-benzo[c]chromen-1-ol and L-proline characterized by having an X-ray diffractogram that comprises characteristic peaks at 5.1, 16.1 and 20.4±0.3 degrees 2 theta at a Cu—K$_\alpha$ radiation, λ=1.5406 Å.

Clause 10. A cocrystal of a cannabinoid selected from (−)-(6aR,10aR)-6,6,9-trimethyl-3-pentyl-6a,7,8,10a-tetrahydro-6H-benzo[c]chromen-1-ol and (6aR,10aR)-6,6,9-trimethyl-3-pentyl-6a,7,10,10a-tetrahydro-6H-benzo[c]chromen-1-ol and a zwitterion coformer.

Clause 11. The cocrystal according to clause 10, wherein the coformer is selected from the group consisting of L-proline, D-proline and DL-proline.

Clause 12. The cocrystal according to any of the clauses 10 or 11, which is a cocrystal selected from the group consisting of:

(−)-(6aR,10aR)-6,6,9-trimethyl-3-pentyl-6a,7,8,10a-tetrahydro-6H-benzo[c]chromen-1-ol and L-proline characterized by having an X-ray diffractogram that comprises characteristic peaks at 5.1, 11.5 and 20.5±0.3 degrees 2 theta at a Cu—K$_\alpha$ radiation, λ=1.5406 Å;

(−)-(6aR,10aR)-6,6,9-trimethyl-3-pentyl-6a,7,8,10a-tetrahydro-6H-benzo[c]chromen-1-ol and D-proline characterized by having an X-ray diffractogram that comprises characteristic peaks at 5.1, 11.4 and 20.6±0.3 degrees 2 theta at a Cu—K$_\alpha$ radiation, λ=1.5406 Å;

(6aR,10aR)-6,6,9-trimethyl-3-pentyl-6a,7,10,10a-tetrahydro-6H-benzo[c]chromen-1-ol and L-proline characterized by having an X-ray diffractogram that comprises characteristic peaks at 5.1, 18.7 and 20.5±0.3 degrees 2 theta at a Cu—K$_\alpha$ radiation, λ=1.5406 Å; and (6aR,10aR)-6,6,9-trimethyl-3-pentyl-6a,7,10,10a-tetrahydro-6H-benzo[c]chromen-1-ol and L-proline characterized by having an X-ray diffractogram that comprises characteristic peaks at 5.1, 16.1 and 20.4±0.3 degrees 2 theta at a Cu—K$_\alpha$ radiation, λ=1.5406 Å.

Clause 13. A process for the preparation of the cocrystal as defined in any of the clauses 10-12, which comprises:

(c) slurring the cannabinoid with the coformer and an organic solvent; and (d) isolating the cocrystal thus obtained.

Clause 14. A process for the purification of a cannabinoid which comprises:

(e) dissociating a cocrystal as defined in any of the clauses 10-12 under such reaction conditions to obtain the cannabinoid; and (f) isolating the cannabinoid thus obtained.

The invention claimed is:

1. A cocrystal of a cannabinoid selected from (−)-(6aR,10aR)-6,6,9-trimethyl-3-pentyl-6a,7,8,10a-tetrahydro-6H-benzo[c]chromen-1-ol, (6aR,10aR)-6,6,9-trimethyl-3-pentyl-6a,7,10,10a-tetrahydro-6H-benzo[c]chromen-1-ol, 6,6,9-trimethyl-3-pentylbenzo[c]chromen-1-ol, 2-[(2E)-3,7-dimethylocta-2,6-dien-1-yl]-5-pentylbenzene-1,3-diol and 2-((1R,6R)-3-methyl-6-(prop-1-en-2-yl) cyclohex-2-enyl)-5-propylbenzene-1,3-diol and a zwitterion conformer, which is a cocrystal selected from the group consisting of:

(−)-(6aR,10aR)-6,6,9-trimethyl-3-pentyl-6a,7,8,10a-tetrahydro-6H-benzo[c]chromen-1-ol and L-proline characterized by having an X-ray diffractogram that comprises characteristic peaks at 5.1, 11.5 and 20.5±0.3 degrees 2 theta at a Cu-Kα radiation, λ=1.5406 Å;

(−)-(6aR,10aR)-6,6,9-trimethyl-3-pentyl-6a,7,8,10a-tetrahydro-6H-benzo[c]chromen-1-ol and D-proline characterized by having an X-ray diffractogram that comprises characteristic peaks at 5.1, 11.4 and 20.6±0.3 degrees 2 theta at a Cu-Kα radiation, λ=1.5406 Å;

(6aR,10aR)-6,6,9-trimethyl-3-pentyl-6a,7,10,10a-tetrahydro-6H-benzo[c]chromen-1-ol and L-proline characterized by having an X-ray diffractogram that comprises characteristic peaks at 5.1, 18.7 and 20.5±0.3 degrees 2 theta at a Cu-Kα radiation, λ=1.5406 Å;

(6aR,10aR)-6,6,9-trimethyl-3-pentyl-6a,7,10,10a-tetrahydro-6H-benzo[c]chromen-1-ol and D-proline characterized by having an X-ray diffractogram that comprises characteristic peaks at 5.1, 16.1 and 20.4±0.3 degrees 2 theta at a Cu-Kα radiation, λ=1.5406 Å;

6,6,9-trimethyl-3-pentylbenzo[c]chromen-1-ol and betaine characterized by having an X-ray diffractogram that comprises characteristic peaks at 6.3, 7.1 and 9.0±0.3 degrees 2 theta at a Cu-Kα radiation, λ=1.5406 Å;

6,6,9-trimethyl-3-pentylbenzo[c]chromen-1-ol and L-proline characterized by having an X-ray diffractogram that comprises characteristic peaks at 4.2, 5.6 and 9.0±0.3 degrees 2 theta at a Cu-Kα radiation, λ=1.5406 Å;

6,6,9-trimethyl-3-pentylbenzo[c]chromen-1-ol and L-proline characterized by having an X-ray diffractogram that comprises characteristic peaks at 4.7, 10.9 and 12.5±0.3 degrees 2 theta at a Cu-Kα radiation, λ=1.5406 Å;

6,6,9-trimethyl-3-pentylbenzo[c]chromen-1-ol and D-proline characterized by having an X-ray diffractogram that comprises characteristic peaks at 4.7, 10.9 and 12.5±0.3 degrees 2 theta at a Cu-Kα radiation, λ=1.5406 Å;

6,6,9-trimethyl-3-pentylbenzo[c]chromen-1-ol and D-proline characterized by having an X-ray diffractogram that comprises characteristic peaks at 5.1, 10.2 and 16.1±0.3 degrees 2 theta at a Cu-Kα radiation, λ=1.5406 Å;

2-[(2E)-3,7-dimethylocta-2,6-dien-1-yl]-5-pentylbenzene-1,3-diol and betaine characterized by having an X-ray diffractogram that comprises characteristic peaks at 7.8, 15.8 and 23.8±0.3 degrees 2 theta at a Cu-Kα radiation, λ=1.5406 Å;

2-[(2E)-3,7-dimethylocta-2,6-dien-1-yl]-5-pentylbenzene-1,3-diol and L-carnitine characterized by having an X-ray diffractogram that comprises characteristic peaks at 7.0, 14.1 and 19.8±0.3 degrees 2 theta at a Cu-Kα radiation, λ=1.5406 Å;

2-((1R,6R)-3-methyl-6-(prop-1-en-2-yl) cyclohex-2-enyl)-5-propylbenzene-1,3-diol and L-proline characterized by having an X-ray diffractogram that comprises characteristic peaks at 6.1, 9.8 and 12.0±0.3 degrees 2 theta at a Cu-Kα radiation, λ=1.5406 Å; and 2-((1R,6R)-3-methyl-6-(prop-1-en-2-yl) cyclohex-2-enyl)-5-propylbenzene-1,3-diol and L-carnitine characterized by having an X-ray diffractogram that comprises characteristic peaks at 6.9, 10.6 and 11.1±0.3 degrees 2 theta at a Cu-Kα radiation, λ=1.5406 Å.

2. The cocrystal of a cannabinoid according to claim 1, which is a cocrystal selected from the group consisting of:

(−)-(6aR,10aR)-6,6,9-trimethyl-3-pentyl-6a,7,8,10a-tetrahydro-6H-benzo[c]chromen-1-ol and L-proline characterized by having an X-ray diffractogram that comprises characteristic peaks at 5.1, 11.5 and 20.5±0.3 degrees 2 theta at a Cu-Kα radiation, λ=1.5406 Å;

(−)-(6aR,10aR)-6,6,9-trimethyl-3-pentyl-6a,7,8,10a-tetrahydro-6H-benzo[c]chromen-1-ol and D-proline characterized by having an X-ray diffractogram that comprises characteristic peaks at 5.1, 11.4 and 20.6±0.3 degrees 2 theta at a Cu-Kα radiation, λ=1.5406 Å;

(6aR,10aR)-6,6,9-Trimethyl-3-pentyl-6a,7,10,10a-tetrahydro-6H-benzo[c]chromen-1-ol and L-proline characterized by having an X-ray diffractogram that comprises characteristic peaks at 5.1, 18.7 and 20.5±0.3 degrees 2 theta at a Cu-Kα radiation, λ=1.5406 Å;

(6aR,10aR)-6,6,9-Trimethyl-3-pentyl-6a,7,10,10a-tetrahydro-6H-benzo[c]chromen-1-ol and D-proline characterized by having an X-ray diffractogram that comprises characteristic peaks at 5.1, 16.1 and 20.4±0.3 degrees 2 theta at a Cu-Kα radiation, λ=1.5406 Å;

6,6,9-trimethyl-3-pentylbenzo[c]chromen-1-ol and betaine characterized by having an X-ray diffractogram that comprises characteristic peaks at 6.3, 7.1 and 9.0±0.3 degrees 2 theta at a Cu-Kα radiation, λ=1.5406 Å; and 2-((1R,6R)-3-methyl-6-(prop-1-en-2-yl) cyclohex-2-enyl)-5-propylbenzene-1,3-diol and L-carnitine characterized by having an X-ray diffractogram that comprises characteristic peaks at 6.9, 10.6 and 11.1±0.3 degrees 2 theta at a Cu-Kα radiation, λ=1.5406 Å.

* * * * *